US009512137B2

(12) United States Patent  
Ito et al.

(10) Patent No.: US 9,512,137 B2
(45) Date of Patent: Dec. 6, 2016

(54) ORGANIC ELECTROLUMINESCENCE DEVICE

(75) Inventors: Hirokatsu Ito, Sodegaura (JP); Hiroyuki Saito, Sodegaura (JP); Yumiko Mizuki, Sodegaura (JP); Masahiro Kawamura, Sodegaura (JP); Yuichiro Kawamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 659 days.

(21) Appl. No.: 13/509,878

(22) PCT Filed: Aug. 5, 2011

(86) PCT No.: PCT/JP2011/004458
§ 371 (c)(1),
(2), (4) Date: May 15, 2012

(87) PCT Pub. No.: WO2012/017680
PCT Pub. Date: Feb. 9, 2012

(65) Prior Publication Data
US 2012/0256172 A1 Oct. 11, 2012

(30) Foreign Application Priority Data
Aug. 5, 2010 (JP) .................................. 2010-176249

(51) Int. Cl.
*H01L 51/54* (2006.01)
*C09K 11/06* (2006.01)
*C07D 493/04* (2006.01)
*H01L 51/00* (2006.01)
*C07C 255/50* (2006.01)
*C07C 255/51* (2006.01)
*C07C 255/52* (2006.01)
*C07D 519/00* (2006.01)
*C07D 307/91* (2006.01)
*C07D 307/77* (2006.01)
*H01L 51/50* (2006.01)

(52) U.S. Cl.
CPC ........... *C07D 493/04* (2013.01); *C07C 255/50* (2013.01); *C07C 255/51* (2013.01); *C07C 255/52* (2013.01); *C07D 307/77* (2013.01); *C07D 307/91* (2013.01); *C07D 519/00* (2013.01); *H01L 51/0055* (2013.01); *H01L 51/0058* (2013.01); *C07C 2103/18* (2013.01); *C07C 2103/24* (2013.01); *C07C 2103/26* (2013.01); *C07C 2103/40* (2013.01); *C07C 2103/42* (2013.01); *C07C 2103/48* (2013.01); *C07C 2103/50* (2013.01); *C07C 2103/52* (2013.01); *H01L 51/5048* (2013.01)

(58) Field of Classification Search
None
See application file for complete search history.

(56) References Cited

U.S. PATENT DOCUMENTS

| | | | |
|---|---|---|---|
| 6,465,115 B2 | 10/2002 | Shi et al. | |
| 6,861,163 B2 | 3/2005 | Cheng et al. | |
| 7,056,601 B2 | 6/2006 | Cosimbescu et al. | |
| 7,122,711 B2 | 10/2006 | Kamikawa et al. | |
| 7,189,989 B2 | 3/2007 | Ise | |
| 7,488,856 B2 | 2/2009 | Schwalm et al. | |
| 7,651,787 B2 | 1/2010 | Seo et al. | |
| 7,667,043 B2 | 2/2010 | Getty et al. | |
| 7,794,855 B2 | 9/2010 | Iwawaki et al. | |
| 7,833,632 B2 | 11/2010 | Kawamura et al. | |
| 8,092,924 B2 | 1/2012 | Kwong et al. | |
| 8,557,401 B2 | 10/2013 | Kosuge et al. | |
| 8,569,747 B2 | 10/2013 | Yoshinaga et al. | |
| 8,580,404 B2 | 11/2013 | Kwong et al. | |
| 2003/0087126 A1† | 5/2003 | Ishida | |
| 2003/0134147 A1* | 7/2003 | Burn et al. ................... 428/690 |
| 2004/0161633 A1† | 8/2004 | Seo | |
| 2004/0247937 A1 | 12/2004 | Chen et al. | |
| 2005/0089717 A1 | 4/2005 | Cosimbescu et al. | |
| 2005/0124656 A1 | 6/2005 | Swinnen et al. | |
| 2006/0014046 A1 | 1/2006 | Wang et al. | |
| 2006/0222886 A1* | 10/2006 | Kwong et al. ............... 428/690 |
| 2006/0269782 A1 | 11/2006 | Liao et al. | |
| 2006/0269783 A1* | 11/2006 | Yu ........................... B32B 19/00 428/690 |
| 2007/0200490 A1 | 8/2007 | Kawamura et al. | |
| 2009/0015144 A1 | 1/2009 | Takashima et al. | |
| 2009/0066227 A1 | 3/2009 | Okinaka et al. | |
| 2009/0096368 A1 | 4/2009 | Kamatani et al. | |
| 2009/0233125 A1 | 9/2009 | Choi et al. | |
| 2009/0309488 A1* | 12/2009 | Kato ..................... C07D 487/04 313/504 |
| 2010/0039027 A1* | 2/2010 | Takashima ........... C07D 235/18 313/504 |
| 2010/0096982 A1 | 4/2010 | Eum et al. | |
| 2010/0109555 A1 | 5/2010 | Ichimura et al. | |
| 2011/0054228 A1 | 3/2011 | Kim et al. | |

(Continued)

FOREIGN PATENT DOCUMENTS

| | | |
|---|---|---|
| CN | 1362464 A | 8/2002 |
| CN | 1737080 A | 2/2006 |

(Continued)

OTHER PUBLICATIONS

Han et al. Chemical Physics Letters 2008, 453, 129-135. Date of publication: Jan. 8, 2008.*

(Continued)

*Primary Examiner* — Andrew K Bohaty
(74) *Attorney, Agent, or Firm* — Oblon, McClelland, Maier & Neustadt, L.L.P.

(57) ABSTRACT

An organic electroluminescence device sequentially includes an anode, an emitting layer, an electron-transporting region, and a cathode, the electron-transporting region including an electron-transporting material that includes a cyano group and an aromatic ring group.

17 Claims, 1 Drawing Sheet

(56) References Cited

U.S. PATENT DOCUMENTS

| | | |
|---|---|---|
| 2011/0175079 A1 | 7/2011 | Yokoyama et al. |
| 2011/0288292 A1 | 11/2011 | Parham et al. |
| 2011/0295047 A1 | 12/2011 | Itabashi et al. |
| 2011/0315965 A1 | 12/2011 | Takashima et al. |
| 2012/0032156 A1 | 2/2012 | Kwong et al. |
| 2012/0126205 A1 | 5/2012 | Kawamura et al. |
| 2012/0126209 A1 | 5/2012 | Kawamura et al. |
| 2012/0132901 A1 | 5/2012 | Yamada et al. |
| 2012/0187383 A1 | 7/2012 | Gao et al. |
| 2012/0235888 A1 | 9/2012 | Kosuge et al. |
| 2012/0280613 A1 | 11/2012 | Kang et al. |
| 2013/0126787 A1 | 5/2013 | Alessi et al. |

FOREIGN PATENT DOCUMENTS

| | | | |
|---|---|---|---|
| CN | 1785943 A | 6/2006 | |
| CN | 101381601 A | 3/2009 | |
| CN | 101698795 A | 4/2010 | |
| EP | 2 189 508 A2 | 5/2010 | |
| EP | 2 256 176 A1 | 12/2010 | |
| JP | 10-189248 | 7/1998 | |
| JP | 2001-297883 A | 10/2001 | |
| JP | 2002-063988 | 2/2002 | |
| JP | 2003105332 A * | 4/2003 | ............. C09K 11/06 |
| JP | 2003-338377 | 11/2003 | |
| JP | 2005-015403 | 1/2005 | |
| JP | 2005-063938 | 3/2005 | |
| JP | 2005/516061 A | 6/2005 | |
| JP | 2006-518545 A | 8/2006 | |
| JP | 2007-511067 A | 4/2007 | |
| JP | 2007-169581 | 7/2007 | |
| JP | 2007-224171 | 9/2007 | |
| JP | 2008-037755 | 2/2008 | |
| JP | 2008-60379 A | 3/2008 | |
| JP | 2008-141217 | 6/2008 | |
| JP | 2008-150343 | 7/2008 | |
| JP | 2008-258603 A | 10/2008 | |
| JP | 2008-546185 A | 12/2008 | |
| JP | 2009-004351 | 1/2009 | |
| JP | 2009-010181 | 1/2009 | |
| JP | 2010-111621 A | 5/2010 | |
| JP | 2010-135177 | 6/2010 | |
| JP | 2010-185008 | 8/2010 | |
| JP | 2010-209211 | 9/2010 | |
| JP | 4617393 B1 | 10/2010 | |
| JP | 2010-251585 | 11/2010 | |
| JP | 2011-151108 | 8/2011 | |
| JP | 2012-028629 | 2/2012 | |
| JP | 2012-079892 | 4/2012 | |
| JP | 2012-079899 | 4/2012 | |
| JP | 2012-099593 | 5/2012 | |
| JP | 2012-119592 | 6/2012 | |
| KR | 10-20090072152 | 7/2009 | |
| KR | 10-20090086920 | 8/2009 | |
| KR | 10-20090088177 | 8/2009 | |
| KR | 10-20100002030 | 1/2010 | |
| KR | 10-20100119077 | 11/2010 | |
| KR | 10-20110026989 | 3/2011 | |
| KR | 10-20110043270 | 4/2011 | |
| KR | 10-20110049554 | 5/2011 | |
| KR | 10-20110064222 | 6/2011 | |
| KR | 10-20110076017 | 7/2011 | |
| KR | 10-20110099195 | 9/2011 | |
| KR | 10-20110123701 | 11/2011 | |
| KR | 10-20120043878 | 5/2012 | |
| KR | 10-20120051598 | 5/2012 | |
| KR | 10-20120117675 | 10/2012 | |
| KR | 10-20120117693 | 10/2012 | |
| WO | WO 03/060956 A2 | 7/2003 | |
| WO | WO 2005/097756 A1 | 10/2005 | |
| WO | WO 2008/059713 A1 | 5/2008 | |
| WO | WO 2010/035723 A1 | 4/2010 | |
| WO | WO 2010/074087 A1 | 7/2010 | |
| WO | 2011/008169 | 1/2011 | |
| WO | 2011/149240 A2 | 12/2011 | |
| WO | 2012/014822 A1 | 2/2012 | |
| WO | 2012/030145 A1 | 3/2012 | |
| WO | 2012/063663 A1 | 5/2012 | |
| WO | 2012/133042 A1 | 10/2012 | |
| WO | 2012/133043 A1 | 10/2012 | |
| WO | 2012/137741 A1 | 10/2012 | |
| WO | 2012/141109 A1 | 10/2012 | |
| WO | 2012/141273 A1 | 10/2012 | |
| WO | 2012/141274 A1 | 10/2012 | |
| WO | 2012/169635 A1 | 12/2012 | |

OTHER PUBLICATIONS

Machine translation of JP2003-105332. Date of publication: Apr. 9, 2003.*

U.S. Appl. No. 13/297,905, filed Nov. 17, 2011, Kawamura, et al.

International Search Report issued Oct. 18, 2011 in PCT/JP2011/004458.

U.S. Appl. No. 14/871,055, filed Sep. 30, 2015, Kawamura, et al.

* cited by examiner
† cited by third party

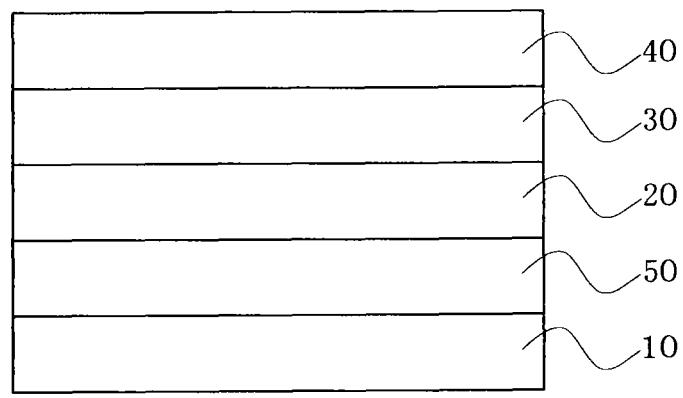

ORGANIC ELECTROLUMINESCENCE DEVICE

TECHNICAL FIELD

The invention relates to an organic electroluminescence device.

BACKGROUND ART

An organic electroluminescence (EL) device that utilizes an organic substance is a promising inexpensive solid-state emitting large full-color display, and has been extensively developed.

The organic EL device normally includes an emitting layer and a pair of opposing electrodes disposed on either side of the emitting layer. When an electric field is applied between the electrodes, electrons and holes are injected into the emitting layer respectively from the cathode and the anode. The electrons and the holes recombine in the emitting layer to produce an excited state, and the energy is emitted as light when the excited state returns to the ground state.

It is difficult to improve the performance of an organic EL device in which the hole-injecting function, the electron-injecting function, and the emitting function are implemented by a single layer. Therefore, the performance of an organic EL device has been improved by providing a plurality of organic layers that differ in function between the electrodes. A structure in which three or more layers such as a hole-transporting layer, an emitting layer, and an electron-transporting layer are stacked between two electrodes has been generally employed.

An organic EL device that was developed in an early stage was insufficient in terms of the drive voltage, the luminous efficiency, and the durability. Therefore, various technical improvements have been made to address this problem. For example, Patent Documents 1 and 2 disclose an organic EL device material that aims at improving the drive voltage, the luminous efficiency, and the durability.

Patent Document 1 discloses a material that includes an anthracene skeleton and an imidazole skeleton as an electron-injecting/transporting material that may improve the lifetime and the efficiency of the device. Patent Document 2 discloses a nitrogen-containing heterocyclic derivative that includes a specific imidazole skeleton as an electron-transporting material that may improve the luminous efficiency at a low voltage.

Specifically, Patent Documents 1 and 2 improve the performance of the organic EL device by utilizing a nitrogen-containing heterocyclic derivative as the electron-transporting material.

Patent Document 3 aims at improving the lifetime, the luminance, and the power consumption of an organic emitting device, and discloses an organic layer that includes an anthracene derivative compound and an ion metal complex, or two types of anthracene derivative compound.

Patent Document 4 discloses a compound that includes a benzofluoranthene skeleton as a dopant material for an emitting layer.

RELATED-ART DOCUMENT

Patent Document

Patent Document 1: WO2003/060956
Patent Document 2: WO2005/097756
Patent Document 3: JP-A-2008-258603
Patent Document 4: WO2008/059713

SUMMARY OF THE INVENTION

An object of the invention is to provide an organic EL device that exhibits a high efficiency and a long lifetime.

The inventors of the invention conducted extensive studies, and found that excellent effects (low voltage, high efficiency, and long lifetime) are achieved when using an aromatic hydrocarbon material that includes a cyano group as an electron-transporting material for an organic EL device. This finding has led to the completion of the invention.

The electron-transporting material must include an electron-transporting skeleton and an electron-attracting skeleton. Patent Documents 1 to 3 disclose using a material that includes a nitrogen-containing heterocyclic substituent (e.g., imidazole skeleton), or a layer that includes an aromatic hydrocarbon compound and a metal complex or the like as the electron-transporting material.

A material that includes a nitrogen-containing heterocyclic substituent (e.g., imidazole skeleton) exhibits an excellent electron-injecting/transporting capability. However, a nitrogen-containing heterocyclic substituent may exhibit insufficient hole resistance. Since a material that does not include a nitrogen-containing heterocyclic derivative increases the drive voltage, a metal complex or the like must be used in combination with the material. The production process becomes complex when forming an electron-injecting/transporting layer using a plurality of materials in combination. Therefore, a single material that can form the electron-injecting/transporting layer has been desired.

The inventors conducted extensive studies, and found that an organic EL device that can be driven at a low voltage and exhibits a high efficiency and a long lifetime can be obtained by utilizing an electron-transporting material that includes a cyano group and an aromatic ring group.

The invention provides the following organic EL device.

1. An organic electroluminescence device sequentially including an anode, an emitting layer, an electron-transporting region, and a cathode, the electron-transporting region including an electron-transporting material that includes a cyano group and an aromatic ring group.

2. The organic electroluminescence device according to 1, wherein the electron-transporting material includes a cyano group, and a monocyclic aromatic ring group and/or a fused aromatic ring group.

3. The organic electroluminescence device according to 1 or 2, wherein the electron-transporting material is shown by a formula (ET),

(ET)

wherein $L_1$ is a single bond or a substituted or unsubstituted (a+1)-valent aromatic ring group having 6 to 50 ring carbon atoms, $Ar_1$ is a substituted or unsubstituted (1+b)-valent aromatic ring group having 6 to 50 ring carbon atoms, a, b, and c are independently an integer from 1 to 3, and A is a fused aromatic ring group selected from the group consisting of fused aromatic ring groups shown by formulas (A-1) to (A-12),

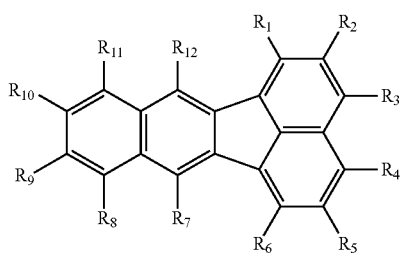
(A-1)
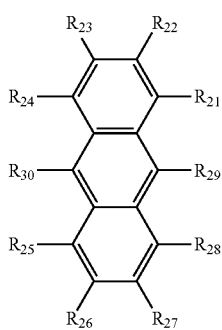
(A-2)
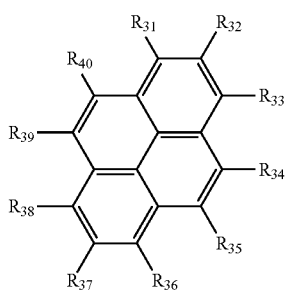
(A-3)
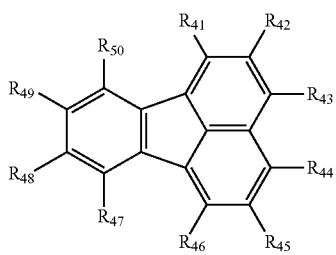
(A-4)
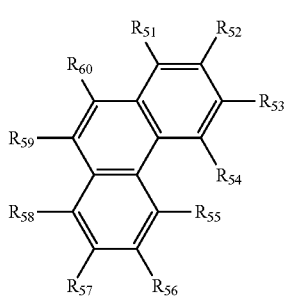
(A-5)
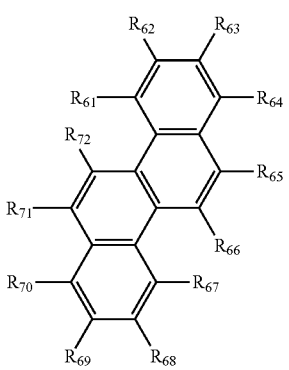
(A-6)
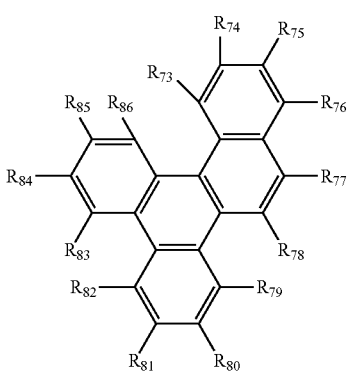
(A-7)
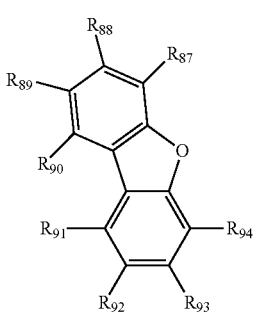
(A-8)
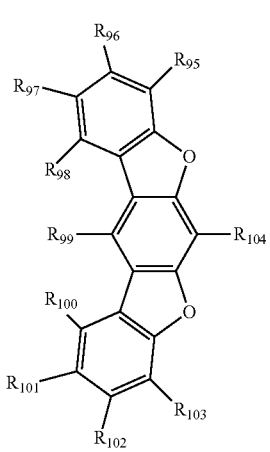
(A-9)

-continued

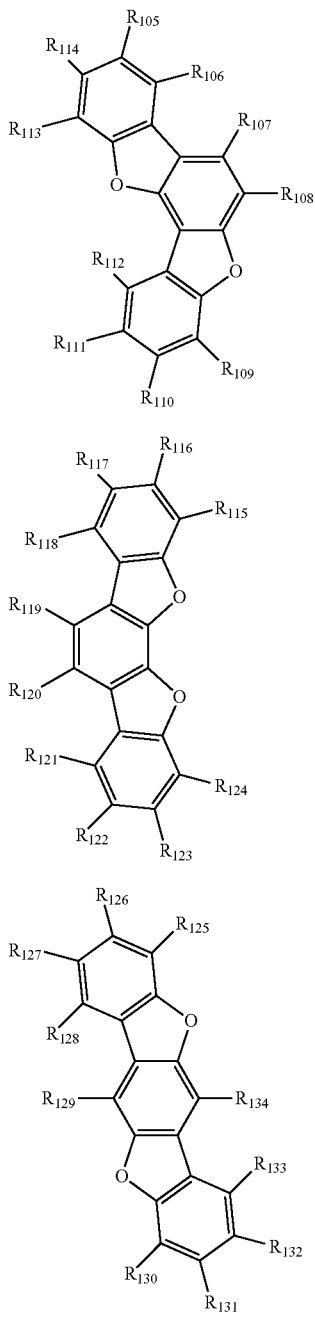

wherein one or more of $R_1$ to $R_{12}$, $R_{21}$ to $R_{30}$, $R_{31}$ to $R_{40}$, $R_{41}$ to $R_{50}$, $R_{51}$ to $R_{60}$, $R_{61}$ to $R_{72}$, $R_{73}$ to $R_{86}$, $R_{87}$ to $R_{94}$, $R_{95}$ to $R_{104}$, $R_{105}$ to $R_{114}$, $R_{115}$ to $R_{124}$, or $R_{125}$ to $R_{134}$ in a number corresponding to c are single bonds to $L_1$, and the remainder of $R_1$ to $R_{12}$, $R_{21}$ to $R_{30}$, $R_{31}$ to $R_{40}$, $R_{41}$ to $R_{50}$, $R_{51}$ to $R_{60}$, $R_{61}$ to $R_{72}$, $R_{73}$ to $R_{86}$, $R_{87}$ to $R_{94}$, $R_{95}$ to $R_{104}$, $R_{105}$ to $R_{114}$, $R_{115}$ to $R_{124}$, or $R_{125}$ to $R_{134}$ are independently a hydrogen atom, a halogen atom, a cyano group, a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 50 ring carbon atoms, provided that adjacent groups among the remainder of $R_1$ to $R_{12}$, $R_{21}$ to $R_{30}$, $R_{31}$ to $R_{40}$, $R_{41}$ to $R_{50}$, $R_{51}$ to $R_{60}$, $R_{61}$ to $R_{72}$, $R_{73}$ to $R_{86}$, $R_{87}$ to $R_{94}$, $R_{95}$ to $R_{104}$, $R_{105}$ to $R_{114}$, $R_{115}$ to $R_{124}$, or $R_{125}$ to $R_{134}$ may bond to form a ring.

4. The organic electroluminescence device according to 3, wherein the electron-transporting material is shown by a formula (1),

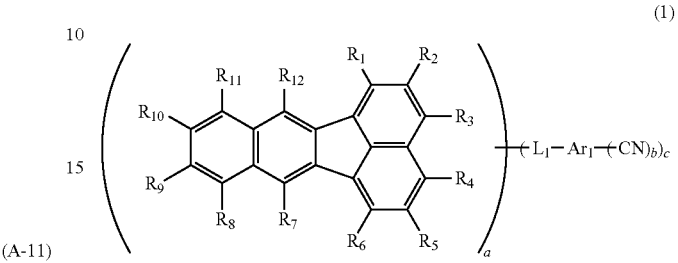

wherein a, b, c, $L_1$, $Ar_1$, and $R_1$ to $R_{12}$ are the same as defined above.

5. The organic electroluminescence device according to 4, wherein $R_3$ or $R_4$ is a single bond to $L_1$.

6. The organic electroluminescence device according to 4 or 5, wherein a=1 and c=1.

7. The organic electroluminescence device according to any one of 4 to 6, wherein $R_7$ and $R_{12}$ are unsubstituted phenyl groups.

8. The organic electroluminescence device according to any one of 1 to 7, wherein the electron-transporting region further includes a reducing dopant.

9. The organic electroluminescence device according to 8, wherein the reducing dopant is one substance or two or more substances selected from the group consisting of alkali metals, alkaline-earth metals, rare earth metals, alkali metal oxides, alkali metal halides, alkaline-earth metal oxides, alkaline-earth metal halides, rare earth metal oxides, rare earth metal halides, organic complexes of alkali metals, organic complexes of alkaline-earth metals, and organic complexes of rare earth metals.

10. A compound shown by a formula (ET), the compound including a cyano group and an aromatic ring group,

wherein $L_1$ is a single bond or a substituted or unsubstituted (a+1)-valent aromatic ring group having 6 to 50 ring carbon atoms, $Ar_1$ is a substituted or unsubstituted (1+b)-valent aromatic ring group having 6 to 50 ring carbon atoms, a, b, and c are independently an integer from 1 to 3, and A is a fused aromatic ring group selected from the group consisting of fused aromatic ring groups shown by formulas (A-1) to (A-12),

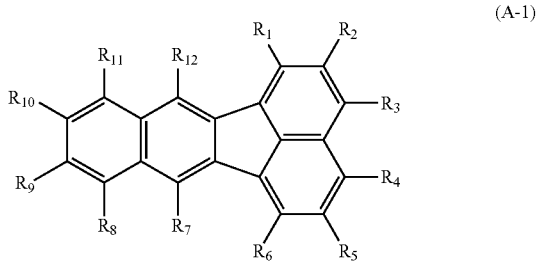

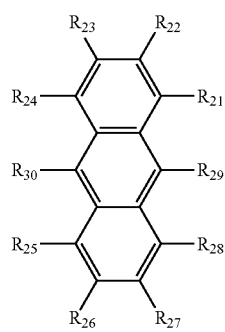 (A-2)
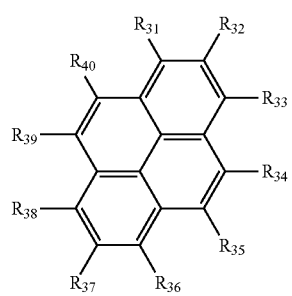 (A-3)
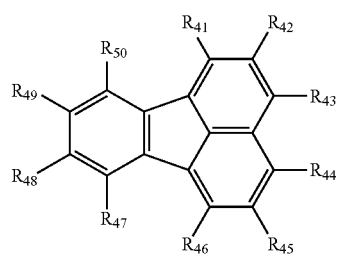 (A-4)
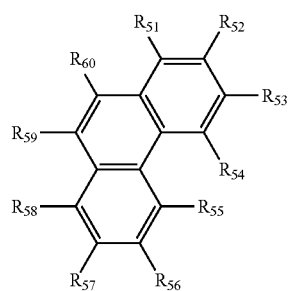 (A-5)
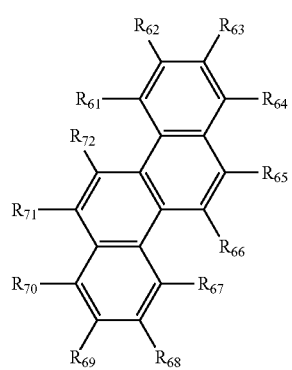 (A-6)
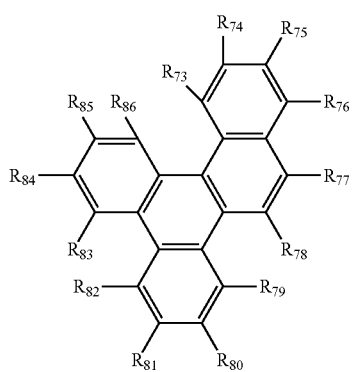 (A-7)
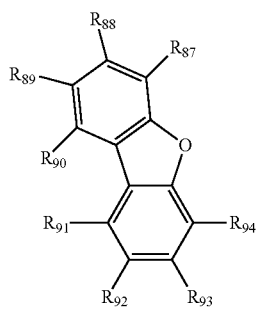 (A-8)
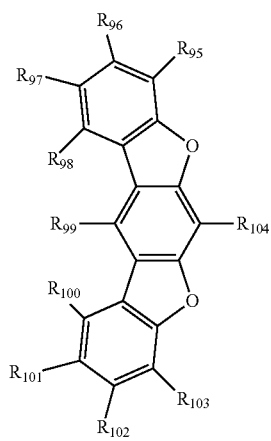 (A-9)
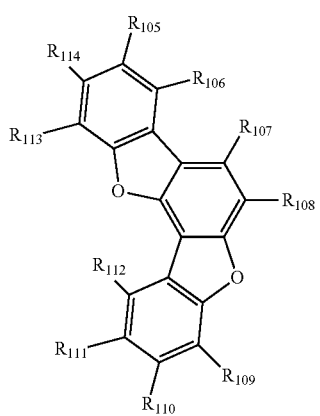 (A-10)

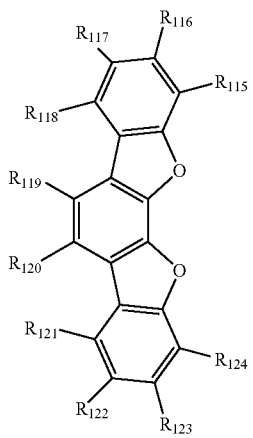

(A-11)

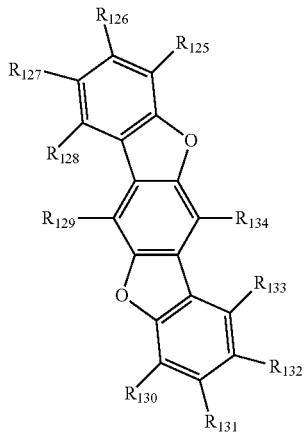

(A-12)

wherein one or more of $R_1$ to $R_{12}$, $R_{21}$ to $R_{30}$, $R_{31}$ to $R_{40}$, $R_{41}$ to $R_{50}$, $R_{51}$ to $R_{60}$, $R_{61}$ to $R_{72}$, $R_{73}$ to $R_{86}$, $R_{87}$ to $R_{94}$, $R_{95}$ to $R_{104}$, $R_{105}$ to $R_{114}$, $R_{115}$ to $R_{124}$, or $R_{125}$ to $R_{134}$ in a number corresponding to c are single bonds to $L_1$, and the remainder of $R_1$ to $R_{12}$, $R_{21}$ to $R_{30}$, $R_{31}$ to $R_{40}$, $R_{41}$ to $R_{50}$, $R_{51}$ to $R_{60}$, $R_{61}$ to $R_{72}$, $R_{73}$ to $R_{86}$, $R_{87}$ to $R_{94}$, $R_{95}$ to $R_{104}$, $R_{105}$ to $R_{114}$, $R_{115}$ to $R_{124}$, or $R_{125}$ to $R_{134}$ are independently a hydrogen atom, a halogen atom, a cyano group, a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 50 ring carbon atoms, provided that adjacent groups among the remainder of $R_1$ to $R_{12}$, $R_{21}$ to $R_{30}$, $R_{31}$ to $R_{40}$, $R_{41}$ to $R_{50}$, $R_{51}$ to $R_{60}$, $R_{61}$ to $R_{72}$, $R_{73}$ to $R_{86}$, $R_{87}$ to $R_{94}$, $R_{95}$ to $R_{104}$, $R_{105}$ to $R_{114}$, $R_{115}$ to $R_{124}$, or $R_{125}$ to $R_{134}$ may bond to form a ring.

The invention thus provides an organic EL device that can be driven at a low voltage, and exhibits a high efficiency and a long lifetime.

BRIEF DESCRIPTION OF THE DRAWINGS

FIG. 1 is a view illustrating one embodiment of the invention.

DESCRIPTION OF THE EMBODIMENTS

An organic EL device according to the invention sequentially includes at least an anode 10, an emitting layer 20, an electron-transporting region 30, and a cathode 40, the electron-transporting region 30 including an electron-transporting material that includes a cyano group and an aromatic ring group (see FIG. 1).

The organic EL device according to the invention may include a hole-transporting region 50 (see FIG. 1) between the anode 10 and the emitting layer 20, or may further include an additional layer.

The aromatic ring group included in the electron-transporting material (hereinafter may be referred to as "electron-transporting material according to the invention") included in the electron-transporting region of the organic EL device according to the invention is a group that includes one aromatic ring or a plurality of aromatic rings (fused ring) that may include an oxygen atom and/or a sulfur atom. Specifically, the term "aromatic ring group" used herein includes a monocyclic aromatic ring group and a fused aromatic ring group. The electron-transporting material according to the invention does not include a nitrogen-containing heterocyclic group as a substituent that substitutes the aromatic ring group in order to achieve a low drive voltage, a high efficiency, and a long lifetime.

The term "monocyclic aromatic ring group" used herein refers to a group that includes one ring that does not have a fused ring structure, or a group in which a plurality of rings that do not have a fused ring structure are bonded. The term "fused aromatic ring group" used herein refers to a group that has a structure in which two or more rings are fused.

The number of ring atoms of the monocyclic aromatic ring group is preferably 5 to 50 (more preferably 5 to 30, and still more preferably 5 to 20), and the number of ring atoms of the fused aromatic ring group is preferably 8 to 50 (more preferably 8 to 30, and still more preferably 8 to 20).

Specific examples of a preferable monocyclic aromatic ring group having 5 to 50 (preferably 5 to 30, and more preferably 5 to 20) ring atoms include an aryl group (e.g., phenyl group, biphenyl group, terphenyl group, and quarter phenyl group) and a heterocyclic group (e.g., furyl group and thienyl group).

Among these, an aryl group is preferable, and a phenyl group, a biphenyl group, and a terphenyl group are particularly preferable.

Specific examples of the fused aromatic ring group having 8 to 50 (preferably 8 to 30, and more preferably 8 to 20) ring atoms include a fused aryl group (e.g., naphthyl group, phenanthryl group, anthryl group, chrysenyl group, benzanthryl group, benzophenanthryl group, triphenylenyl group, benzochrysenyl group, indenyl group, fluorenyl group, 9,9-dimethylfluorenyl group, benzofluorenyl group, dibenzofluorenyl group, fluoranthenyl group, benzofluoranthenyl group, and pyrenyl group) and a fused heterocyclic group (e.g., benzofuranyl group, benzothiophenyl group, dibenzofuranyl group, and dibenzothiophenyl group).

Among these, a naphthyl group, a phenanthryl group, an anthryl group, a 9,9-dimethylfluorenyl group, a fluoranthenyl group, a benzanthryl group, a pyrenyl group, a dibenzothiophenyl group, and a dibenzofuranyl group are preferable.

The aromatic ring group included in the electron-transporting material according to the invention may be formed of monocyclic aromatic ring groups, or may be formed of a monocyclic aromatic ring group and a fused aromatic ring group, or may be formed of fused aromatic ring groups.

The electron-transporting material according to the invention is preferably any of the compounds shown by the following formulas (1) to (12).

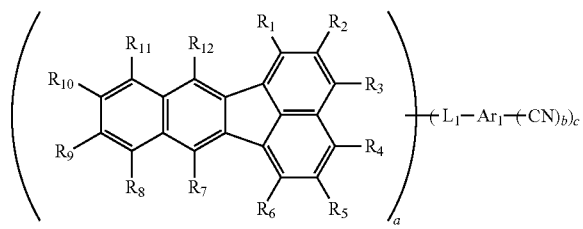

(1)

wherein a, b, and c are independently an integer from 1 to 3. a or c is preferably 1. b is preferably 1. One or more of $R_1$ to $R_{12}$ in a number corresponding to c are single bonds to $L_1$. It is preferable that $R_3$ or $R_4$ be a single bond to $L_1$. The remainder of $R_1$ to $R_{12}$ are independently a hydrogen atom, a halogen atom, a cyano group, a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 50 ring carbon atoms, provided that adjacent groups among the remainder of $R_1$ to $R_{12}$ may bond to form a ring. $L_1$ is a single bond or a substituted or unsubstituted (a+1)-valent aromatic ring group having 6 to 50 ring carbon atoms. $Ar_1$ is a substituted or unsubstituted (1+b)-valent aromatic ring group having 6 to 50 ring carbon atoms.

When a in the formula (1) is an integer equal to or larger than 2, a plurality of benzofluoranthene skeletons may be either identical or different. The single bond to $L_1$ is also arbitrary. When c is an integer equal to or larger than 2, a plurality of $L_1$ and a plurality of cyanoaryl groups ($Ar_1$—$(CN)_b$) may respectively be either identical or different.

The compound shown by the formula (1) includes a benzofluoranthene skeleton and a cyano group. Since a benzofluoranthene skeleton has high planarity so that the molecules overlap advantageously, it is considered that the compound exhibits a high carrier-transporting capability. Since a benzofluoranthene skeleton exhibits high carrier resistance, the lifetime of the organic EL device is expected to be improved. For example, when using an electron-trapping dopant for the emitting layer of the organic EL device, holes may flow to the electron-injecting layer. Since the compound shown by the formula (1) that includes a benzofluoranthene skeleton exhibits excellent hole resistance as compared with a compound that includes an imidazole skeleton or the like, it is considered that a deterioration in the organic EL device can be prevented.

It is preferable that $R_7$ and $R_{12}$ in the formula (1) be unsubstituted phenyl groups.

When $R_7$ and $R_{12}$ are unsubstituted phenyl groups, the planarity of the benzofluoranthene skeleton is considered to be improved. As a result, the distance between the molecules can be reduced due to an increase in the degree of overlap between the molecules, so that the carrier-transporting capability of the compound shown by the formula (1) can be improved.

Each substituent of the compound shown by the formula (1) is described below.

Examples of the halogen atom represented by $R_1$ to $R_{12}$ include a fluorine atom, a chlorine atom, a bromine atom, an iodine atom, and the like. Among these, a fluorine atom is preferable.

Examples of the alkyl group having 1 to 20 (preferably 1 to 6, and more preferably 1 to 4) carbon atoms represented by $R_1$ to $R_{12}$ include an ethyl group, a methyl group, an i-propyl group, an n-propyl group, an s-butyl group, a t-butyl group, a pentyl group, a hexyl group, and the like.

Examples of the cycloalkyl group having 3 to 10 (preferably 3 to 6) ring carbon atoms represented by $R_1$ to $R_{12}$ include a cyclopropyl group, a cyclobutyl group, a cyclopentyl group, a cyclohexyl group, a 4-methylcyclohexyl group, and the like.

The substituted silyl group represented by $R_1$ to $R_{12}$ may be an alkylsilyl group having 3 to 30 carbon atoms or an arylsilyl group having 8 to 30 carbon atoms.

Examples of the alkylsilyl group having 3 to 30 (preferably 3 to 20, and more preferably 3 to 10) carbon atoms include a trimethylsilyl group, a triethylsilyl group, a t-butyldimethylsilyl group, a vinyldimethylsilyl group, a propyldimethylsilyl group, and the like.

Examples of the arylsilyl group having 8 to 30 carbon atoms include a triphenylsilyl group, a phenyldimethylsilyl group, a t-butyldiphenylsilyl group, a tritolylsilyl group, a trixylylsilyl group, a trinaphthylsilyl group, and the like.

Examples of the aryl group having 6 to 50 (preferably 6 to 20, and more preferably 6 to 12) ring carbon atoms represented by $R_1$ to $R_{12}$ include a phenyl group, a naphthyl group, a phenanthryl group, a biphenyl group, a terphenyl group, an anthryl group, a chrysenyl group, a benzophenanthryl group, a benzanthryl group, a benzochrysenyl group, a fluorenyl group, a fluoranthenyl group, a naphthacenyl group, and the like. The aryl group may be a combination of aryl groups (e.g., phenylnaphthyl group or phenylnaphthylphenyl group) as long as the number of ring carbon atoms is 6 to 50.

Examples of the (a+1)-valent aromatic ring group having 6 to 50 (preferably 6 to 20, and more preferably 6 to 12) ring carbon atoms represented by $L_1$ include residues that correspond to a phenylene group, a naphthylene group, a phenanthrylene group, a biphenylene group, a terphenylene group, a quarter phenylene group, an anthrylene group, a pentacenylene group, a perylenylene group, a pycenylene group, a pyrenylene group, a pentaphenylene group, a fluorenylene group, and a chrysenylene group, and the like. The (a+1)-valent aromatic ring group may be a residue that corresponds to a group formed of a combination of aryl groups (e.g., phenylnaphthyl group or phenylnaphthylphenyl group) as long as the number of ring carbon atoms is 6 to 50.

Examples of the (1+b)-valent aromatic ring group having 6 to 50 ring carbon atoms represented by $Ar_1$ include residues that correspond to the groups mentioned above in connection with $R_1$ to $R_{12}$. The (1+b)-valent aromatic ring group is preferably a residue that corresponds to a phenyl group or a naphthyl group.

Examples of a substituent that may substitute each substituent represented by $R_1$ to $R_{12}$, $L_1$, and $Ar_1$ include an alkyl group, an alkylsilyl group, a halogenated alkyl group, an aryl group, a cycloalkyl group, an alkoxy group, a heterocyclic group that does not include a nitrogen atom, an aralkyl group, an aryloxy group, an arylthio group, an alkoxycarbonyl group, a halogen atom, a hydroxyl group, a nitro group, a cyano group, a carboxyl group, and the like. Among these, an aryl group is preferable.

Specific examples of these substituents include those mentioned above.

The term "unsubstituted" used in connection with each substituent of the compound shown by the formula (1) refers to substitution with a hydrogen atom. The term "hydrogen atom" used herein includes light hydrogen and deuterium.

The term "ring carbon atom" used herein refers to a carbon atom that forms a saturated ring, an unsaturated ring, or an aromatic ring. The term "ring atom" used herein refers to a carbon atom or a heteroatom that forms a ring (including a saturated ring, an unsaturated ring, and an aromatic ring).
Specific examples of the electron-transporting material shown by the formula (1) that includes a cyano group and an aromatic ring group are shown below.
ET 1-01
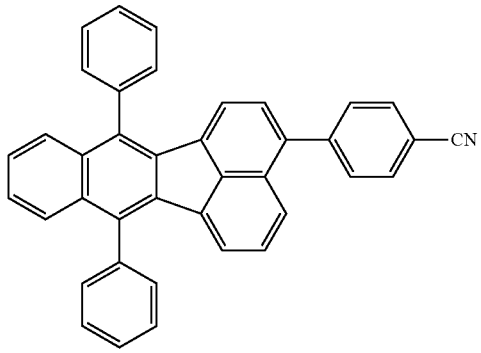
ET 1-02
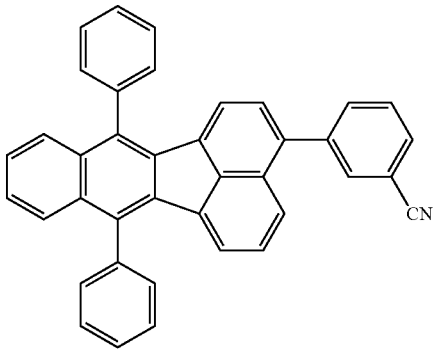
ET 1-03
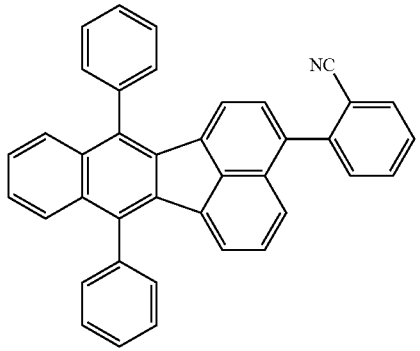
ET 1-04
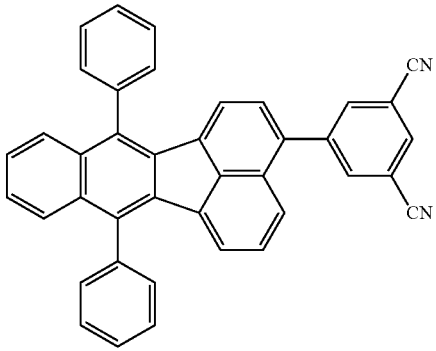
ET 1-05
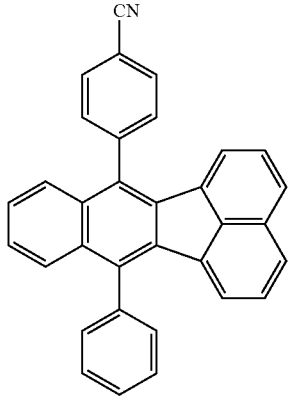
ET 1-06
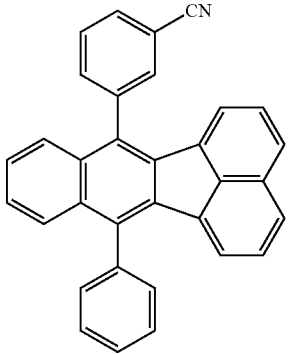
ET 1-07
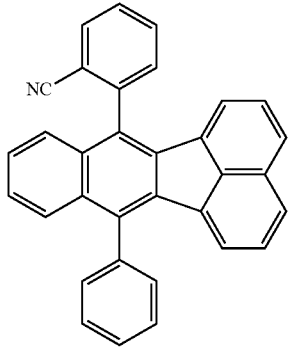
ET 1-08
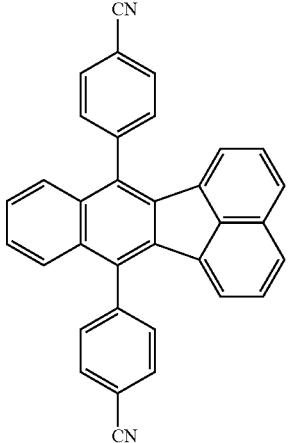

-continued
ET 1-09
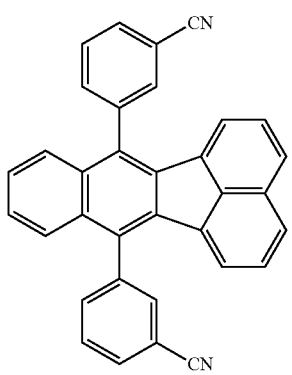
ET 1-10
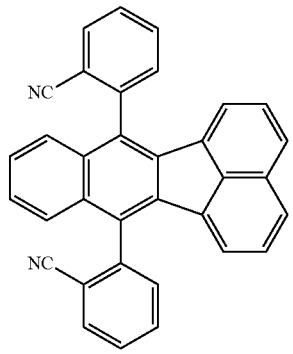
ET 1-11
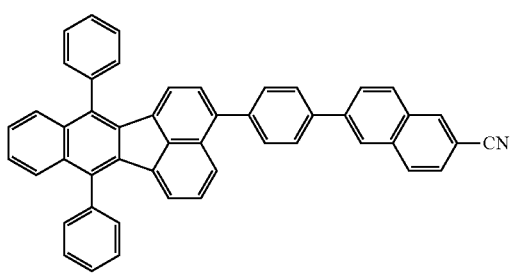
ET 1-12
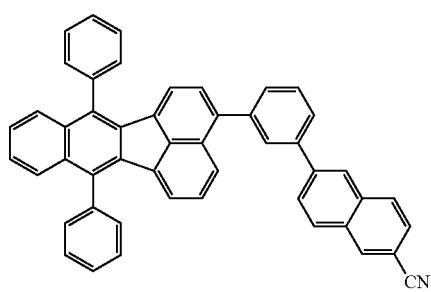
ET 1-13
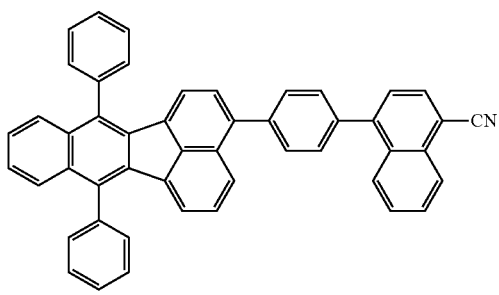
ET 1-14
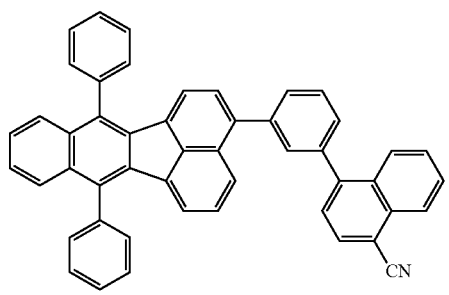
ET 1-15
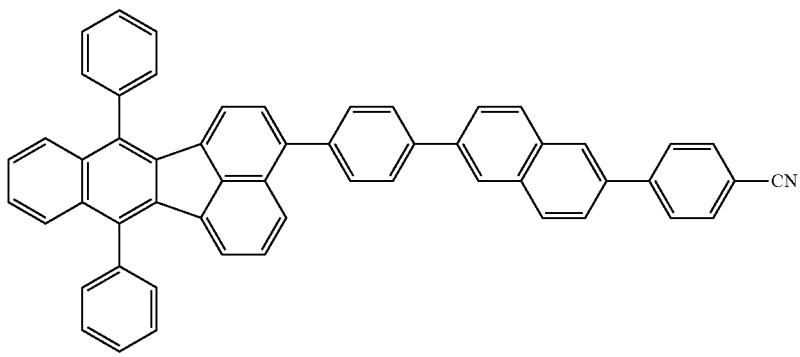

ET 1-16
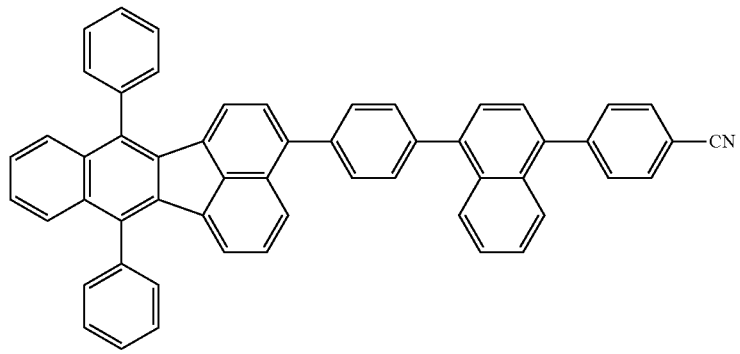
ET 1-17
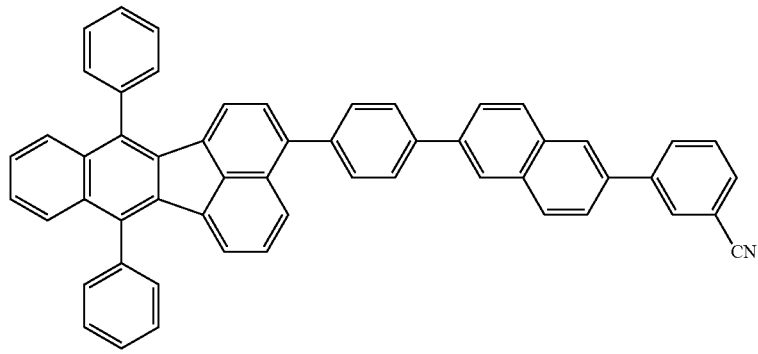
ET 1-18
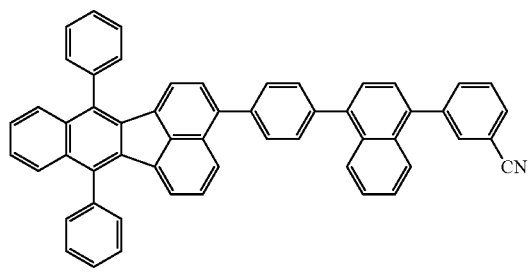
ET 1-19
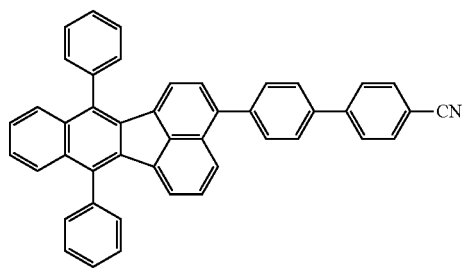
ET 1-20
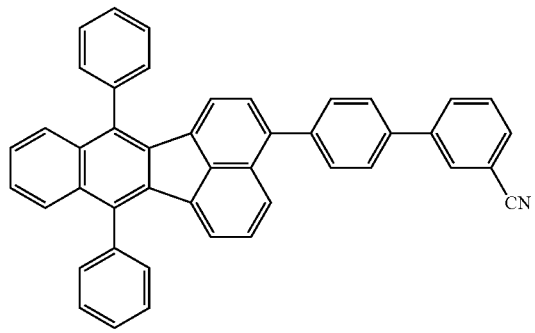
ET 1-21
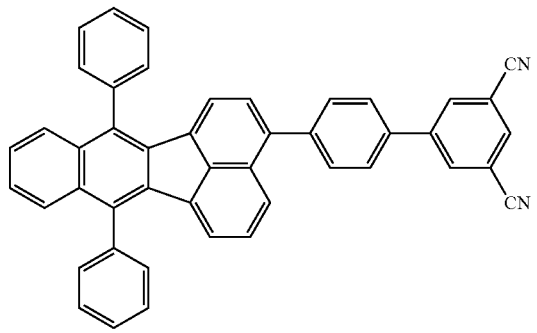

-continued
ET 1-22
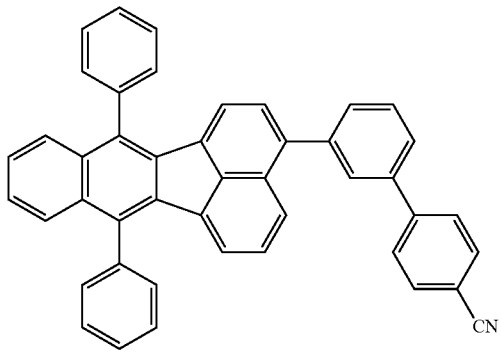
ET 1-23
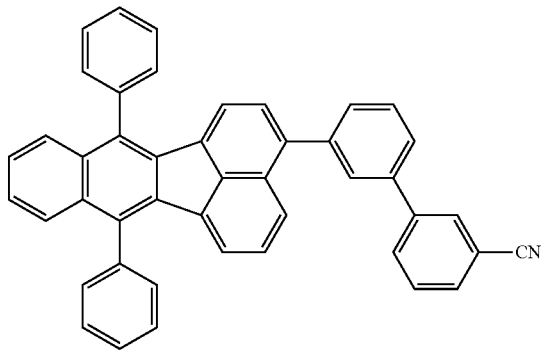
ET 1-24
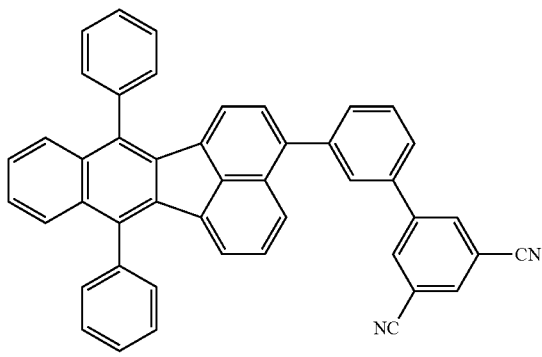
ET 1-25
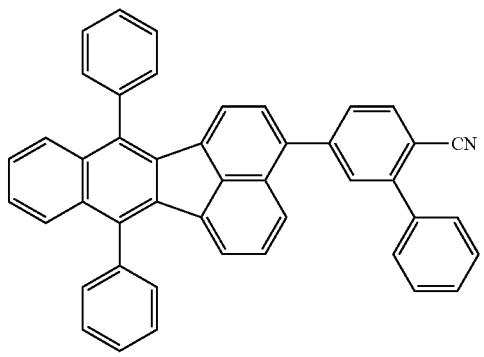
ET 1-26
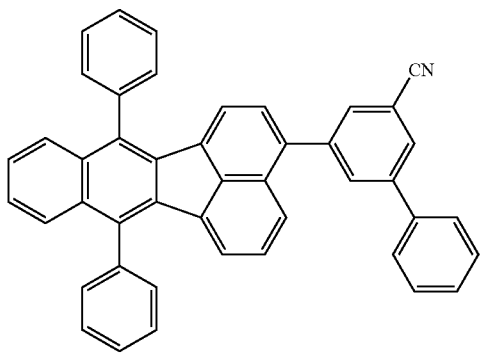
ET 1-27
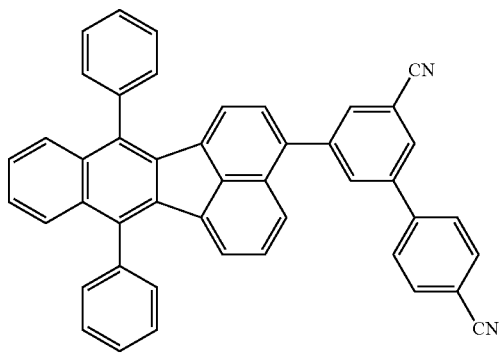
ET 1-28
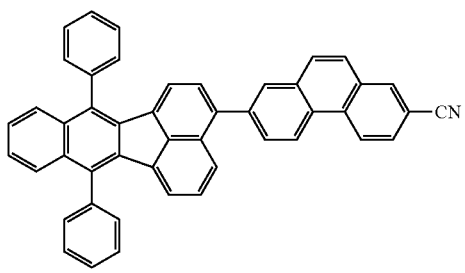
ET 1-29
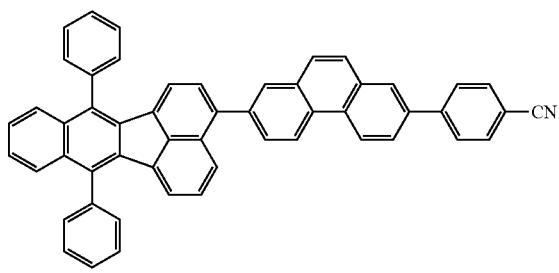

-continued
ET 1-30
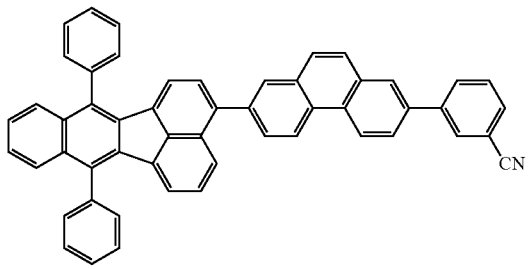
ET 1-31
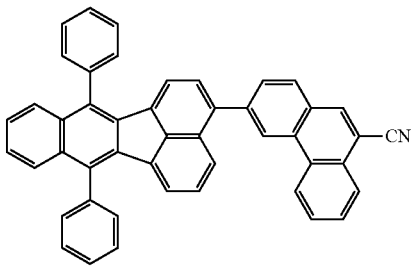
ET 1-32
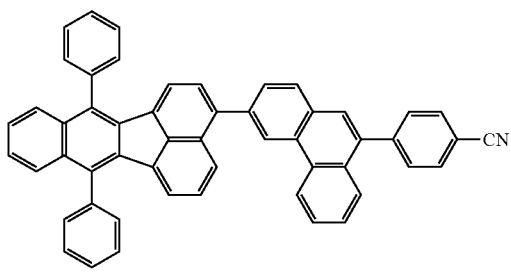
ET 1-33
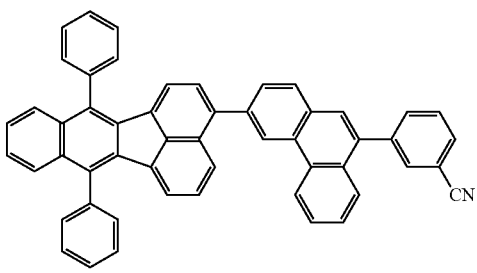
ET 1-34
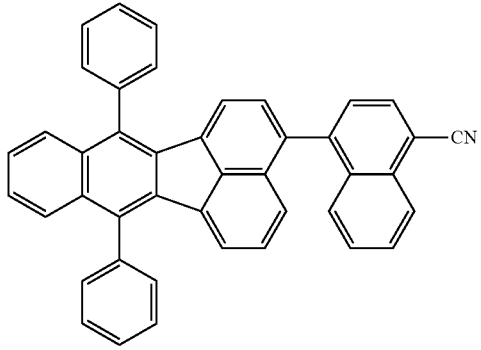
ET 1-35
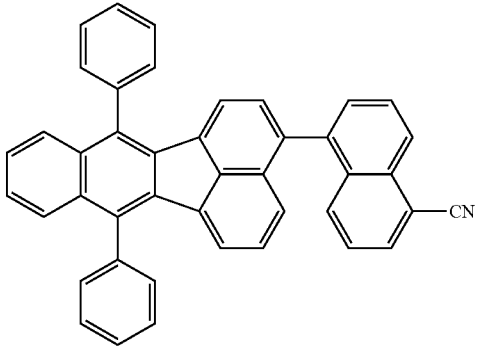
ET 1-36
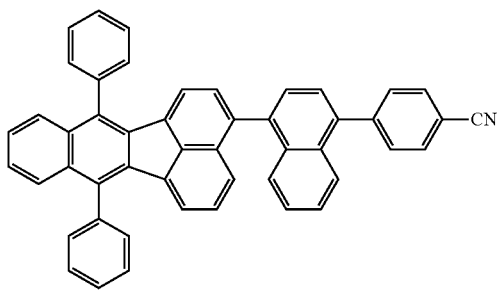
ET 1-37
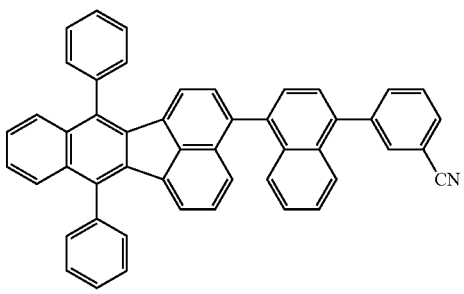
ET 1-38
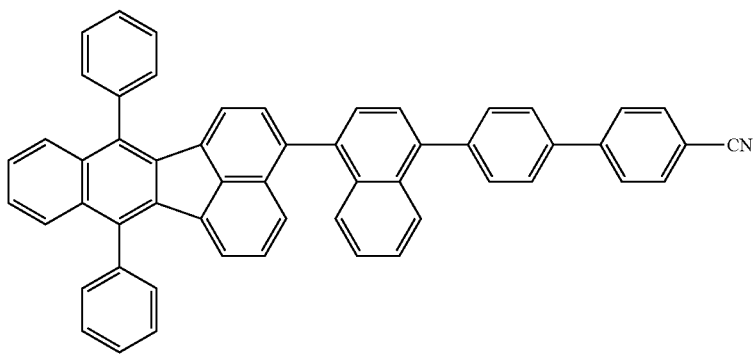

-continued
ET 1-39
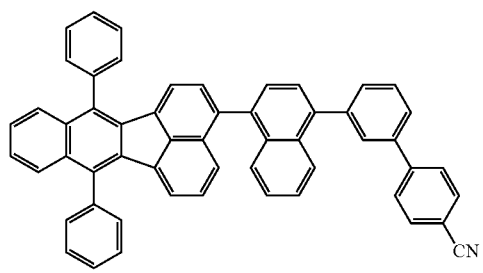
ET 1-40
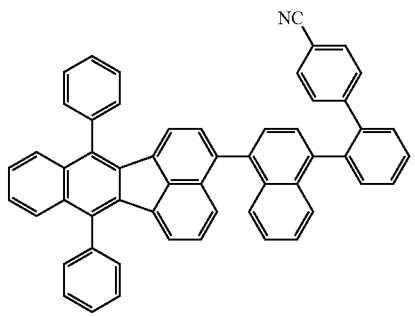
ET 1-41
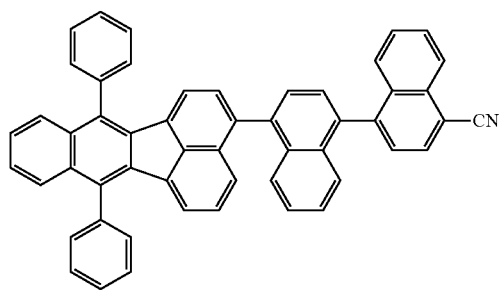
ET 1-42
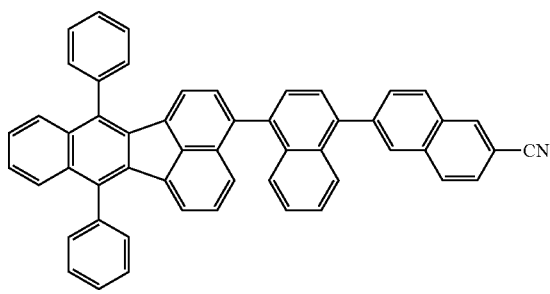
ET 1-43
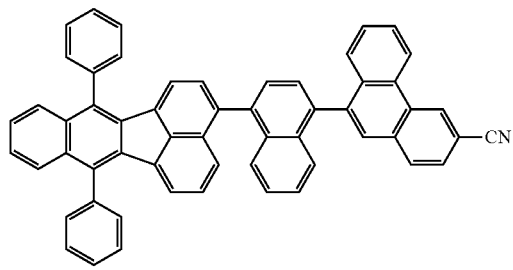
ET 1-44
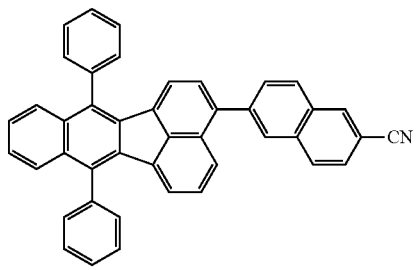
ET 1-45
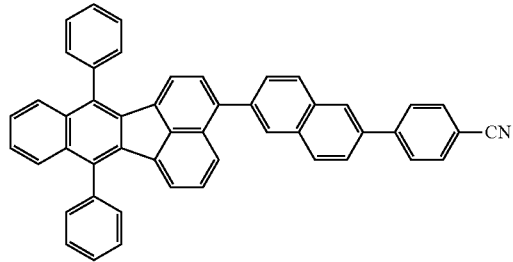
ET 1-46
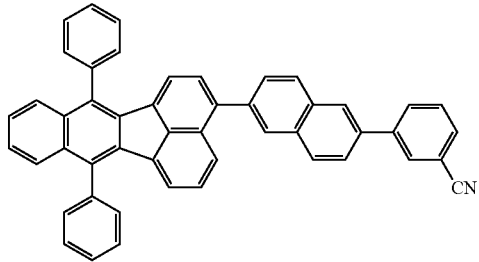
ET 1-47
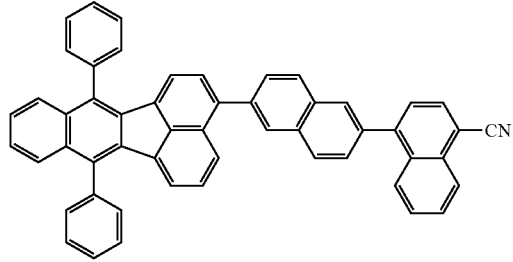
ET 1-48
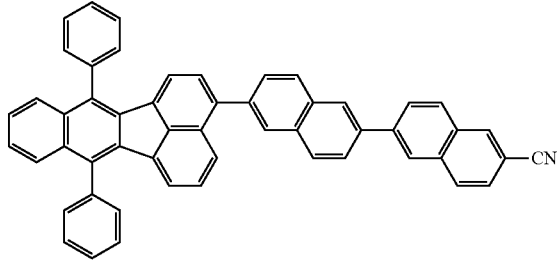

ET 1-49
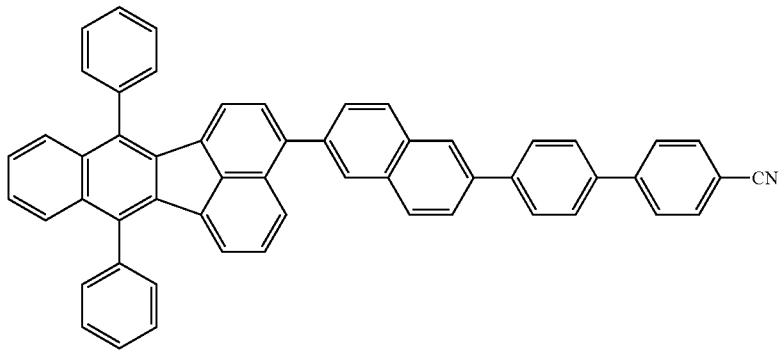
ET 1-50
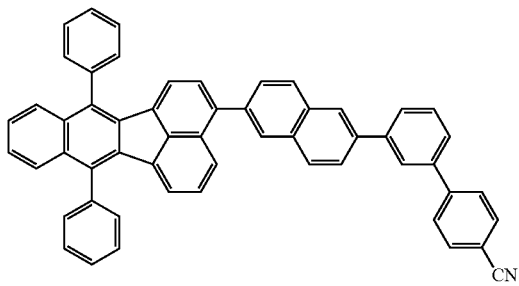
ET 1-51
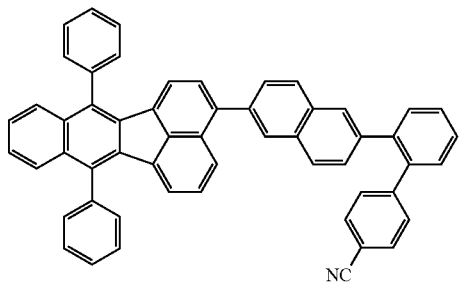
ET 1-52
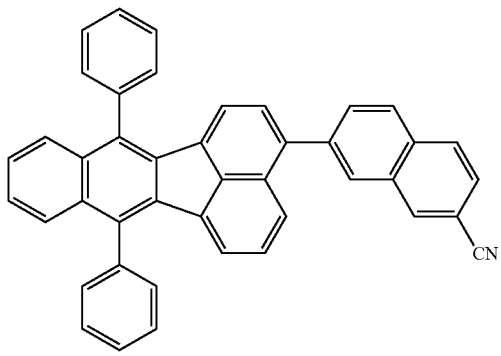
ET 1-53
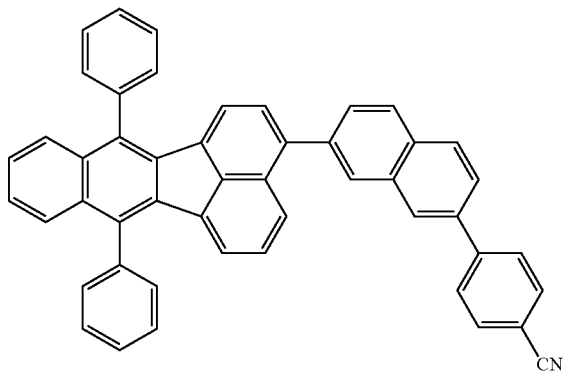
ET 1-54
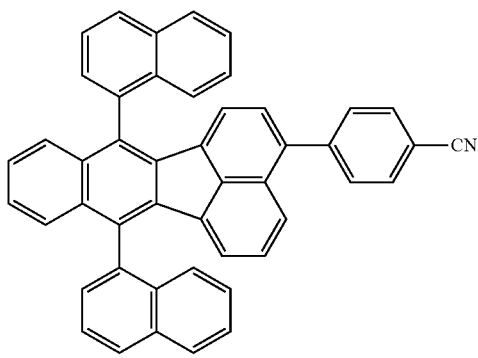
ET 1-55
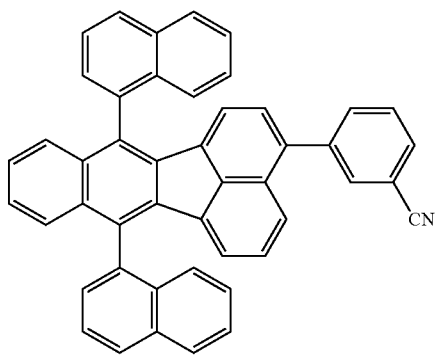

-continued
ET 1-56
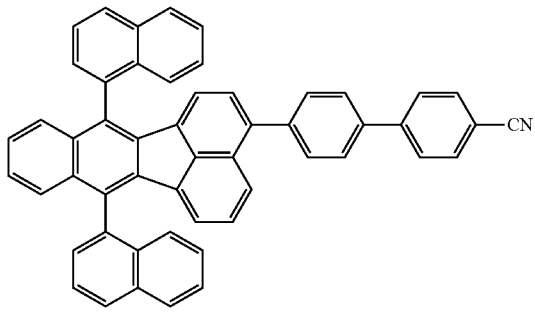
ET 1-57
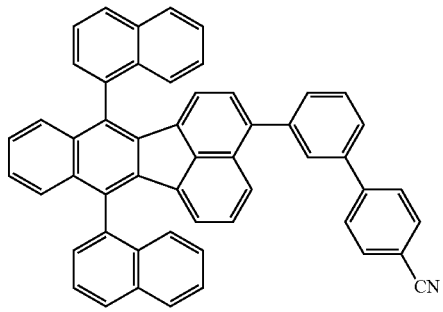
ET 1-58
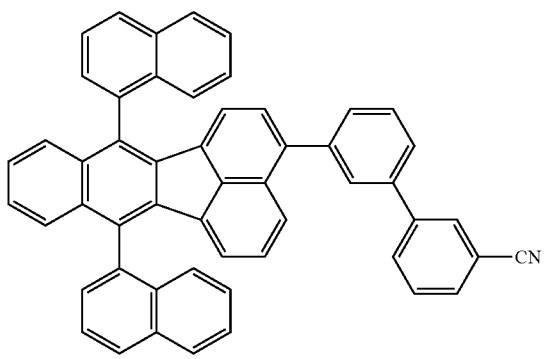
ET 1-59
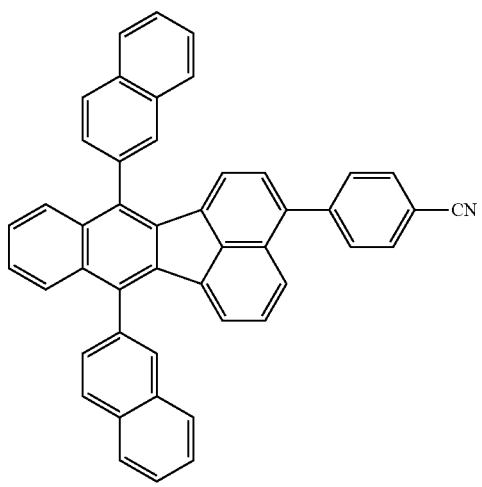
ET 1-60
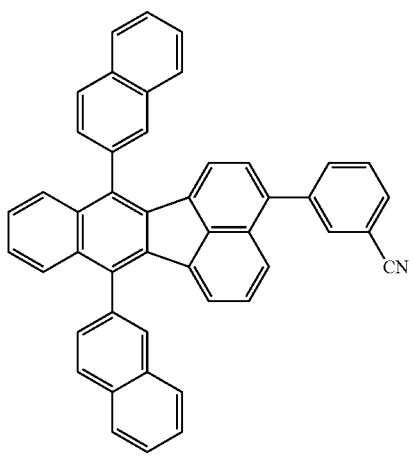
ET 1-61
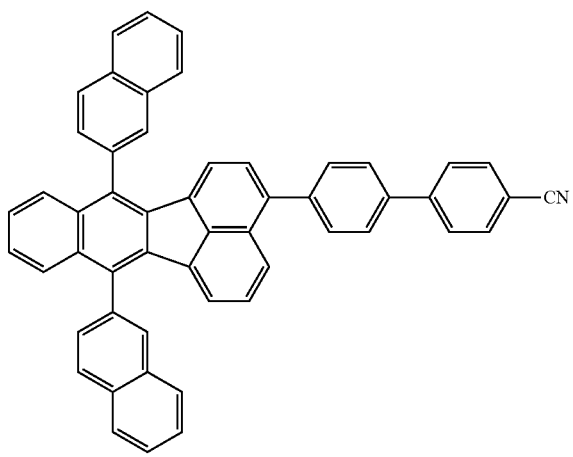

-continued
ET 1-62
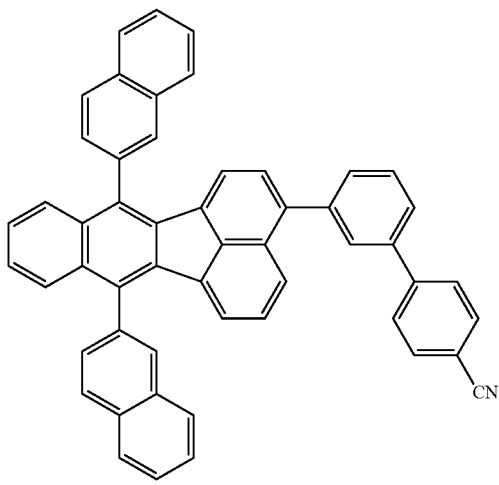
ET 1-63
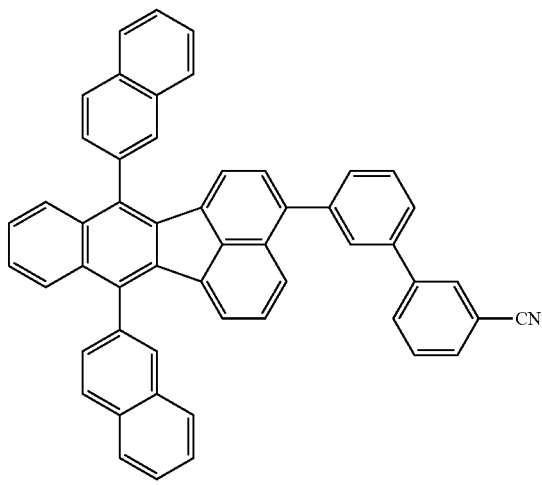
ET 1-64
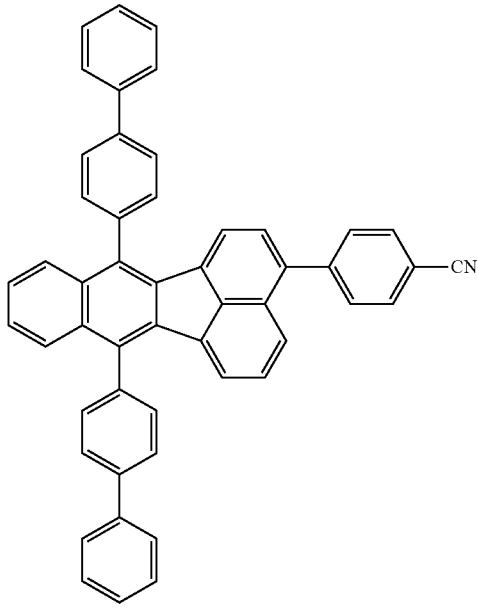
ET 1-65
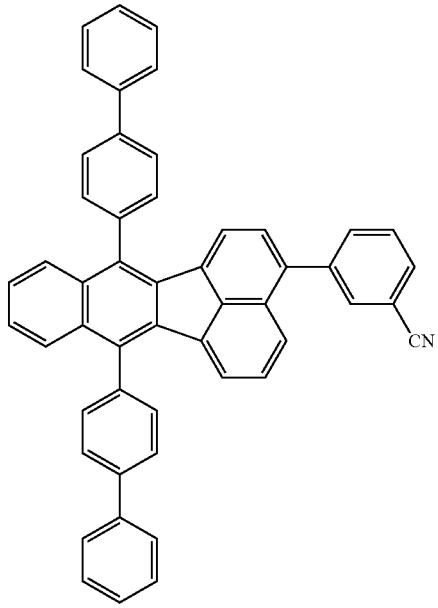
ET 1-66
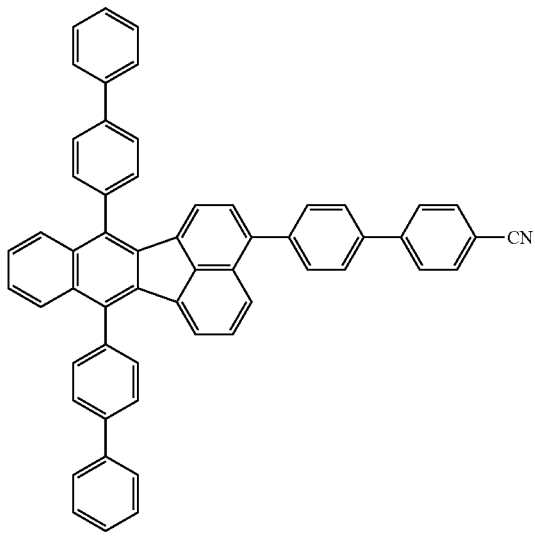
ET 1-67
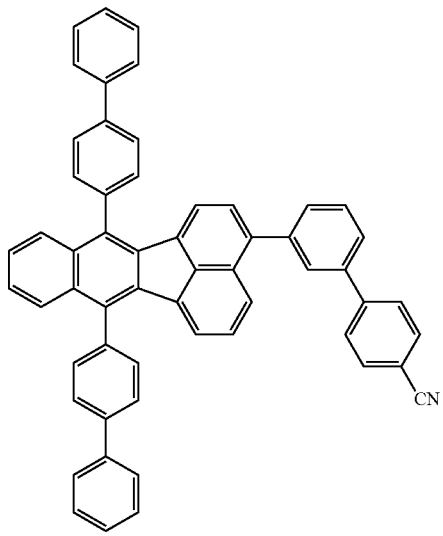

ET 1-68
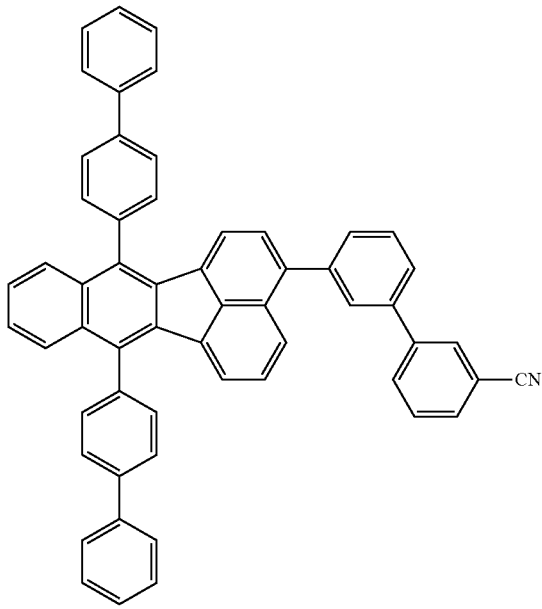
ET 1-69
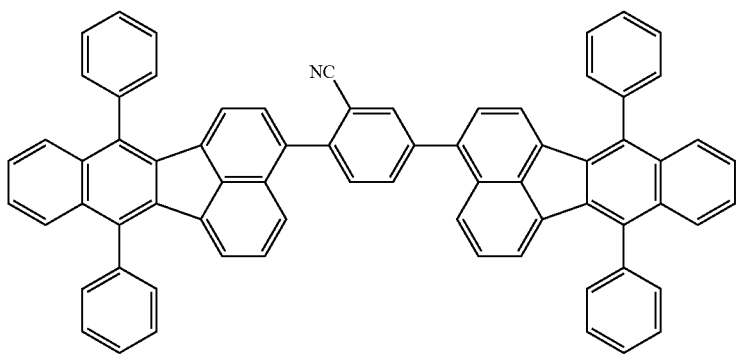
ET 1-70
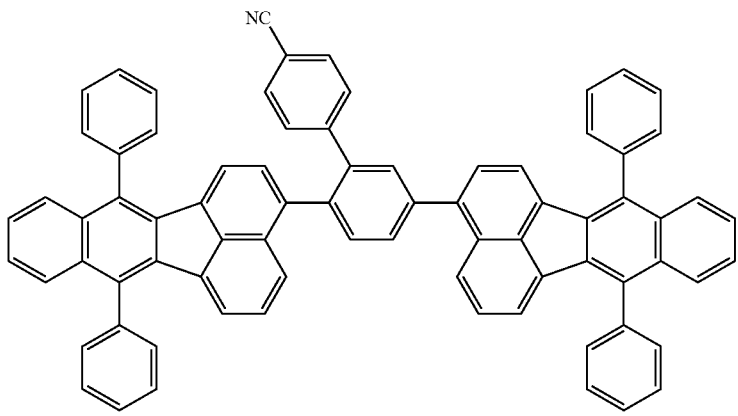

ET 1-71

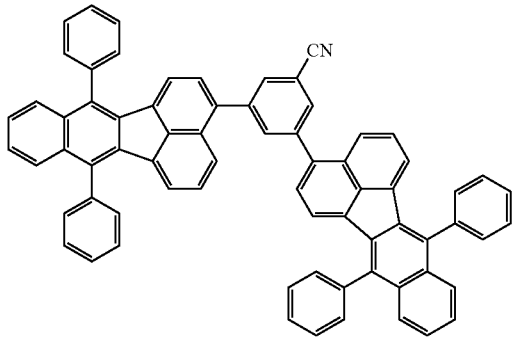

ET 1-72

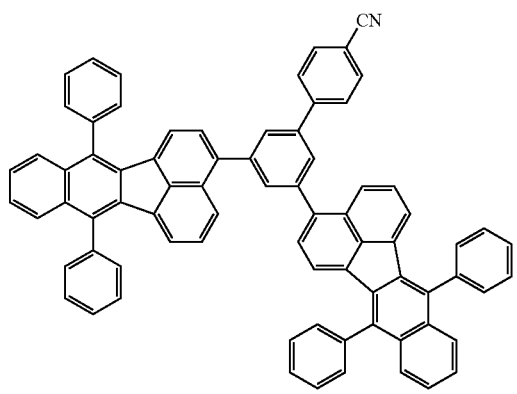

The compound used in the invention that includes a cyano group and an aromatic ring group is an electron-transporting material compound. The compound shown by the formula (1) that includes a benzofluoranthene skeleton may suitably be used as a triplet energy blocking material for the following reason.

A benzofluoranthene skeleton has high triplet energy as compared with an anthracene skeleton that is normally used as a blue fluorescent material, and exhibits a high triplet exciton confinement effect. Therefore, it is considered that a triplet-triplet fusion (TTF) phenomenon can be promoted by utilizing the compound shown by the formula (1) that includes a benzofluoranthene skeleton as a material for a blocking layer of an organic EL device that is adjacent to an emitting layer, for example. A benzofluoranthene skeleton improves molecular stacking within a thin film due to high planarity, so that the electron-transporting capability is improved. This may make it possible to promote injection of electrons into the emitting layer and improve the recombination efficiency in the emitting layer, so that the TTF phenomenon may efficiently occur.

The compounds shown by the following formulas (2) to (12) are also preferable as the compound used in the invention that includes a cyano group and an aromatic ring group in addition to the compound shown by the formula (1) that includes a benzofluoranthene skeleton.

Note that a, b, c, $L_1$, and $Ar_1$ in the formulas (2) to (12) are the same as defined for the formula (1).

$R_{21}$ to $R_{30}$, $R_{31}$ to $R_{40}$, $R_{41}$ to $R_{50}$, $R_{51}$ to $R_{60}$, $R_{61}$ to $R_{72}$, $R_{73}$ to $R_{86}$, $R_{87}$ to $R_{94}$, $R_{95}$ to $R_{104}$, $R_{105}$ to $R_{114}$, $R_{115}$ to $R_{124}$, and $R_{125}$ to $R_{134}$ are respectively the same as defined for $R_1$ to $R_{12}$ in the formula (1).

Compound that includes anthracene skeleton

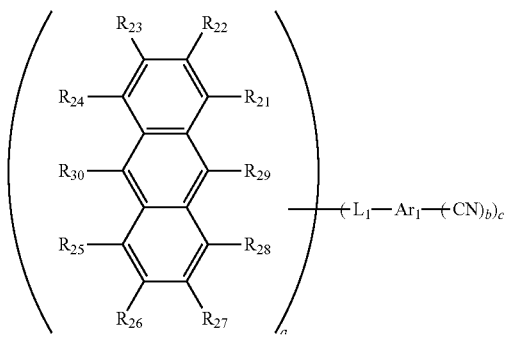

(2)

It is preferable that one, two, or three of $R_{22}$, $R_{23}$, $R_{26}$, $R_{27}$, $R_{29}$, and $R_{30}$ be bonded to $L_1$. It is more preferable that either or both of $R_{29}$ and $R_{30}$ be bonded to $L_1$. When a in the formula (2) is an integer equal to or larger than 2, a plurality of anthracene skeletons may be either identical or different. When c is an integer equal to or larger than 2, a plurality of $L_1$ and a plurality of cyanoaryl groups ($Ar_1$—$(CN)_b$) may respectively be either identical or different.

Compound that includes pyrene skeleton

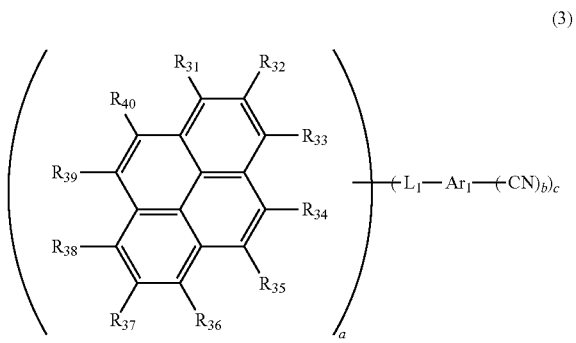

(3)

It is preferable that one, two, or three of $R_{31}$, $R_{33}$, $R_{36}$, and $R_{38}$ be bonded to $L_1$. It is more preferable that one or two of $R_{31}$, $R_{33}$, $R_{36}$, and $R_{38}$ be bonded to $L_1$. When a in the formula (3) is an integer equal to or larger than 2, a plurality of pyrene skeletons may be either identical or different. When c is an integer equal to or larger than 2, a plurality of $L_1$ and a plurality of cyanoaryl groups ($Ar_1$—$(CN)_b$) may respectively be either identical or different.

Compound that includes fluoranthene skeleton

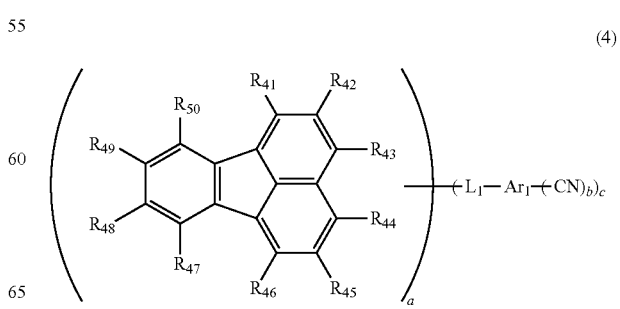

(4)

It is preferable that one or two of $R_{43}$, $R_{44}$, $R_{47}$, $R_{48}$, $R_{49}$, and $R_{50}$ be bonded to $L_1$. It is more preferable that $R_{43}$ or $R_{44}$ be bonded to $L_1$. When a in the formula (4) is an integer equal to or larger than 2, a plurality of fluoranthene skeletons may be either identical or different. When c is an integer equal to or larger than 2, a plurality of $L_1$ and a plurality of cyanoaryl groups ($Ar_1$—$(CN)_b$) may respectively be either identical or different.

Compound that includes phenanthrene skeleton

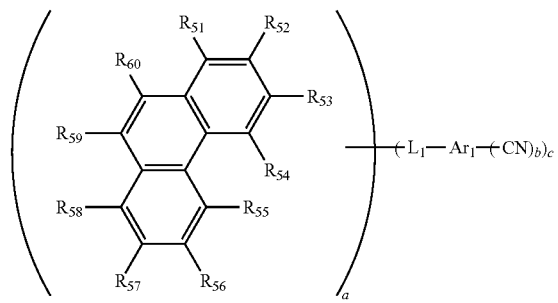

(5)

It is preferable that one or two of $R_{51}$ to $R_{60}$ be bonded to $L_1$. It is more preferable that $R_{59}$ or $R_{60}$ be bonded to $L_1$. When a in the formula (5) is an integer equal to or larger than 2, a plurality of phenanthrene skeletons may be either identical or different. When c is an integer equal to or larger than 2, a plurality of $L_1$ and a plurality of cyanoaryl groups ($Ar_1$—$(CN)_b$) may respectively be either identical or different.

Compound that includes chrysene skeleton

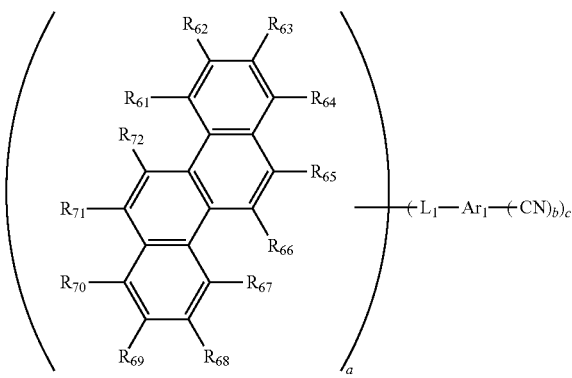

(6)

It is preferable that either or both of $R_{65}$ and $R_{71}$ be bonded to $L_1$. When a in the formula (6) is an integer equal to or larger than 2, a plurality of chrysene skeletons may be either identical or different. When c is an integer equal to or larger than 2, a plurality of $L_1$ and a plurality of cyanoaryl groups ($Ar_1$—$(CN)_b$) may respectively be either identical or different.

The compound shown by the formula (6) that includes a chrysene skeleton is preferably a compound shown by the following formula (7) that has a structure in which $R_{71}$ and $R_{72}$ bond to form a benzene ring.

Compound that includes benzochrysene skeleton

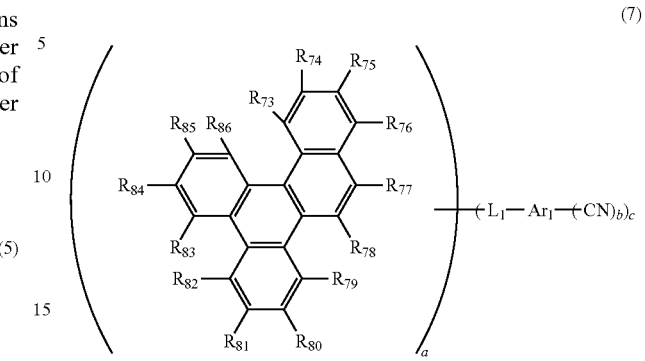

(7)

It is preferable that $R_{77}$ be bonded to $L_1$. When a in the formula (7) is an integer equal to or larger than 2, a plurality of benzochrysene skeletons may be either identical or different. When c is an integer equal to or larger than 2, a plurality of $L_1$ and a plurality of cyanoaryl groups ($Ar_1$—$(CN)_b$) may respectively be either identical or different.

Compound that includes dibenzofuran skeleton

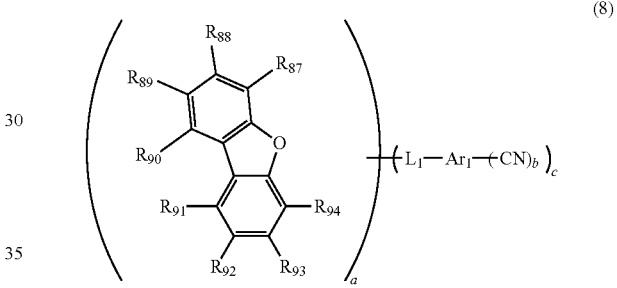

(8)

It is preferable that one or two of $R_{87}$, $R_{89}$, $R_{92}$, and $R_{94}$ be bonded to $L_1$. When a in the formula (8) is an integer equal to or larger than 2, a plurality of dibenzofuran skeletons may be either identical or different. When c is an integer equal to or larger than 2, a plurality of $L_1$ and a plurality of cyanoaryl groups ($Ar_1$—$(CN)_b$) may respectively be either identical or different.

Oxygen-containing fused aromatic ring compound shown by formula (9)

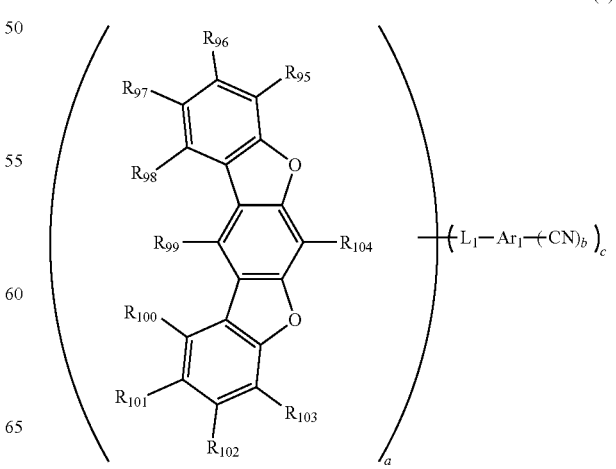

(9)

It is preferable that one, two, or three of $R_{97}$, $R_{101}$, and $R_{104}$ be bonded to $L_1$. It is more preferable that $R_{104}$ be bonded to $L_1$. When a in the formula (9) is an integer equal to or larger than 2, a plurality of ladder-type dibenzofuran skeletons may be either identical or different. When c is an integer equal to or larger than 2, a plurality of $L_1$ and a plurality of cyanoaryl groups ($Ar_1$—$(CN)_b$) may respectively be either identical or different.

Oxygen-containing fused aromatic ring compound shown by formula (10)

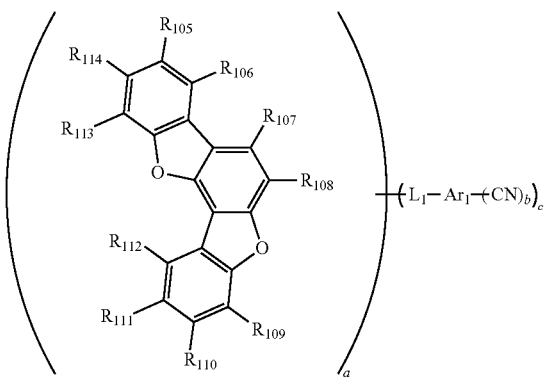

(10)

It is preferable that $R_{108}$ be bonded to $L_1$. When a in the formula (10) is an integer equal to or larger than 2, a plurality of ladder-type dibenzofuran skeletons may be either identical or different. When c is an integer equal to or larger than 2, a plurality of $L_1$ and a plurality of cyanoaryl groups ($Ar_1$—$(CN)_b$) may respectively be either identical or different.

Oxygen-containing fused aromatic ring compound shown by formula (11)

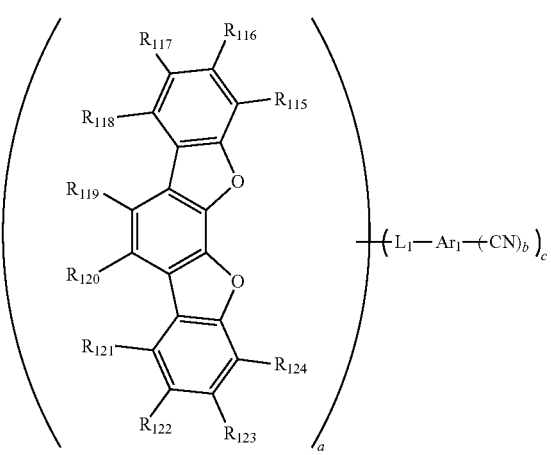

(11)

It is preferable that one or two of $R_{115}$, $R_{117}$, $R_{122}$, and $R_{124}$ be bonded to $L_1$. It is more preferable that either or both of $R_{117}$ and $R_{122}$ be bonded to $L_1$. When a in the formula (11) is an integer equal to or larger than 2, a plurality of ladder-type dibenzofuran skeletons may be either identical or different. When c is an integer equal to or larger than 2, a plurality of $L_1$ and a plurality of cyanoaryl groups ($Ar_1$—$(CN)_b$) may respectively be either identical or different.

Oxygen-containing fused aromatic ring compound shown by formula (12)

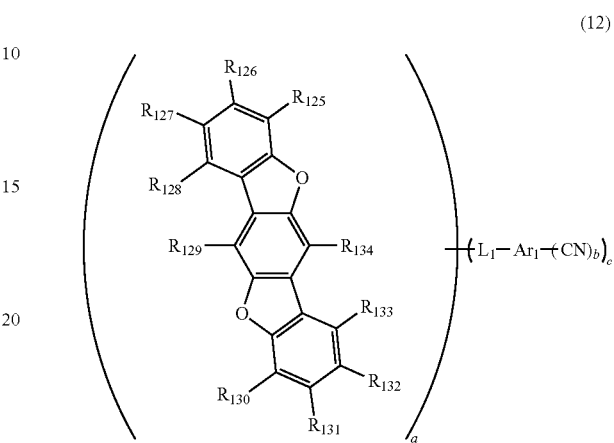

(12)

It is preferable that one or two of $R_{125}$, $R_{127}$, $R_{132}$, and $R_{134}$ be bonded to $L_1$. It is more preferable that either or both of $R_{127}$ and $R_{132}$ be bonded to $L_1$. When a in the formula (12) is an integer equal to or larger than 2, a plurality of ladder-type dibenzofuran skeletons may be either identical or different. When c is an integer equal to or larger than 2, a plurality of $L_1$ and a plurality of cyanoaryl groups ($Ar_1$—$(CN)_b$) may respectively be either identical or different.

The compound shown by the formula (1) is a known compound, and can be produced by a known method.

The compounds shown by the formulas (2) to (12) may be produced in accordance with the synthesis schemes described in the synthesis examples.

Specific examples of the compound shown by the formula (2) that includes an anthracene skeleton are shown below.

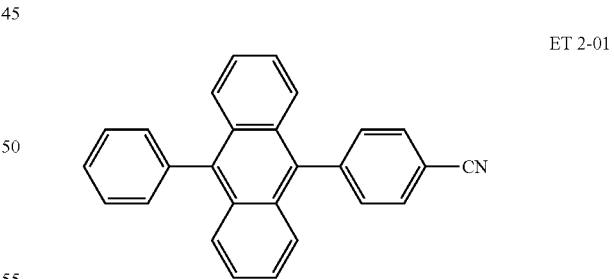

ET 2-01

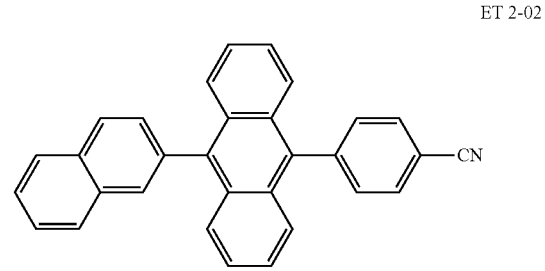

ET 2-02

ET 2-03
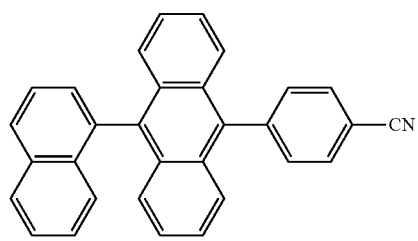
ET 2-04
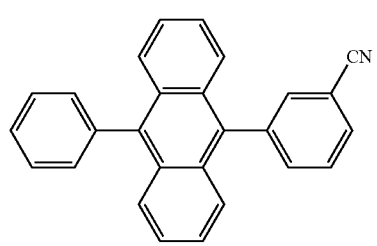
ET 2-05
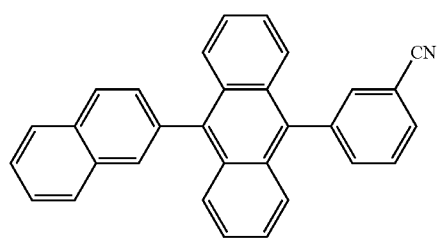
ET 2-06
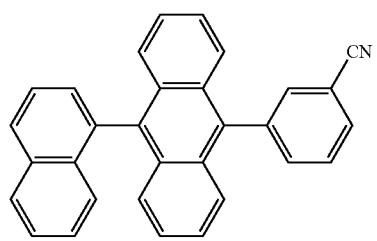
ET 2-07
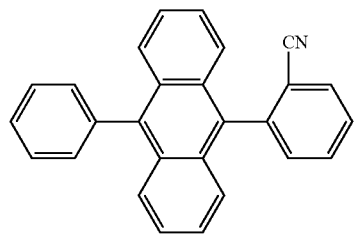
ET 2-08
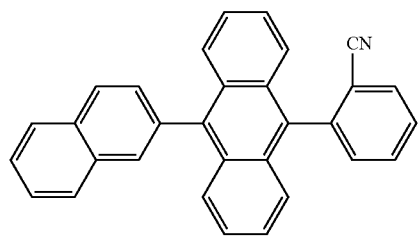
ET 2-09
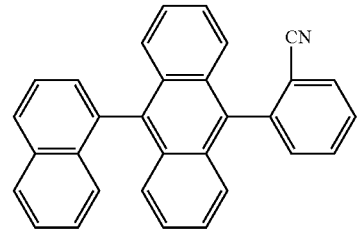
ET 2-10
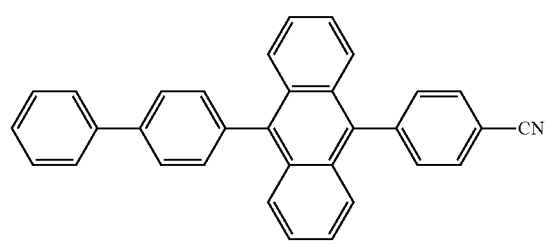
ET 2-11
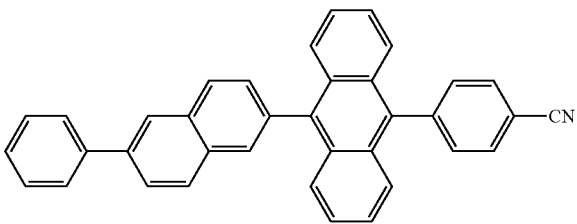
ET 2-12
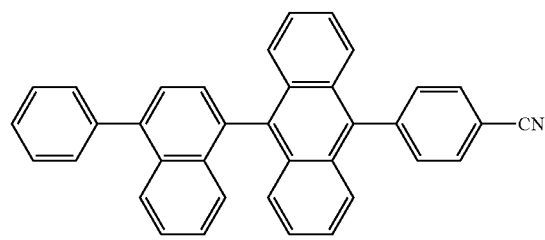
ET 2-13
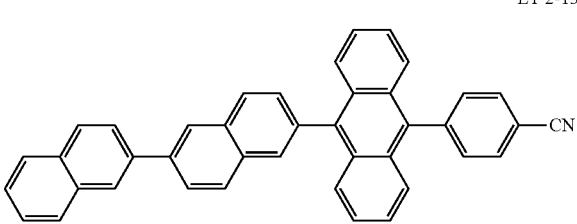
ET 2-14
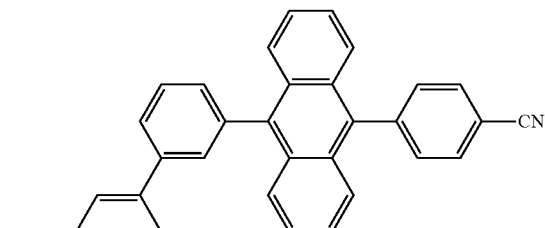

ET 2-15
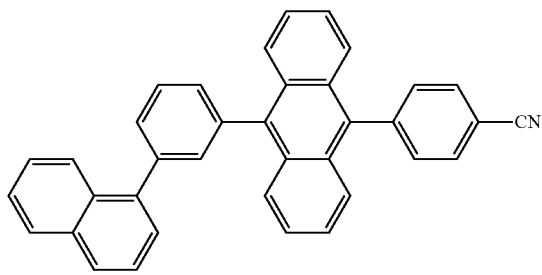
ET 2-16
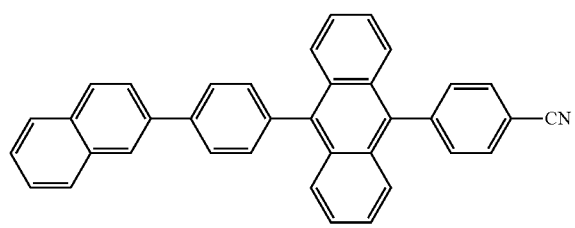
ET 2-17
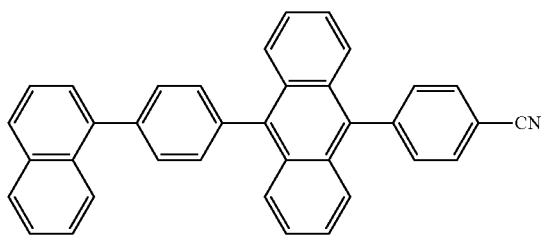
ET 2-18
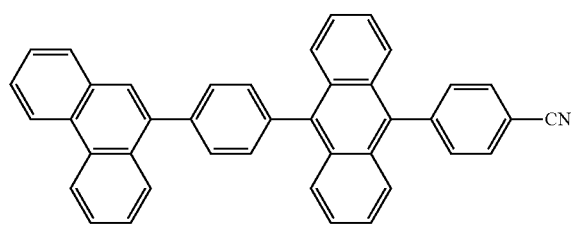
ET 2-19
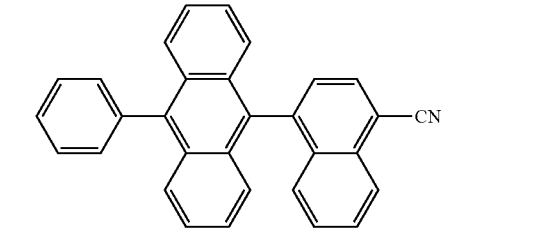
ET 2-20
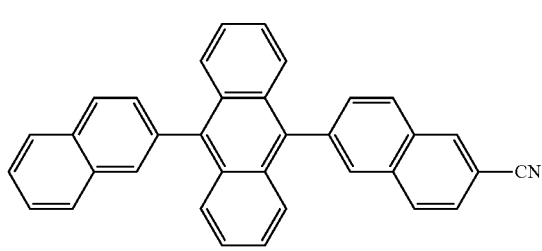
ET 2-21
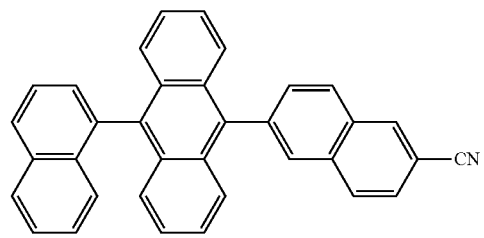
ET 2-22
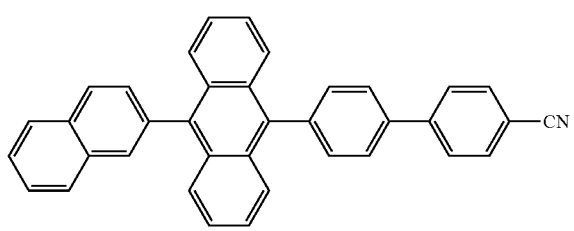
ET 2-23
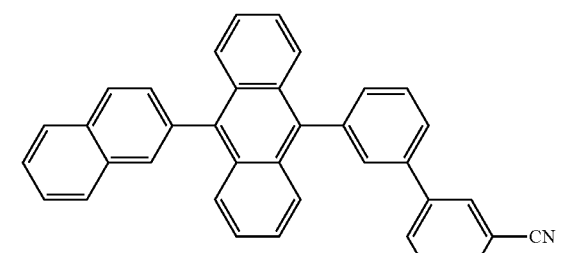
ET 2-24
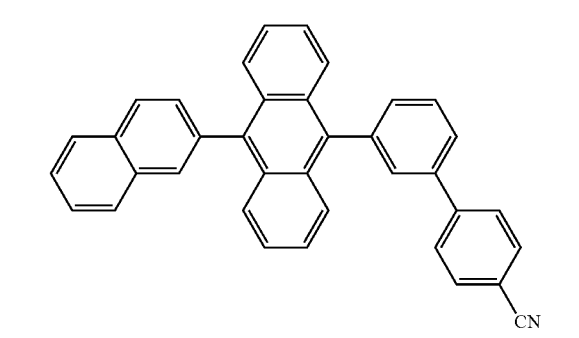
ET 2-25
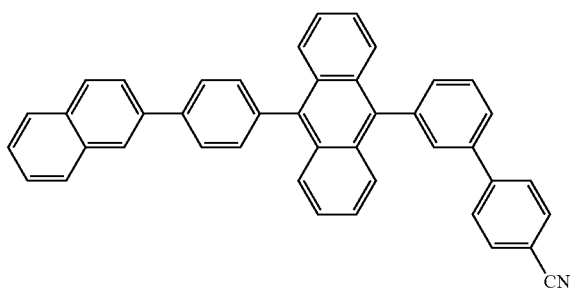

ET 2-26
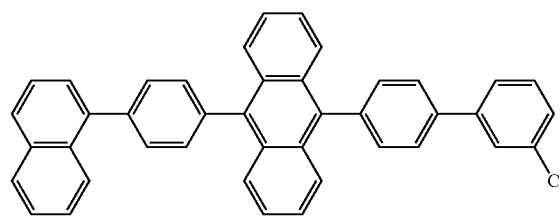
ET 2-27
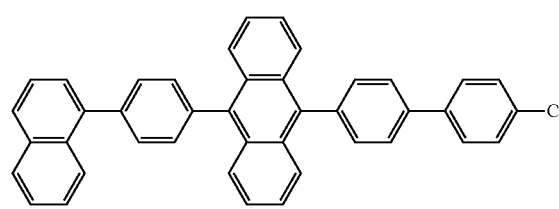
ET 2-28
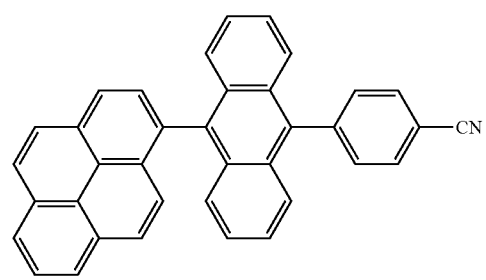
ET 2-29
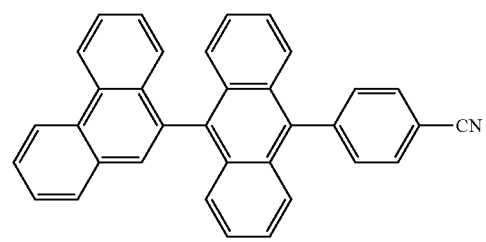
ET 2-30
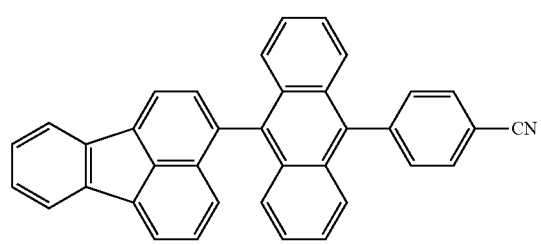
ET 2-31
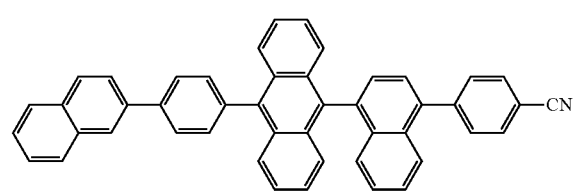
ET 2-32
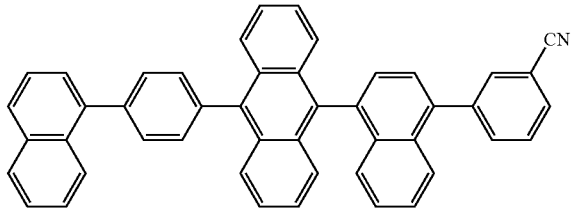
ET 2-33
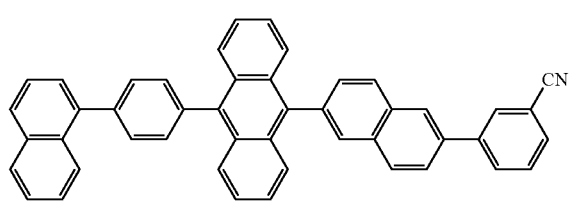
ET 2-34
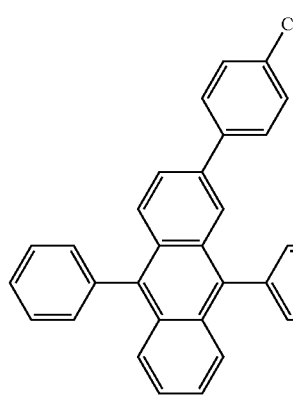
ET 2-35
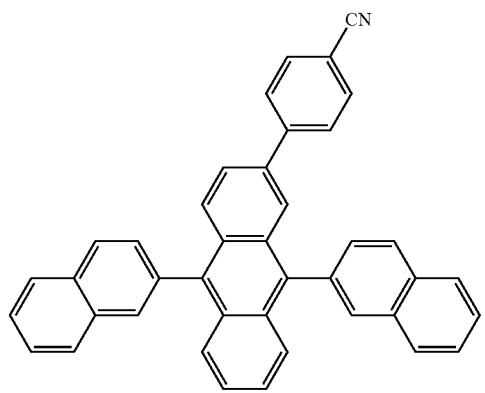
ET 2-36
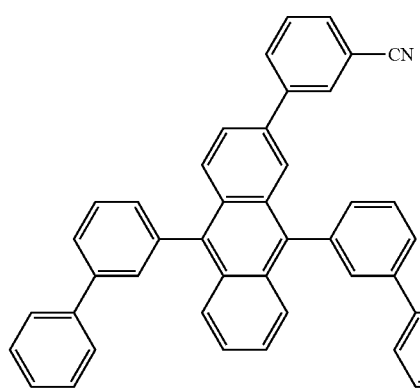

ET 2-37
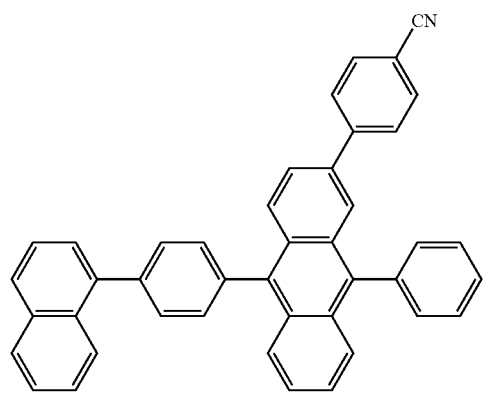
ET 2-38
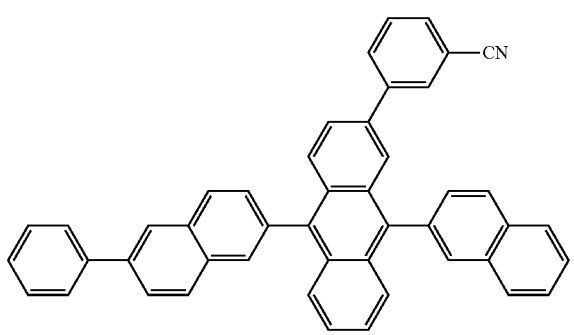
ET 2-39
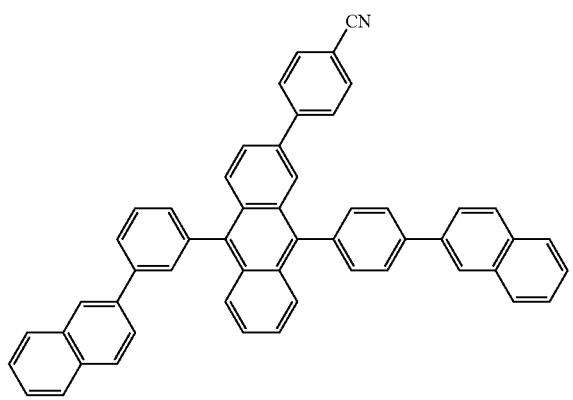
ET 2-40
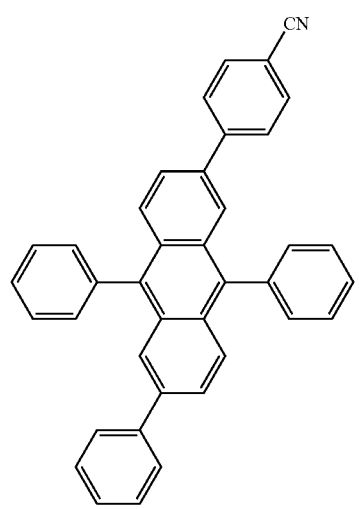
ET 2-41
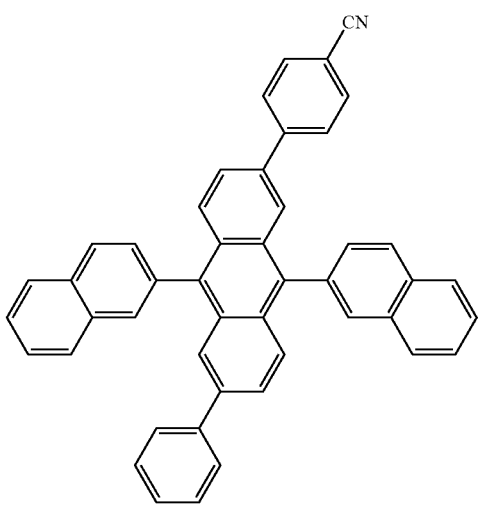
ET 2-42
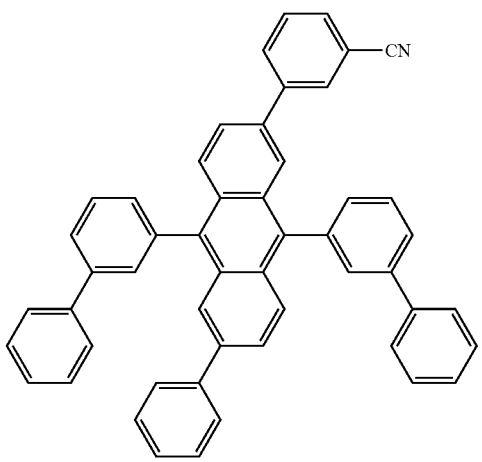
ET 2-43
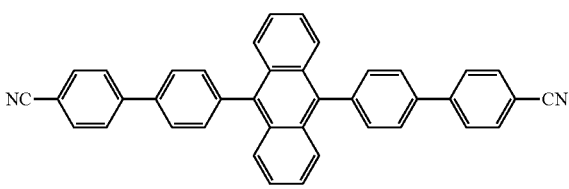
ET 2-44
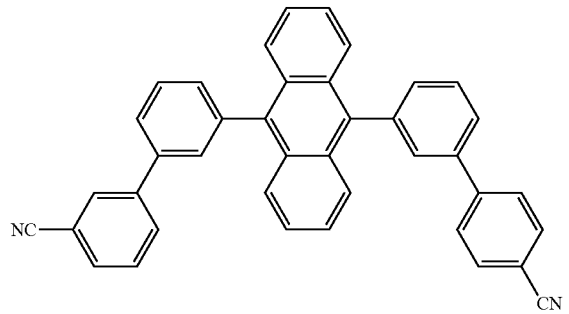

ET 2-45
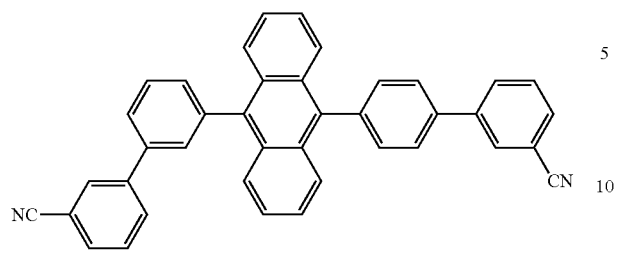
ET 2-48
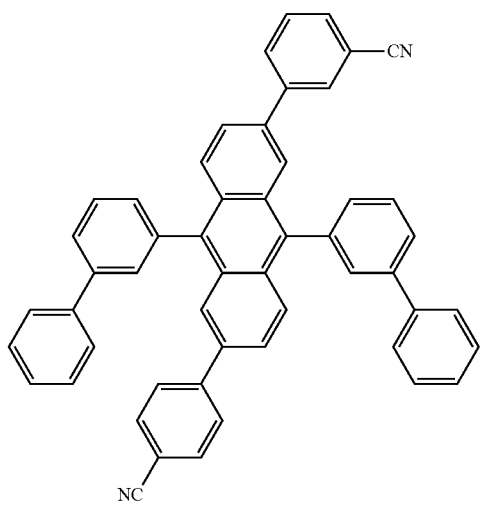
ET 2-46
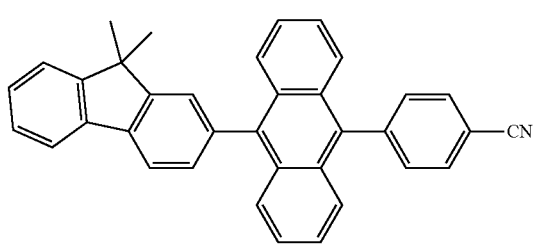
ET 2-49
ET 2-50
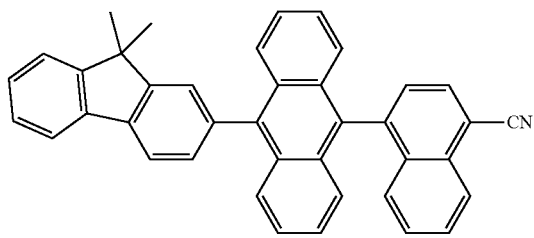
ET 2-51
ET 2-47
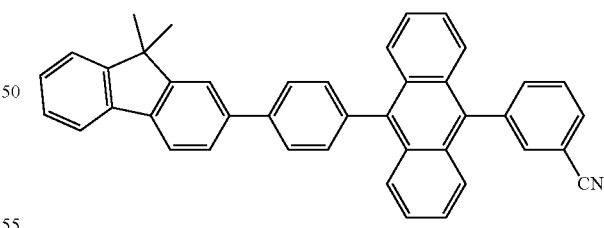
ET 2-52
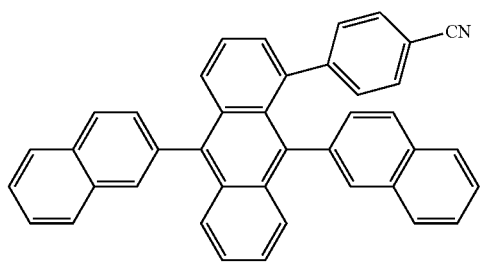

ET 2-53
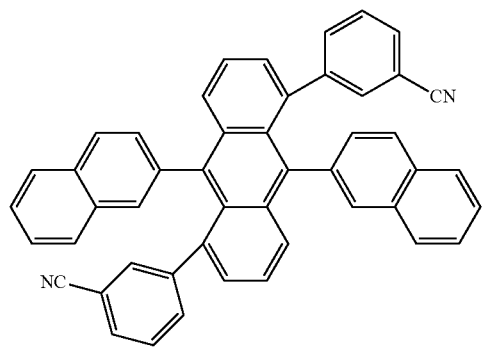
ET 3-04
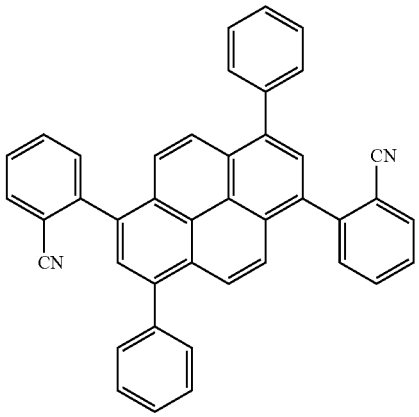
ET 2-54
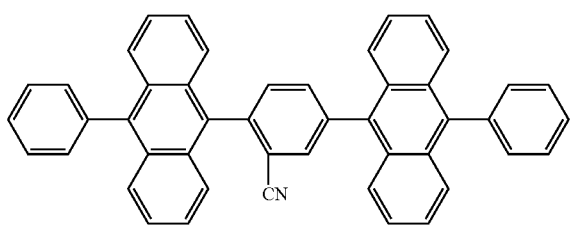
Specific examples of the compound shown by the formula (3) that includes a pyrene skeleton are shown below.
ET 3-01
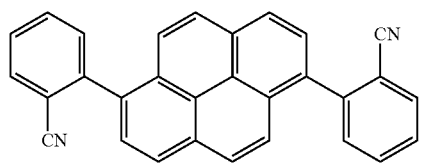
ET 3-05
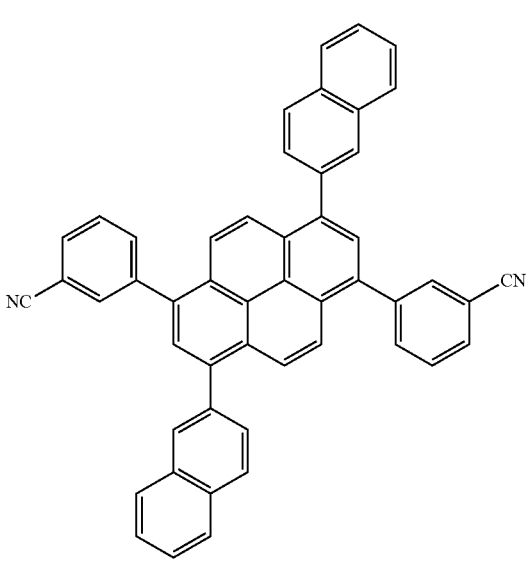
ET 3-02
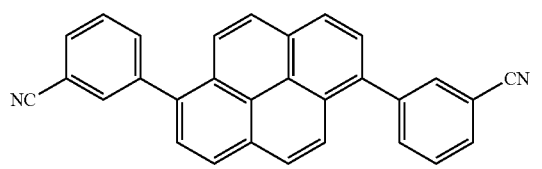
ET 3-03
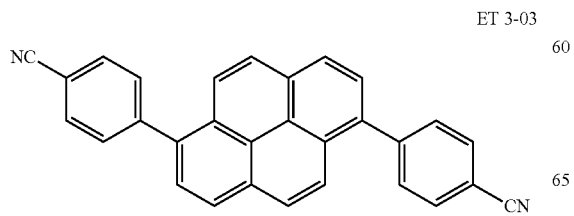
ET 3-06
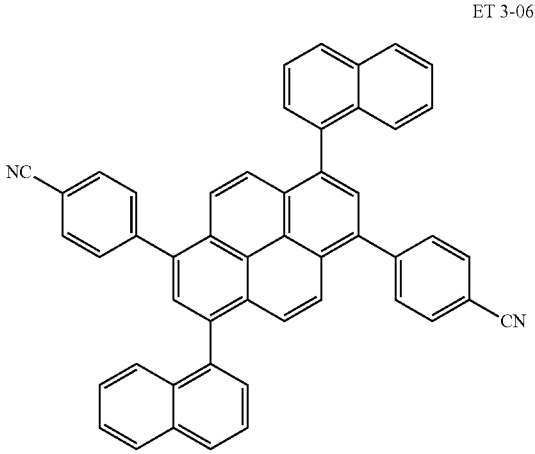

-continued
ET 3-07
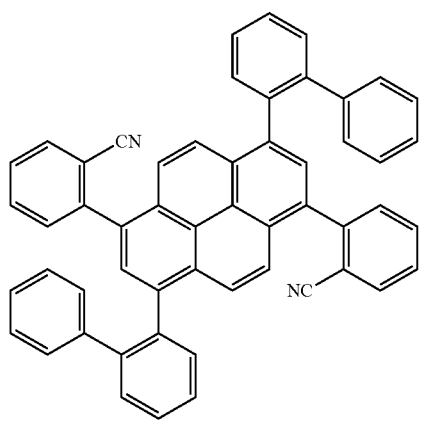
ET 3-08
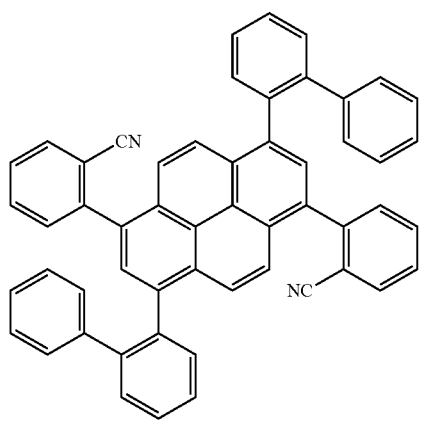
ET 3-09
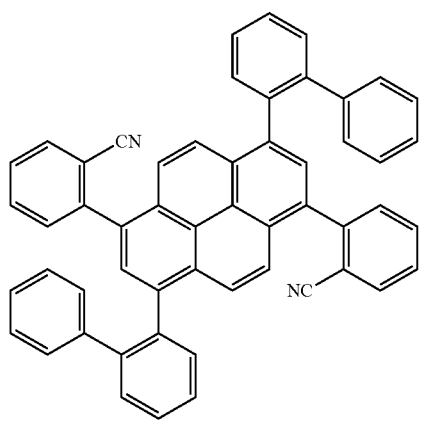
-continued
ET 3-10
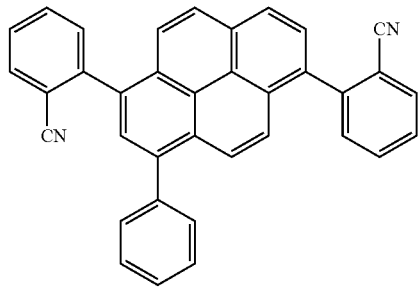
ET 3-11
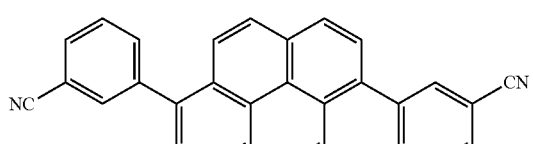
ET 3-12
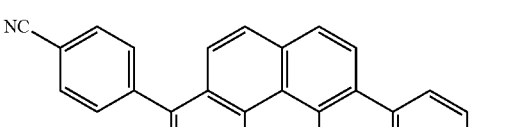
ET 3-13
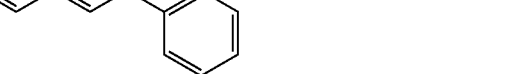
ET 3-14
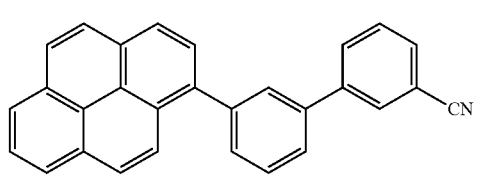
ET 3-15
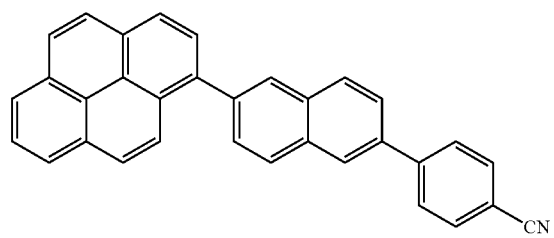

-continued
ET 3-16
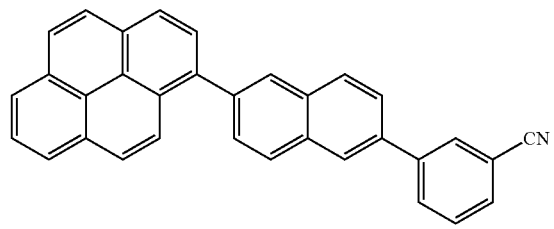
ET 3-17
ET 3-18
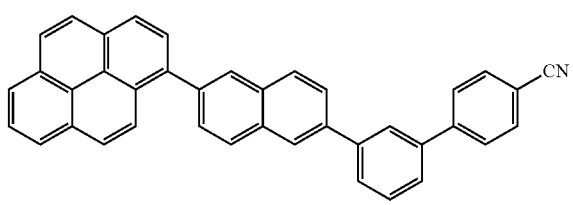
ET 3-19
ET 3-20
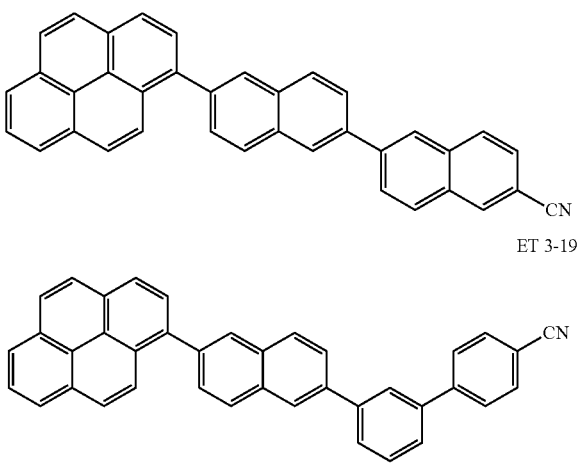
ET 3-21
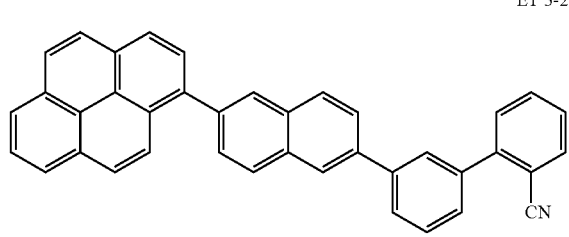
-continued
ET 3-22
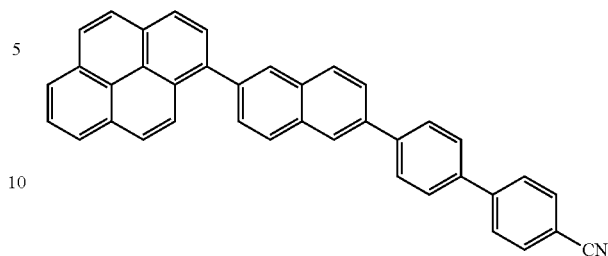
ET 3-23
ET 3-24
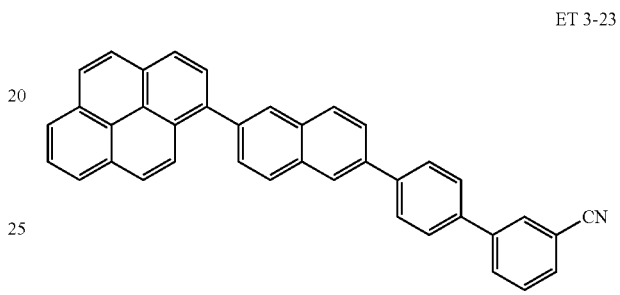
ET 3-25
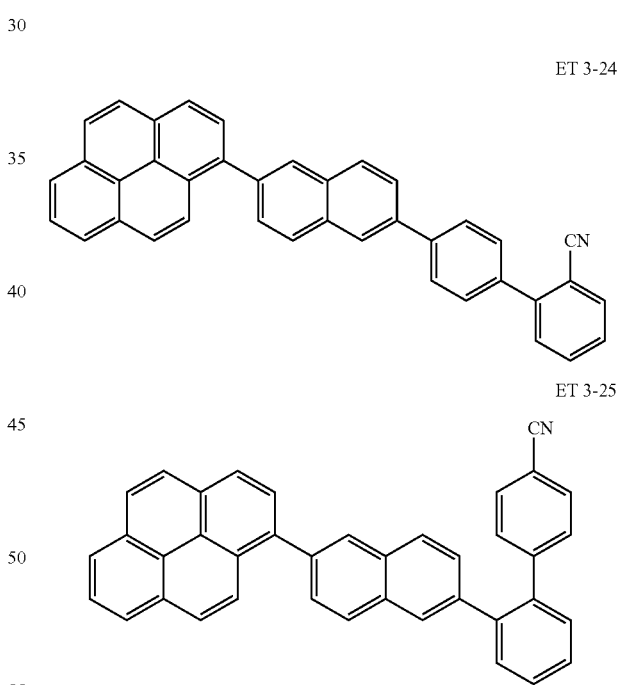
ET 3-26
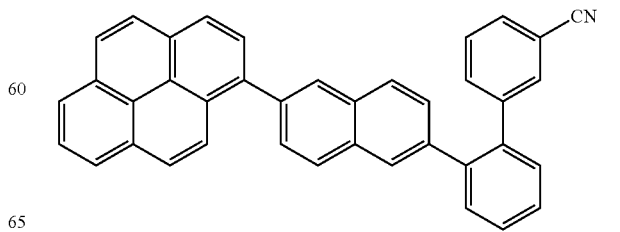

-continued
ET 3-27
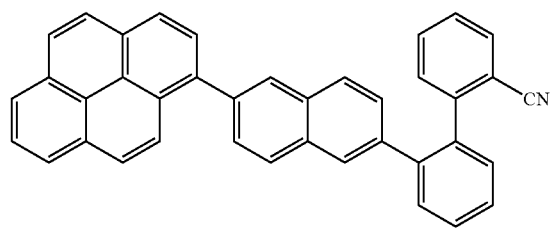
ET 3-28
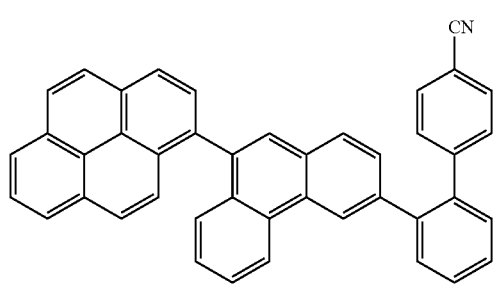
ET 3-29
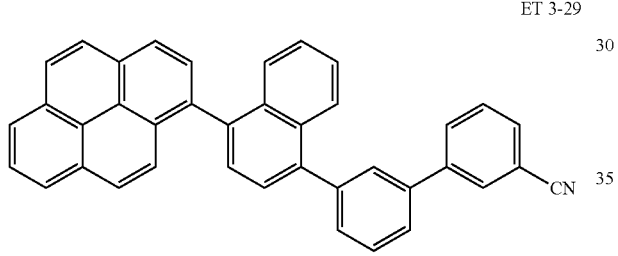
ET 3-30
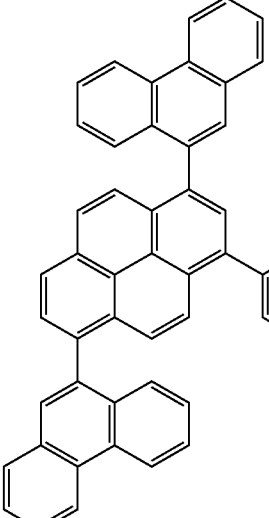
ET 3-31
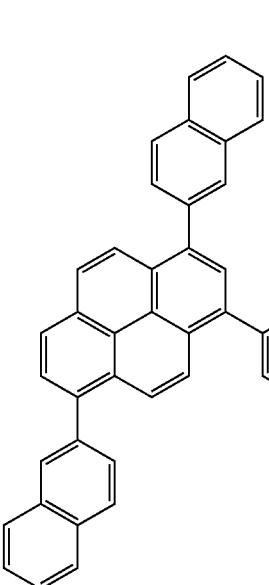
-continued
ET 3-32
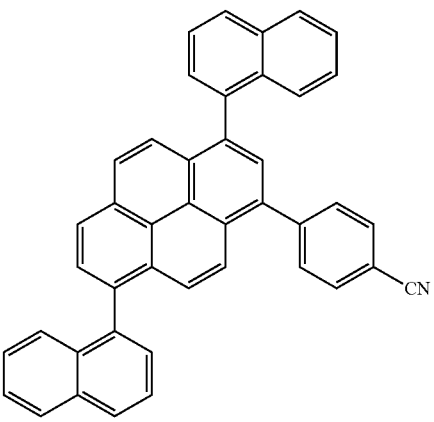
ET 3-33
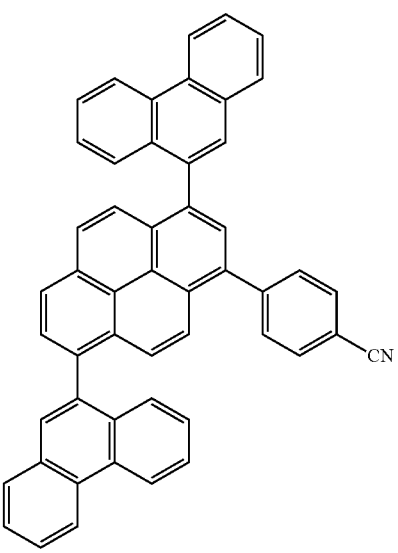
ET 3-34
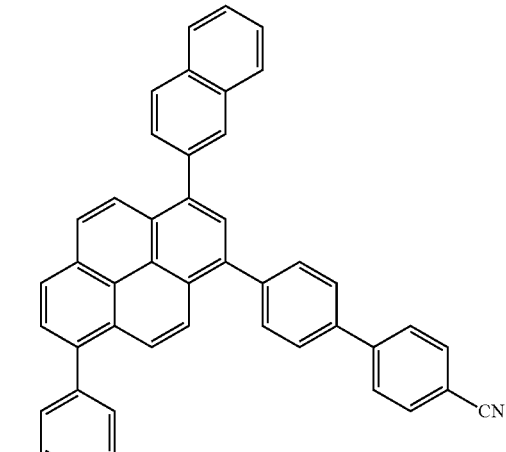

ET 3-35
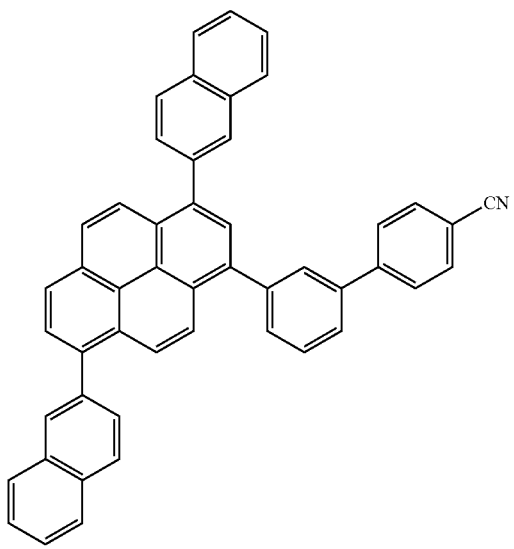
ET 3-36
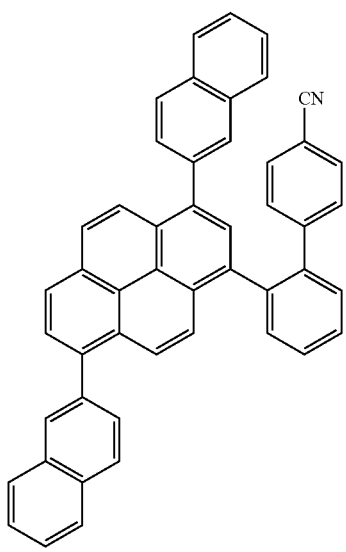
ET 3-37
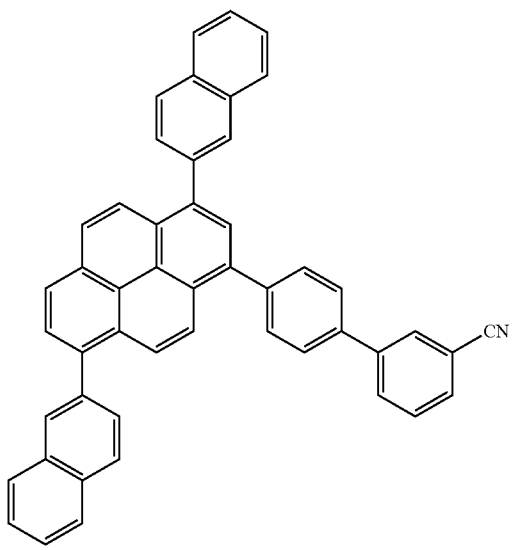
ET 3-38
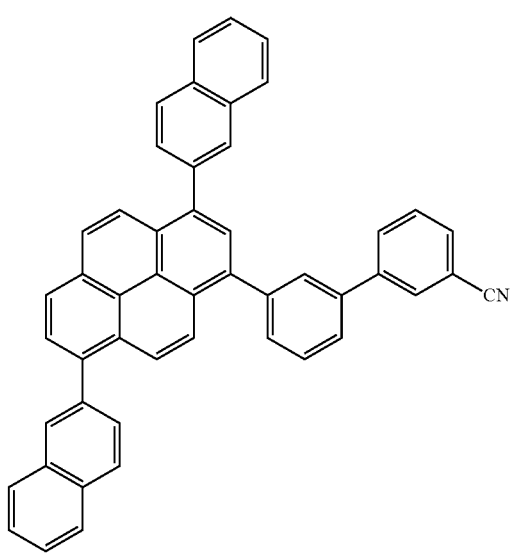
ET 3-39
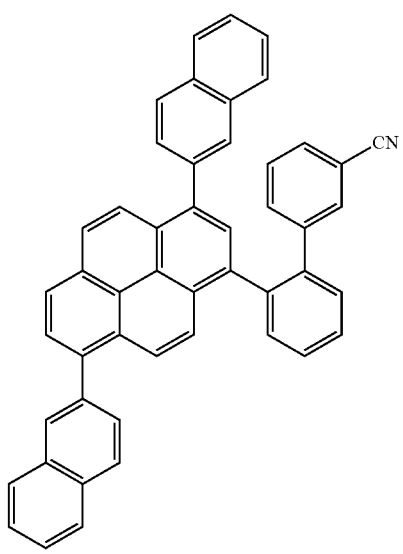
ET 3-40
ET 3-41
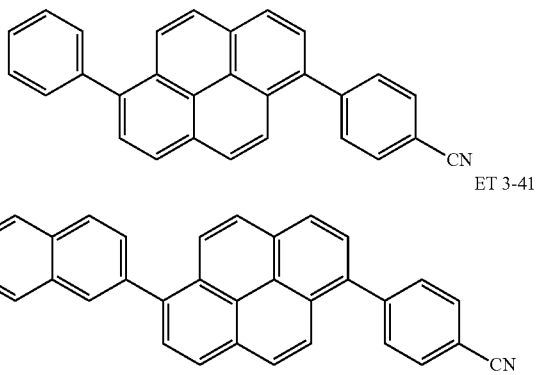

-continued
ET 3-42
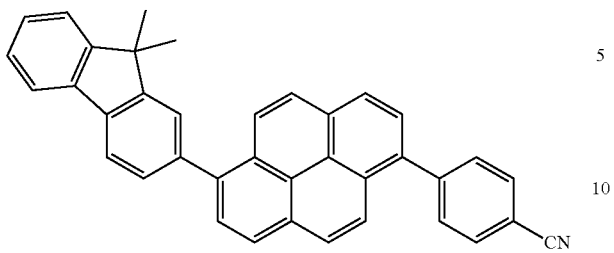
ET 3-43
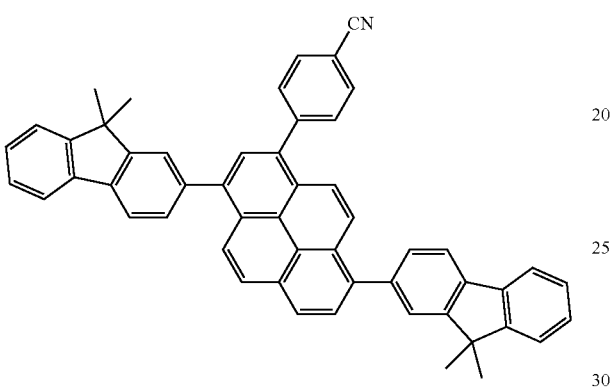
ET 3-44
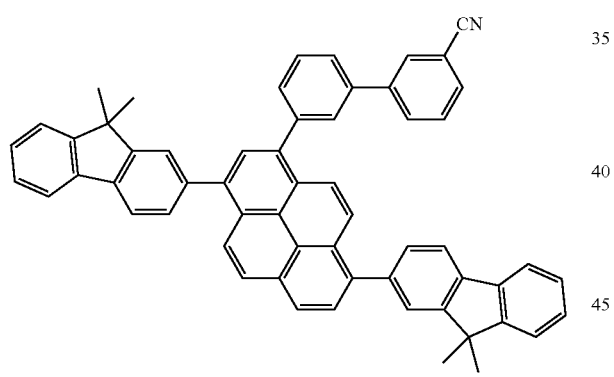
ET 3-45
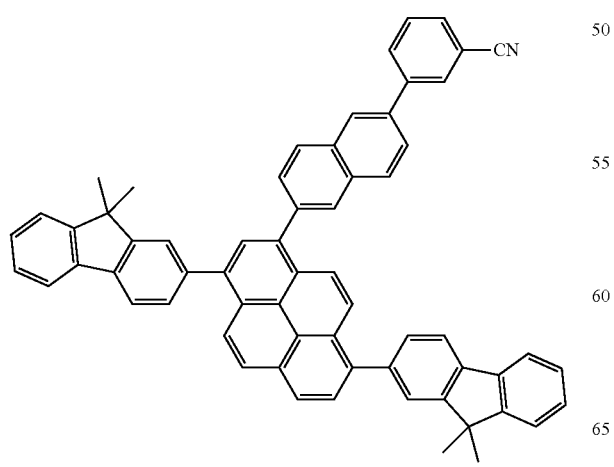
-continued
ET 3-46
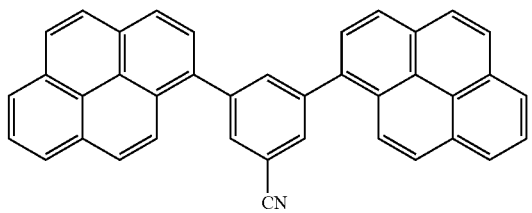
ET 3-47
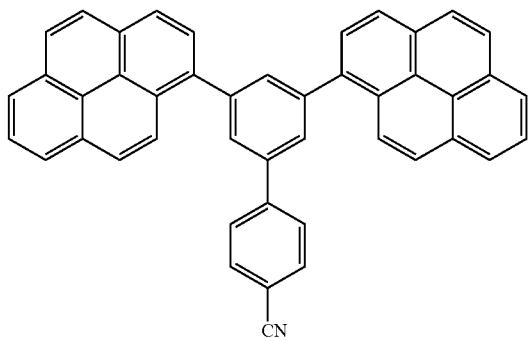
ET 3-48
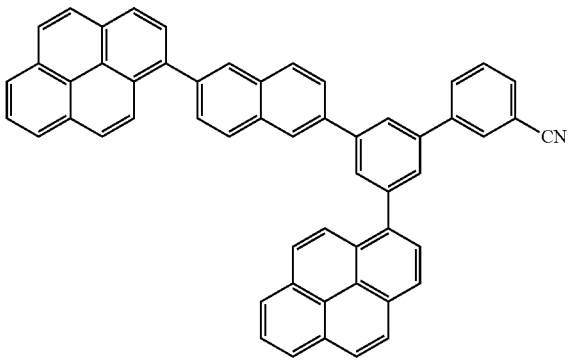
ET 3-49
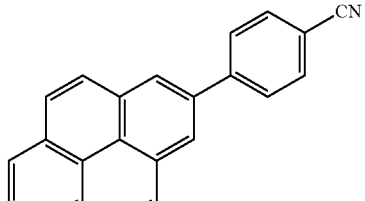
ET 3-50
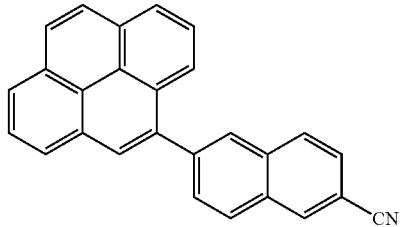

ET 3-51
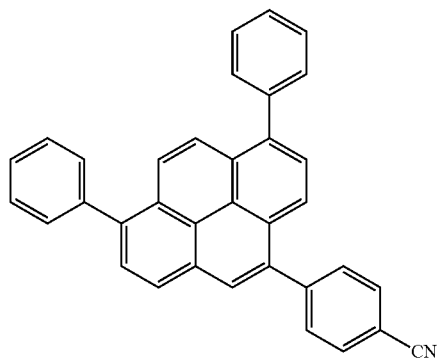
ET 3-52
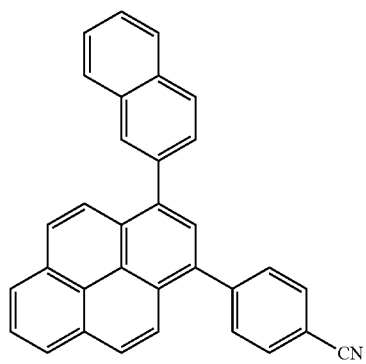
ET 3-53
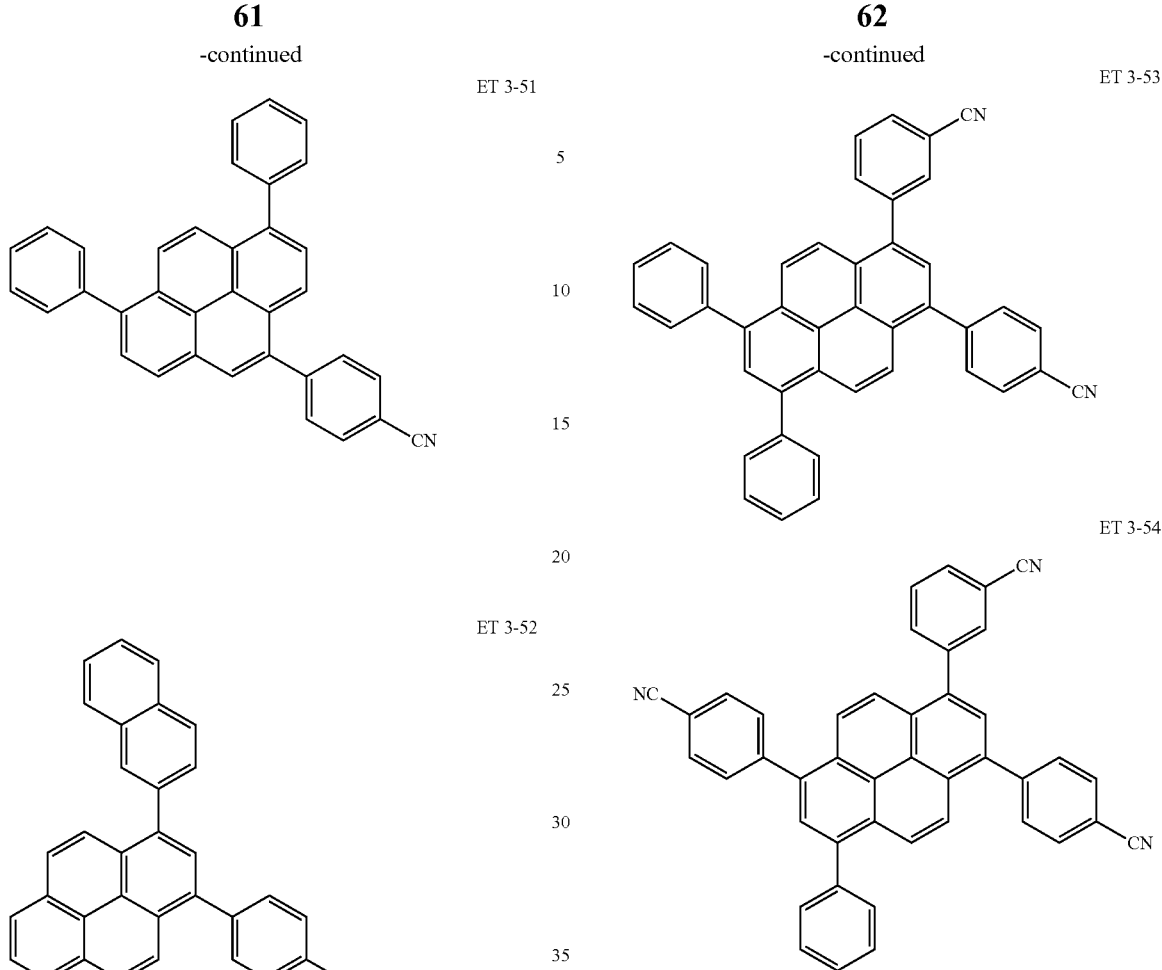
ET 3-54
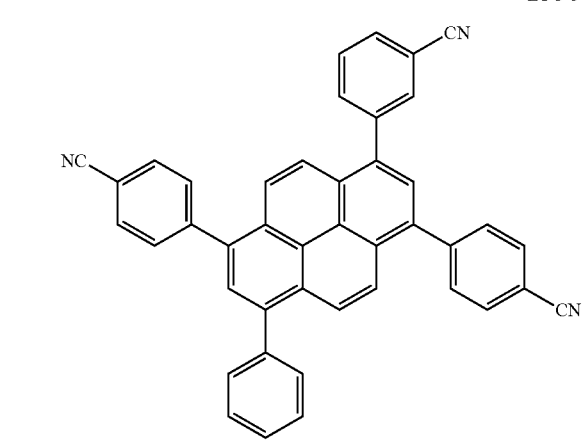
Specific examples of the compound shown by the formula (4) that includes a fluoranthene skeleton are shown below.
ET 4-01
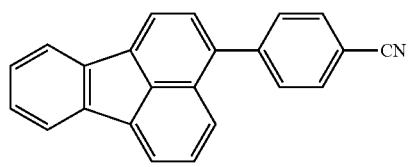
ET 4-02
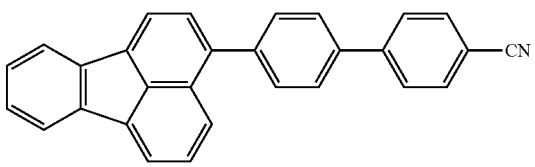
ET 4-03
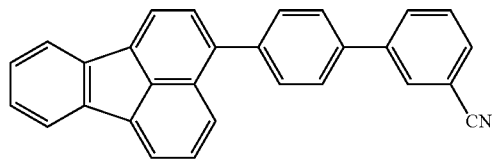
ET 4-04
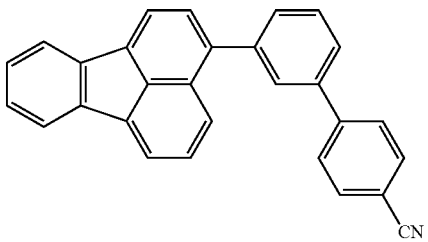
ET 4-05
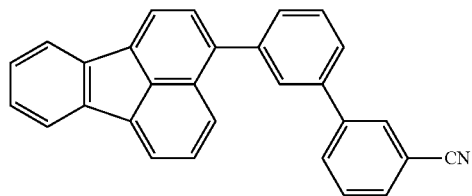
ET 4-06
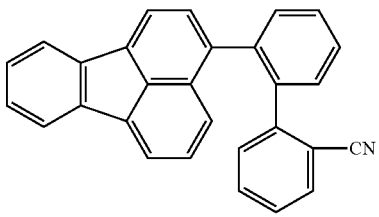

-continued
ET 4-07
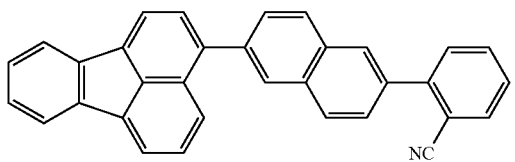
ET 4-08
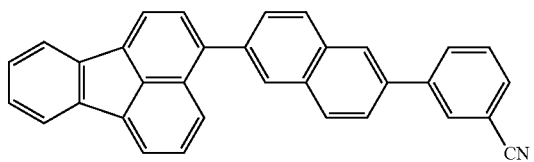
ET 4-09
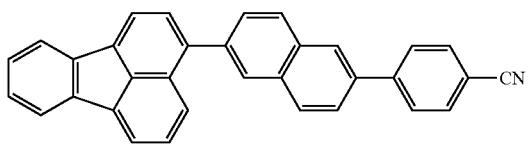
ET 4-10
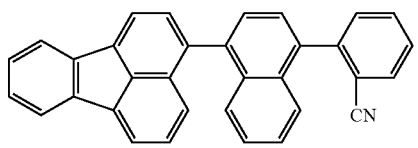
ET 4-11
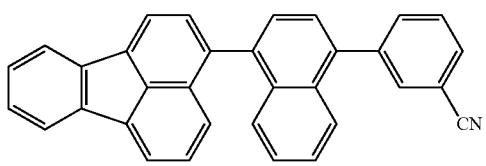
ET 4-12
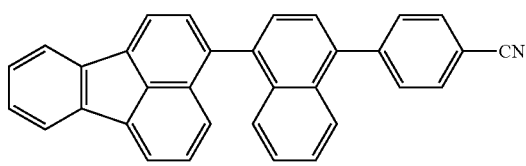
ET 4-13
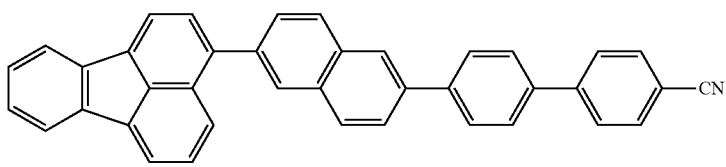
ET 4-14
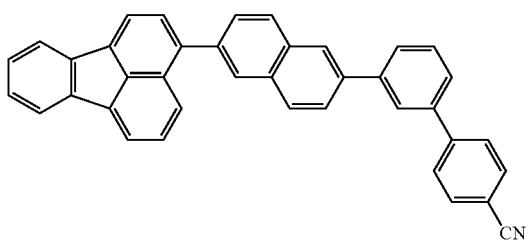
ET 4-15
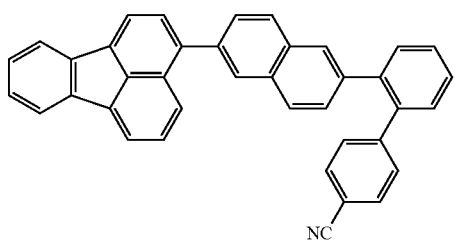
ET 4-16
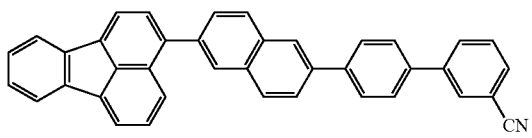
ET 4-17
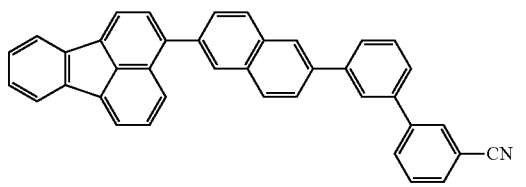
ET 4-18
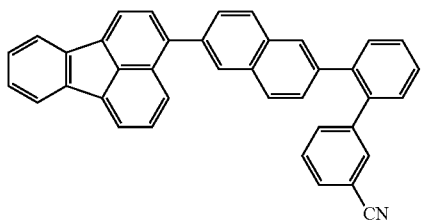
ET 4-19
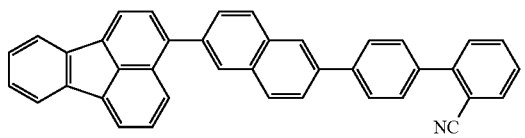

-continued
ET 4-20
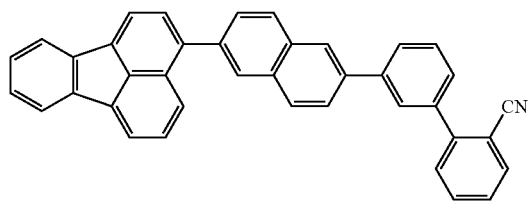
ET 4-21
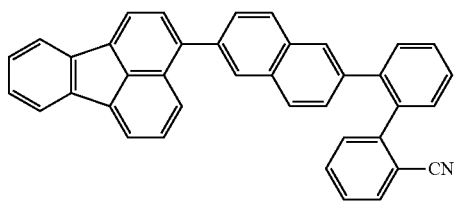
ET 4-22
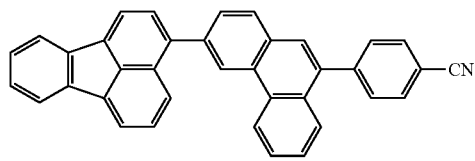
ET 4-23
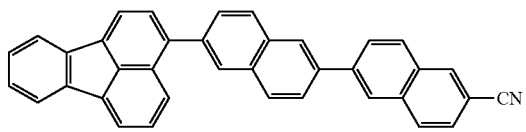
ET 4-24
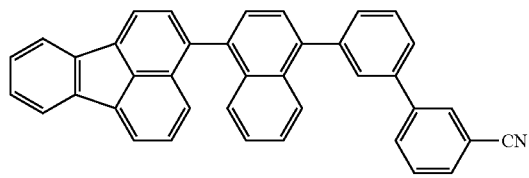
ET 4-25
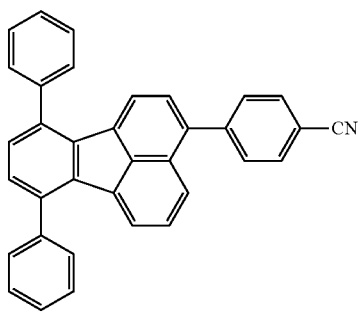
ET 4-26
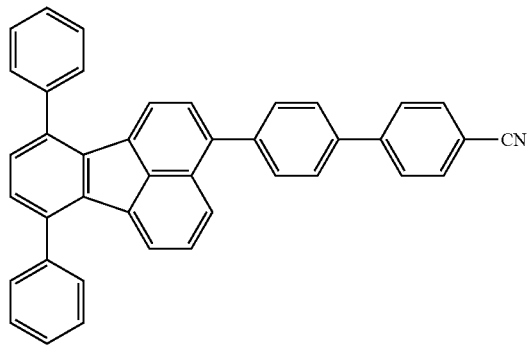
ET 4-27
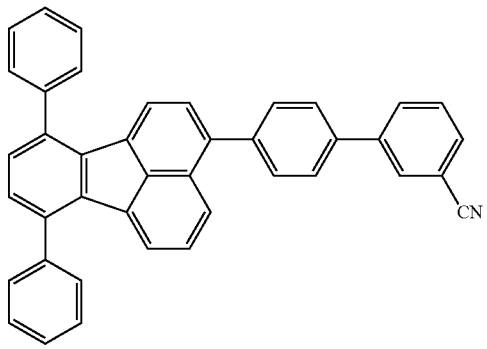
ET 4-28
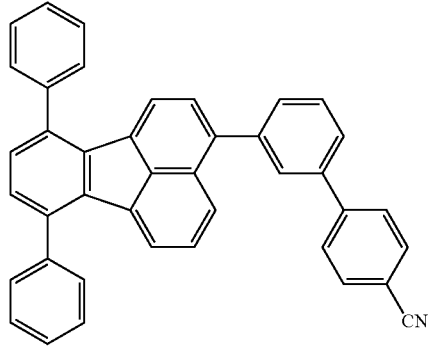
ET 4-29
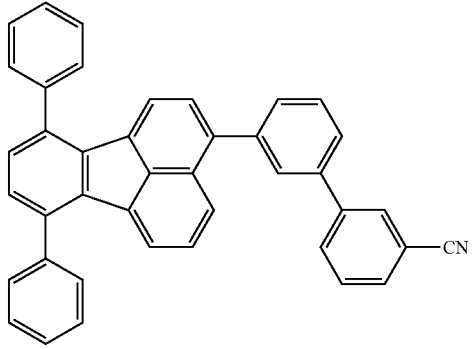

ET 4-30
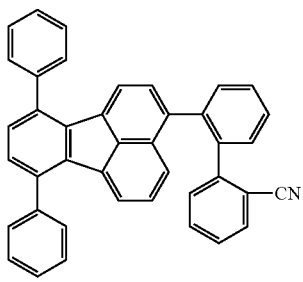
ET 4-31
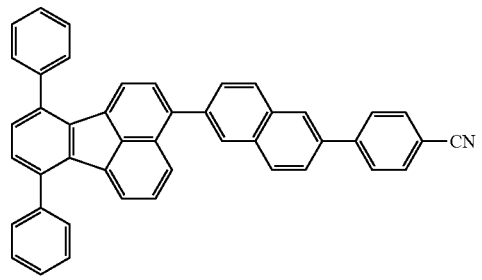
ET 4-32
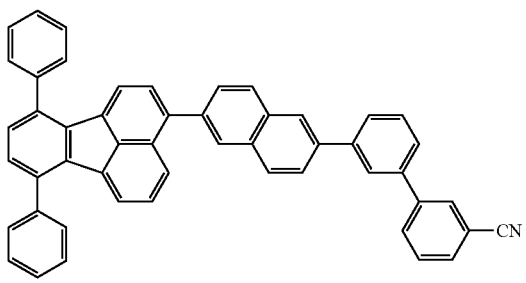
ET 4-33
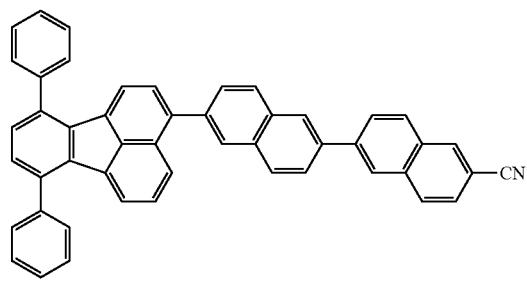
ET 4-34
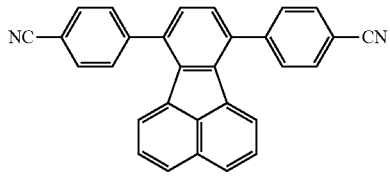
ET 4-35
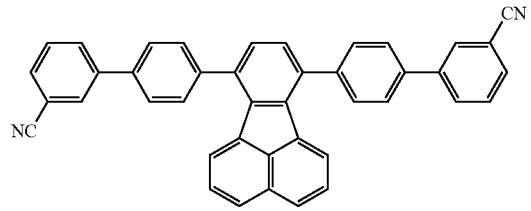
ET 4-36
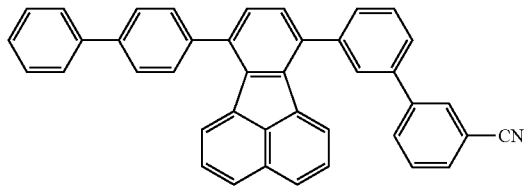
ET 4-37
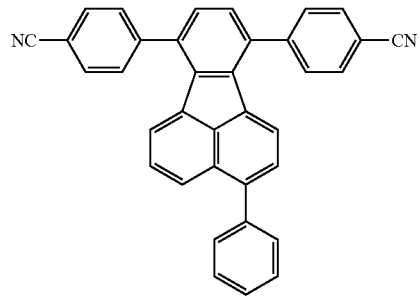
ET 4-38
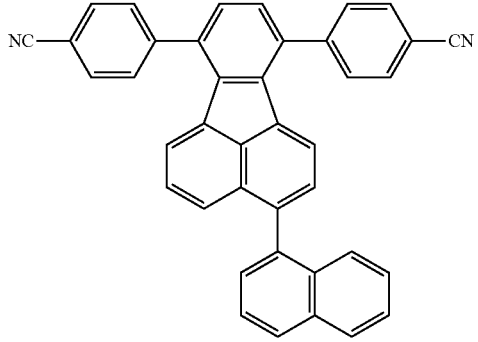
ET 4-39
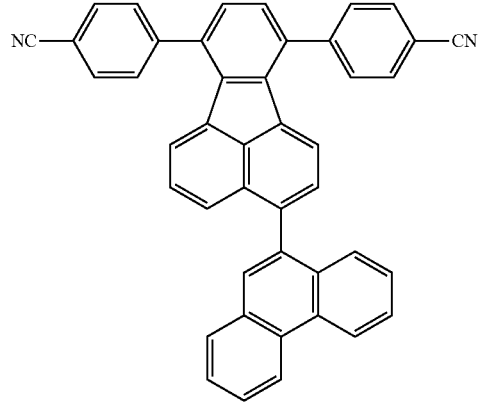

-continued
ET 4-40
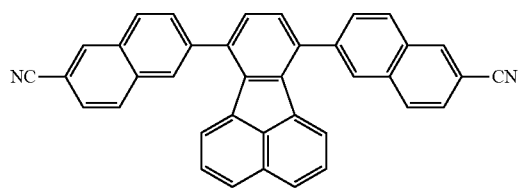
ET 4-41
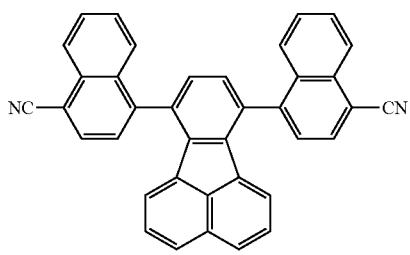
ET 4-42
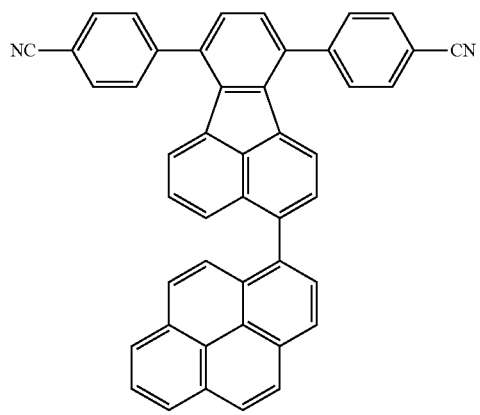
ET 4-43
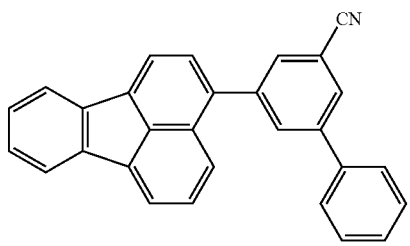
ET 4-44
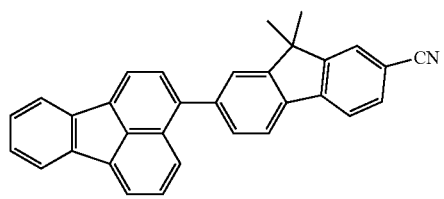
ET 4-45
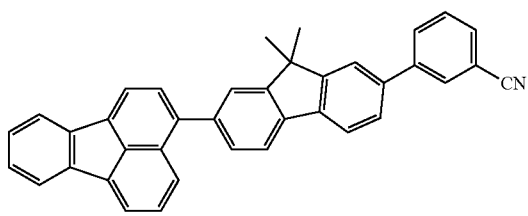
ET 4-46
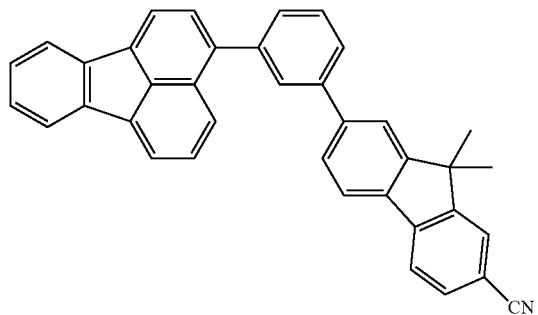
ET 4-47
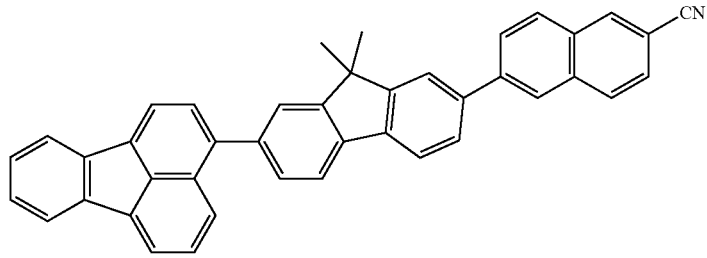

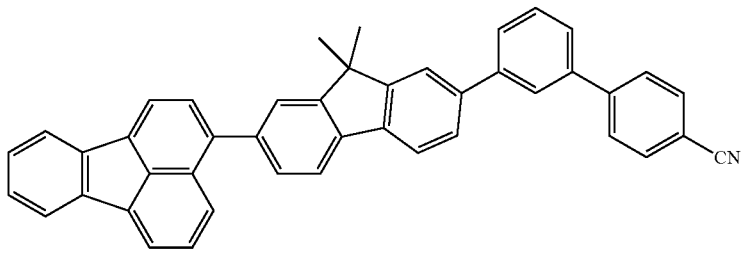
ET 4-48
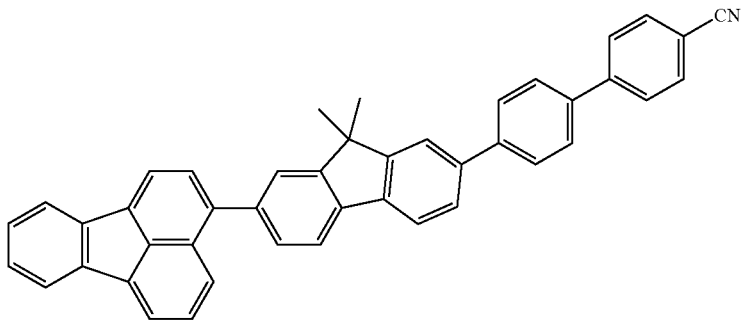
ET 4-49
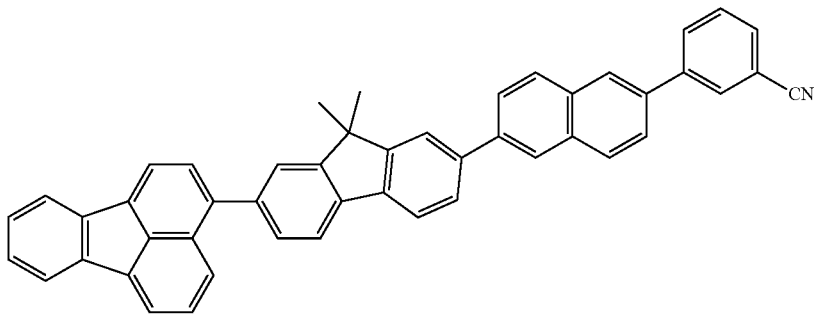
ET 4-50
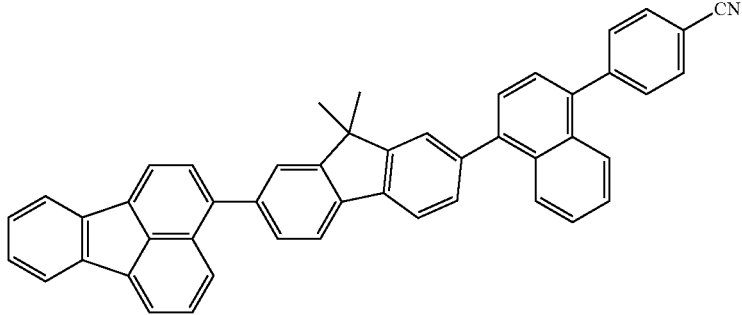
ET 4-51
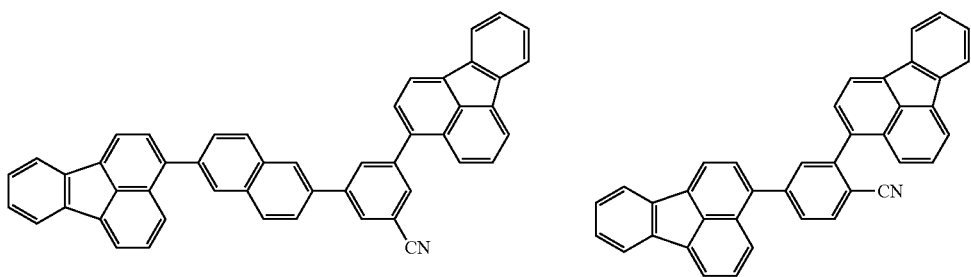
ET 4-52                                    ET 4-53

-continued
ET 4-54
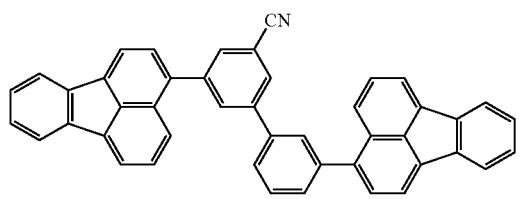
ET 4-55
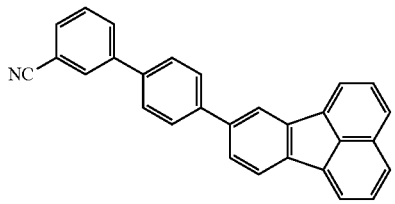
ET 4-56
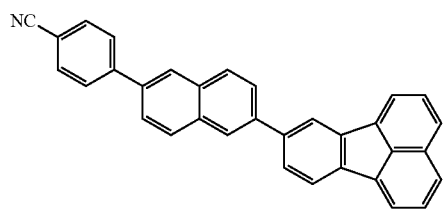
ET 4-57
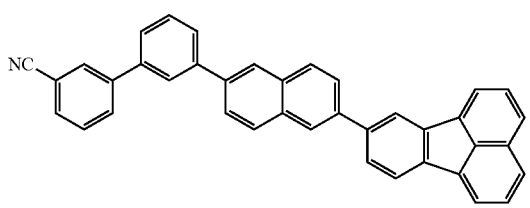
ET 4-58
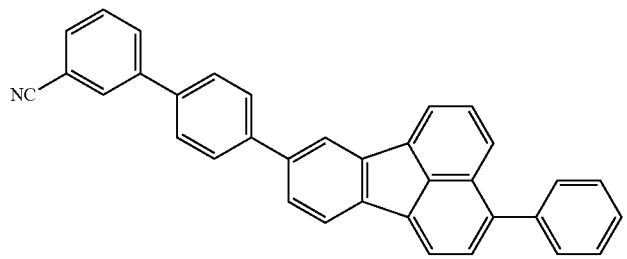
ET 4-59
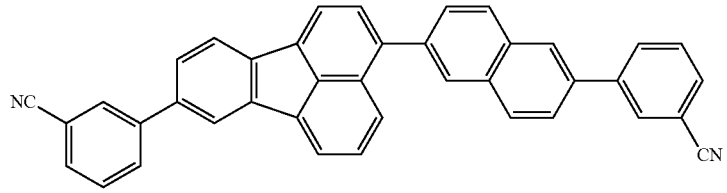
ET 4-60
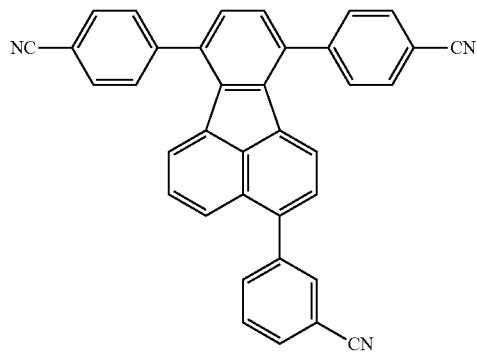
Specific examples of the compound shown by the formula (5) that includes a phenanthrene skeleton are shown below.
ET 5-01
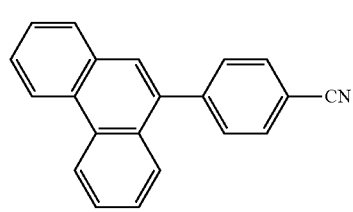
-continued
ET 5-02
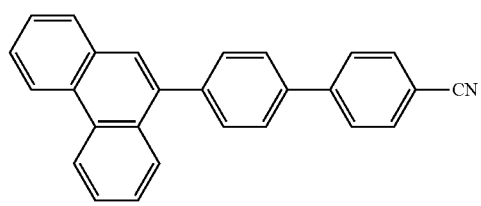

-continued
ET 5-03
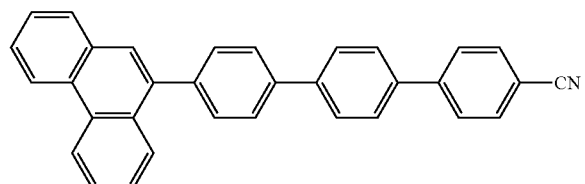
ET 5-04
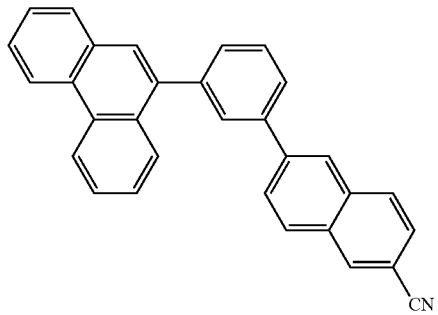
ET 5-05
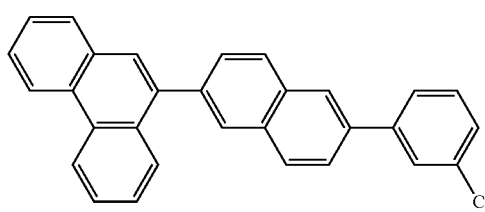
ET 5-06
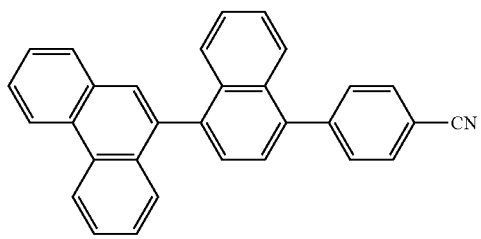
ET 5-07
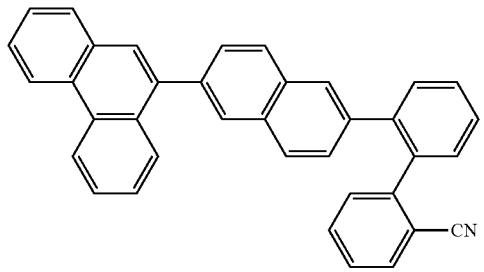
ET 5-08
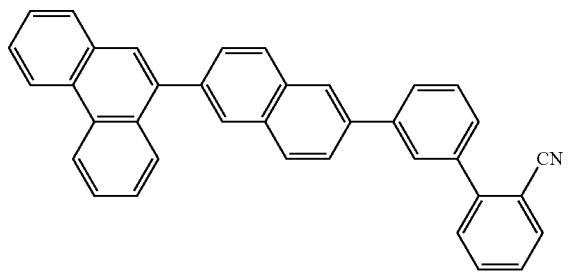
ET 5-09
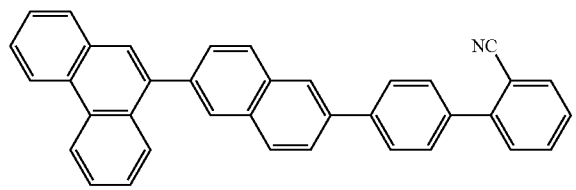
ET 5-10
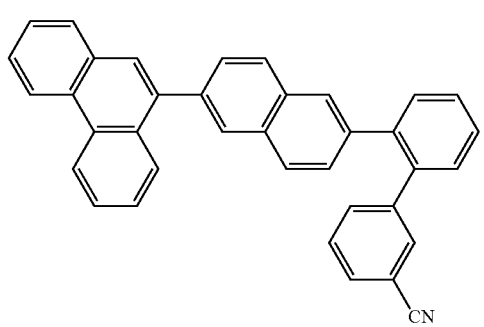
ET 5-11
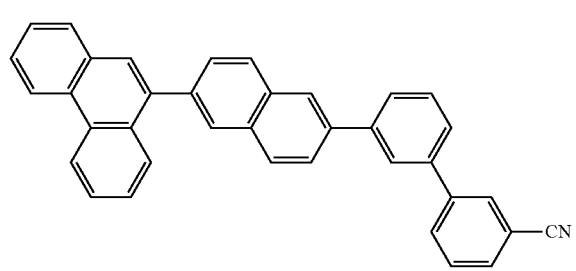
ET 5-12
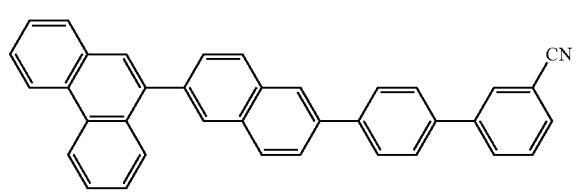
ET 5-13
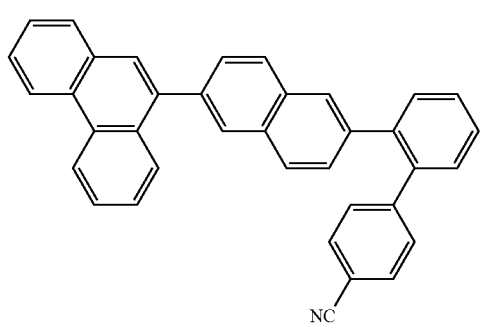

-continued
ET 5-14
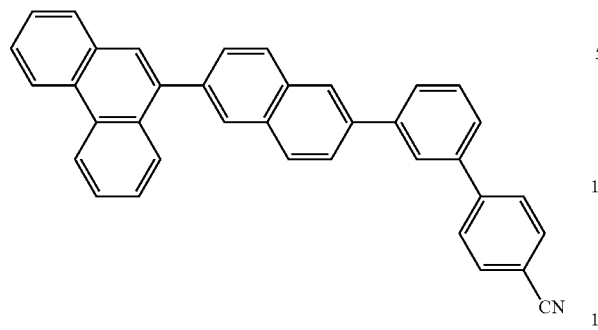
ET 5-15
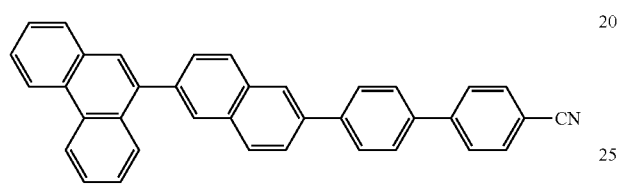
ET 5-16
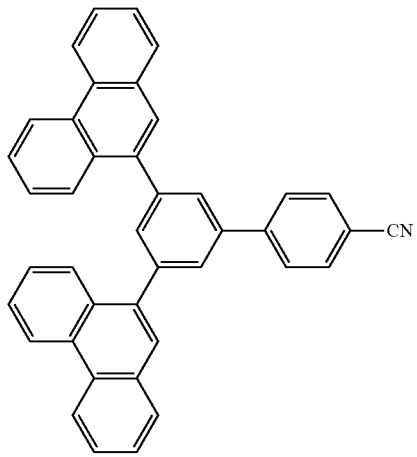
ET 5-17
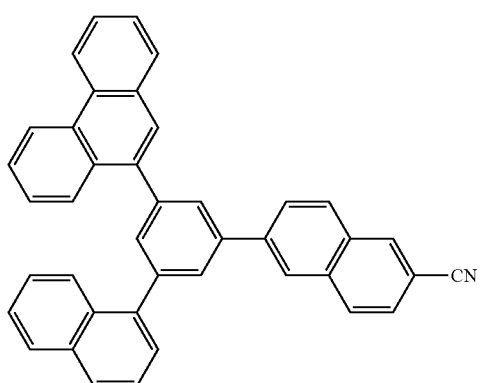
-continued
ET 5-18
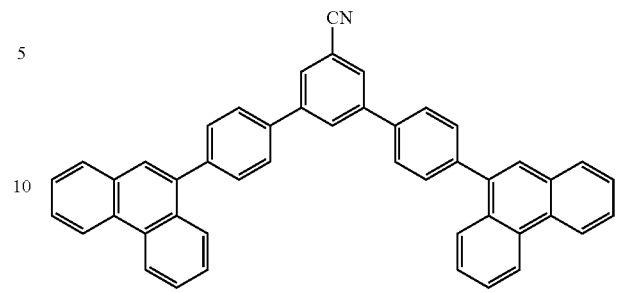
ET 5-19
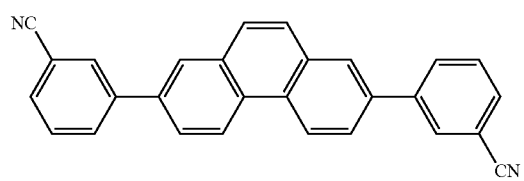
ET 5-20
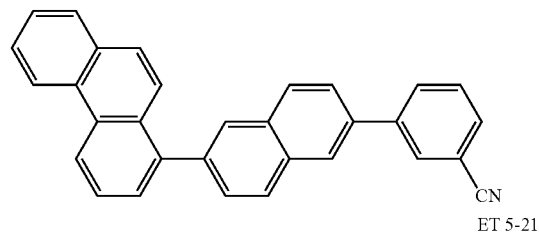
ET 5-21
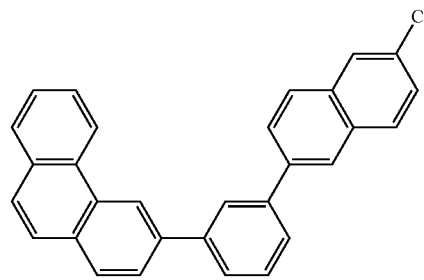
ET 5-22
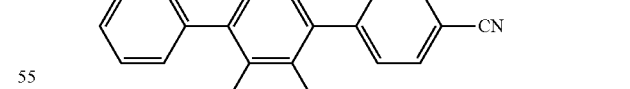
ET 5-23
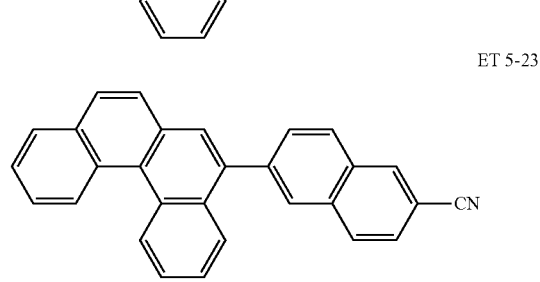

ET 5-24
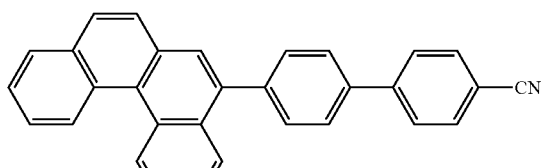
ET 5-25
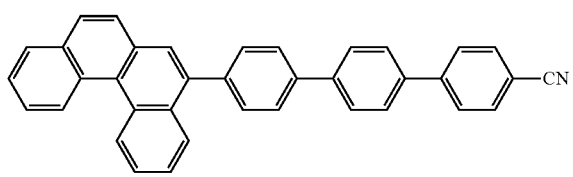
ET 5-26
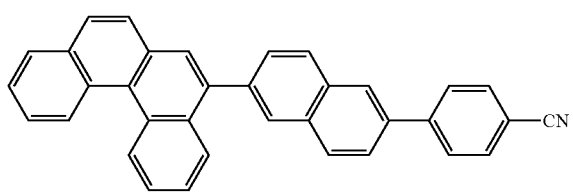
ET 5-27
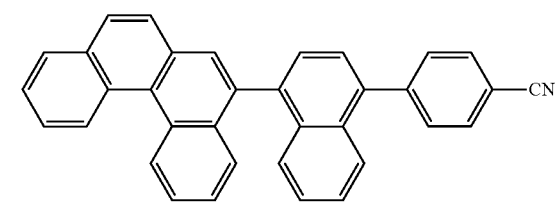
ET 5-28
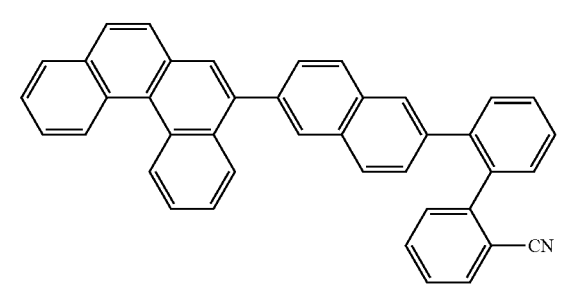
ET 5-29
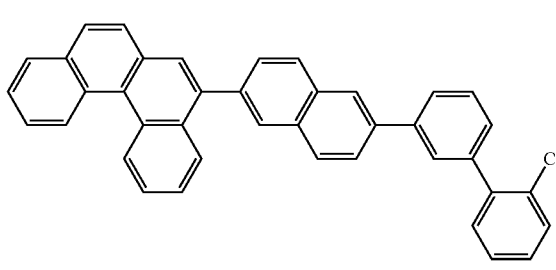
ET 5-30
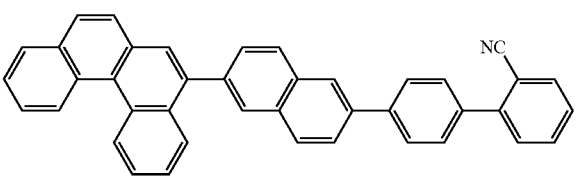
ET 5-31
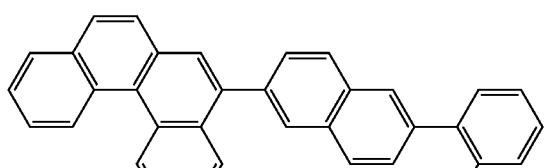
ET 5-32
ET 5-33
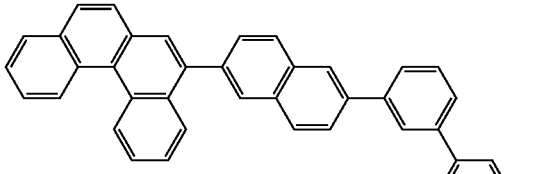
ET 5-34
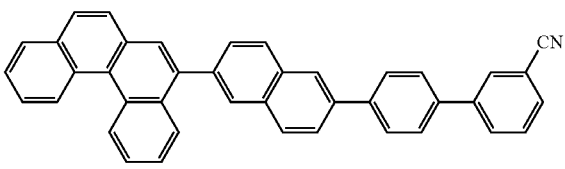
ET 5-35
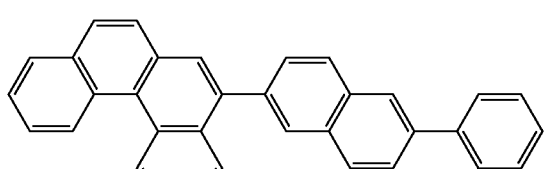
ET 5-36
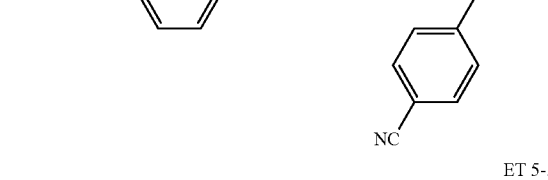
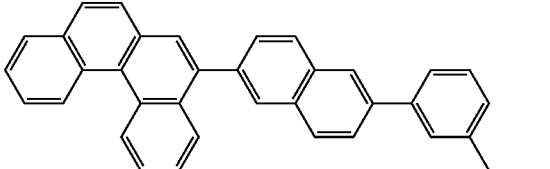
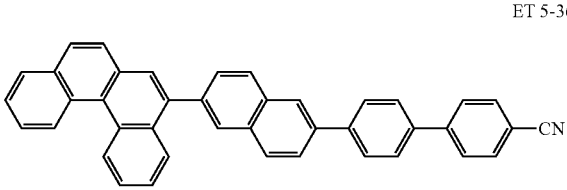

ET 5-37
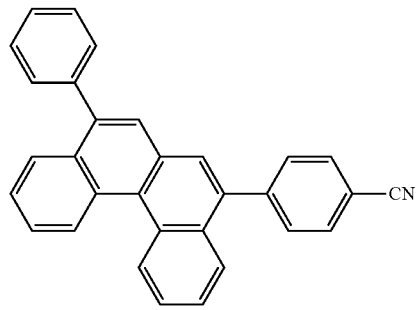
ET 5-38
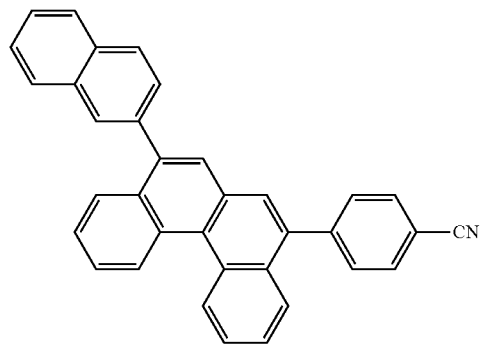
ET 5-39
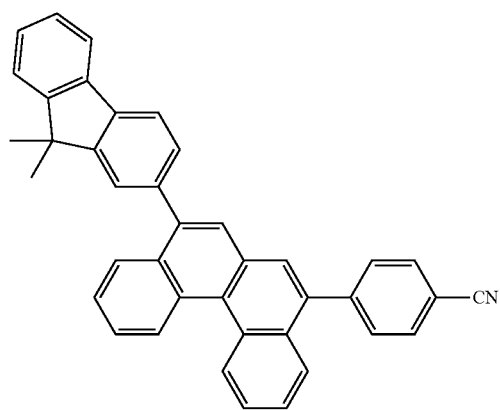
ET 5-40
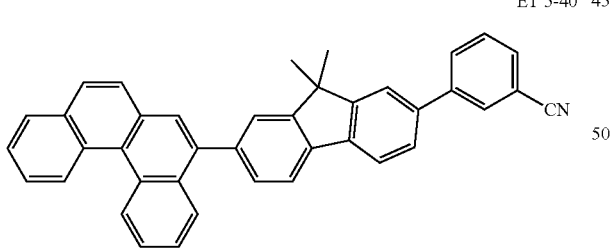
ET 5-41
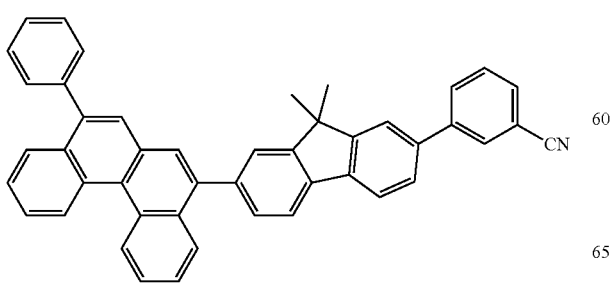
ET 5-42
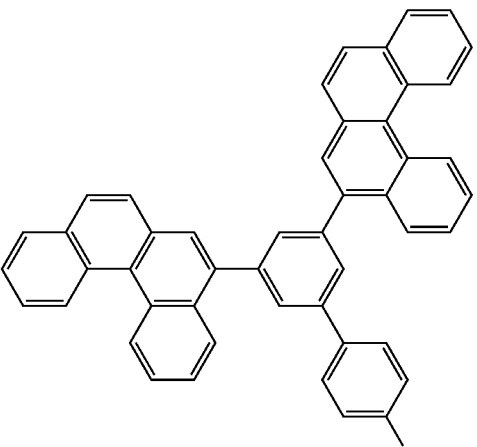
ET 5-43
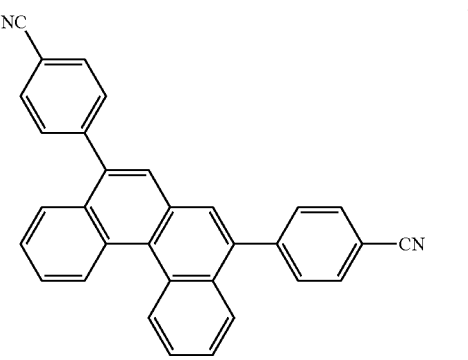
ET 5-44
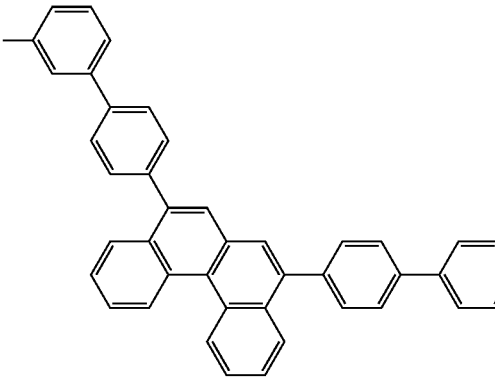
ET 5-45
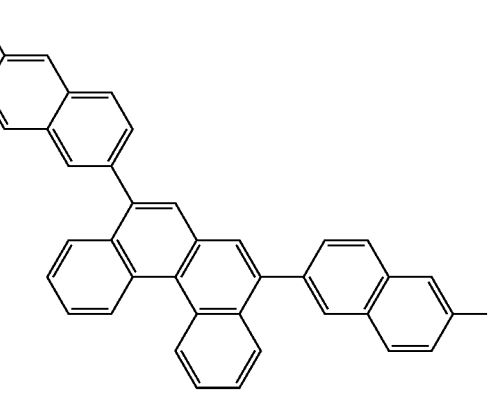

ET 5-46
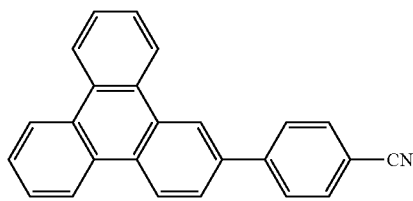
ET 5-51
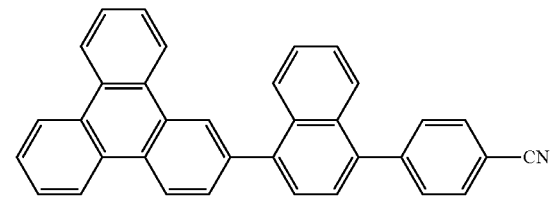
ET 5-47
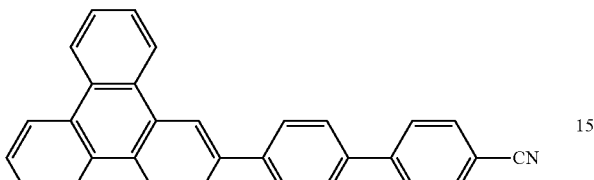
ET 5-52
ET 5-48
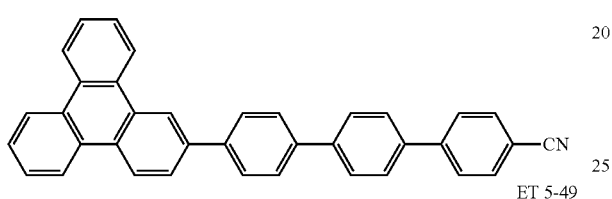
ET 5-53
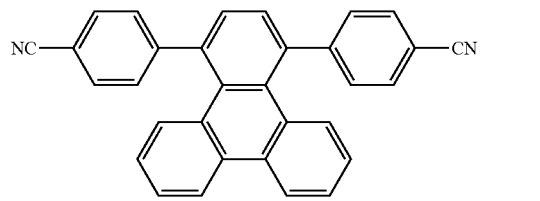
ET 5-49
ET 5-54
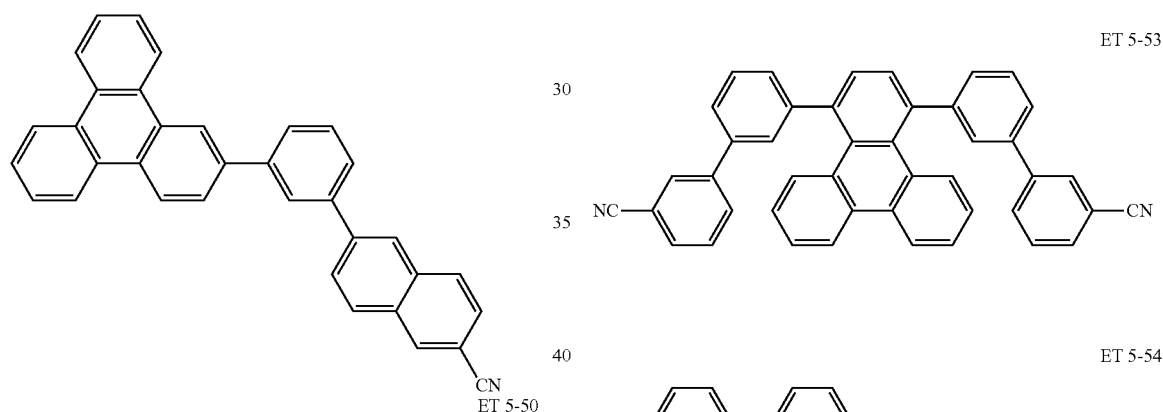
ET 5-50
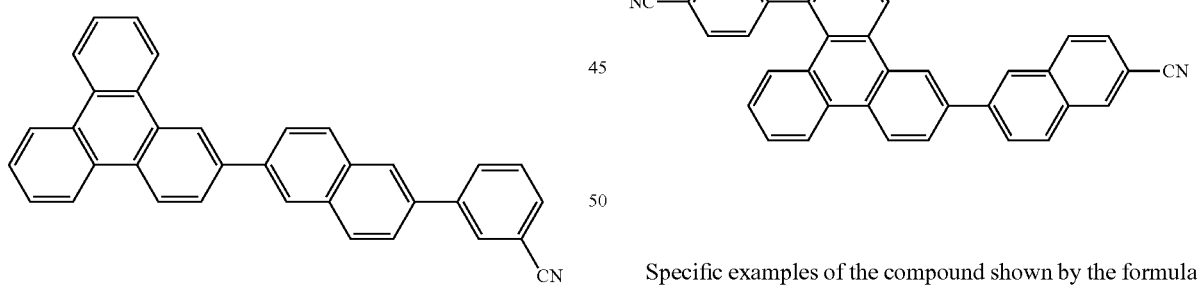
Specific examples of the compound shown by the formula (6) that includes a chrysene skeleton are shown below.
ET 6-01
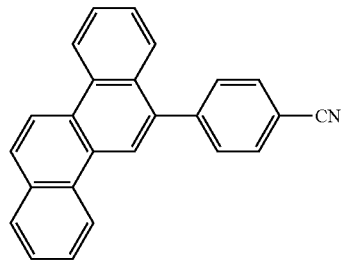
ET 6-02
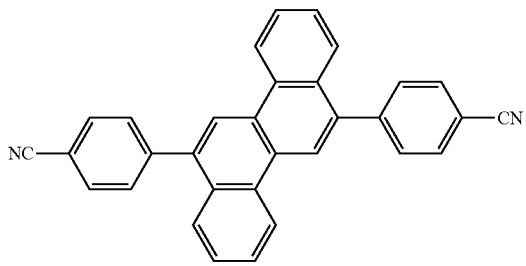

-continued
ET 6-03
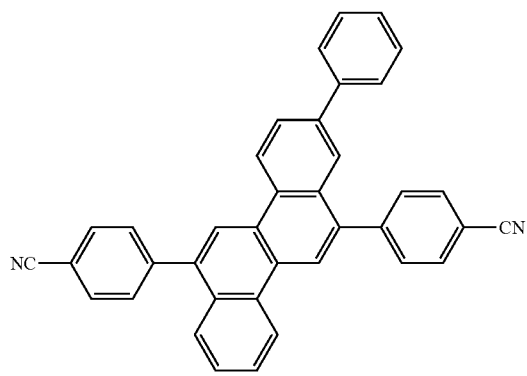
ET 6-04
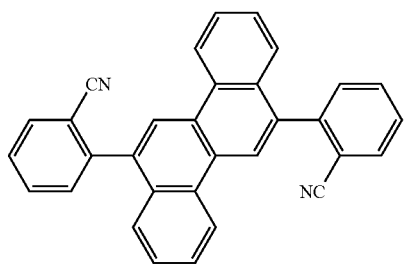
ET 6-05
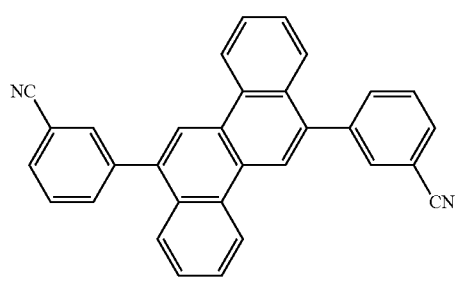
ET 6-06
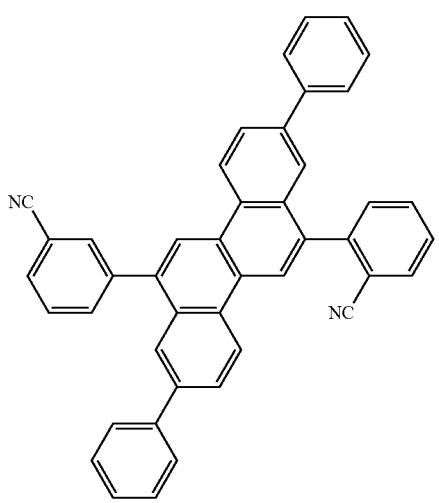
ET 6-07
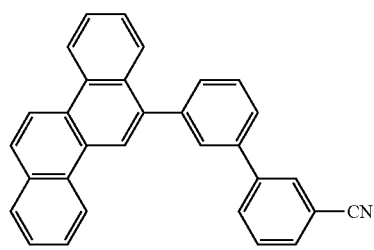
ET 6-08
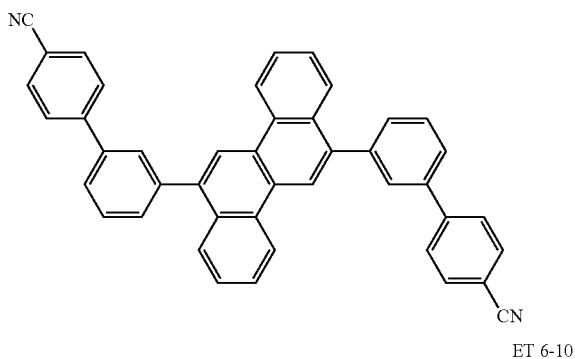
ET 6-09
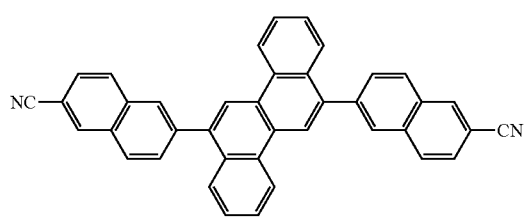
ET 6-10
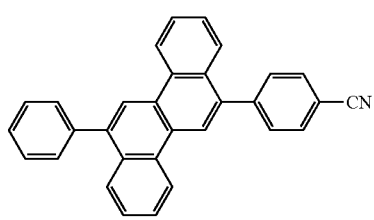

-continued
ET 6-11
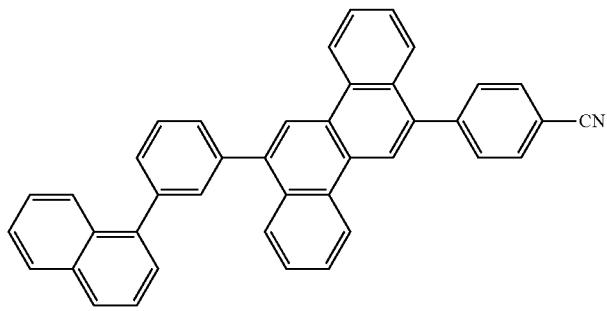
ET 6-12
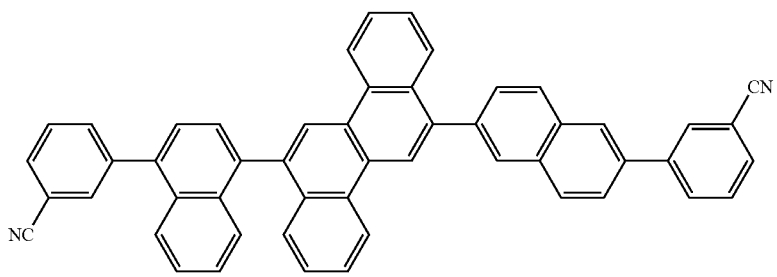
ET 6-13
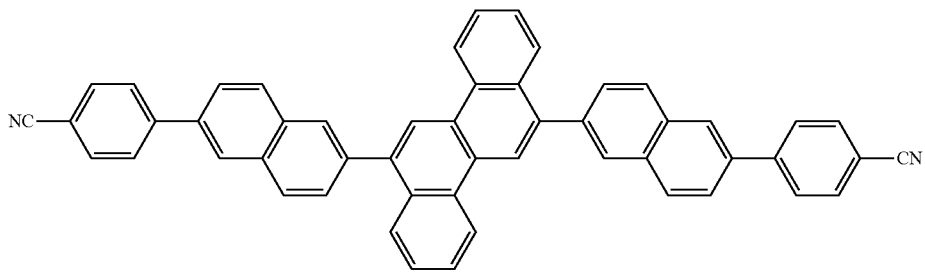
ET 6-14
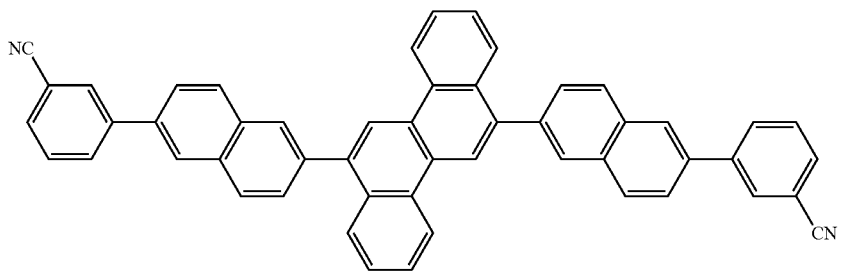
ET 6-15
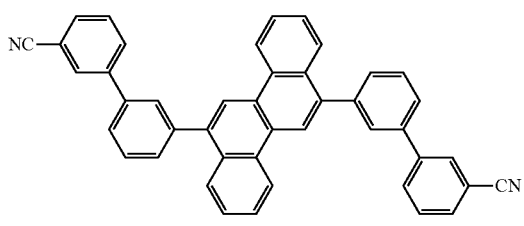
ET 6-16
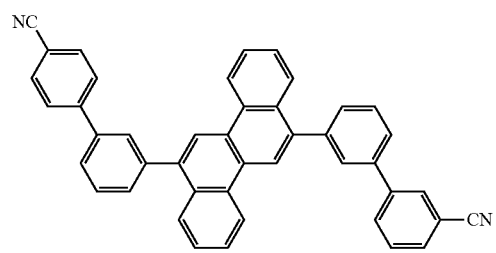

-continued
ET 6-17
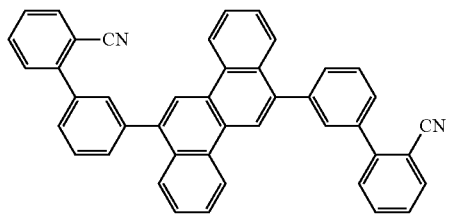
ET 6-18
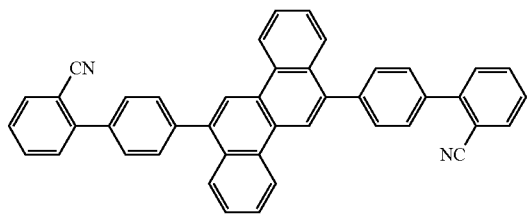
ET 6-19
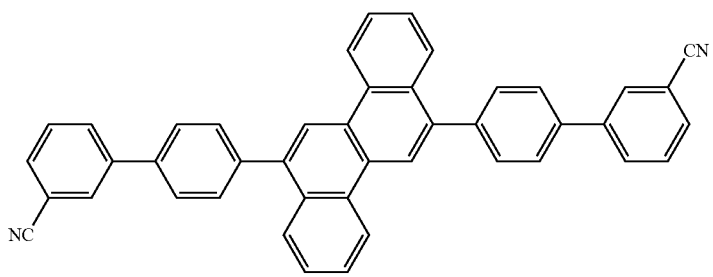
ET 6-20
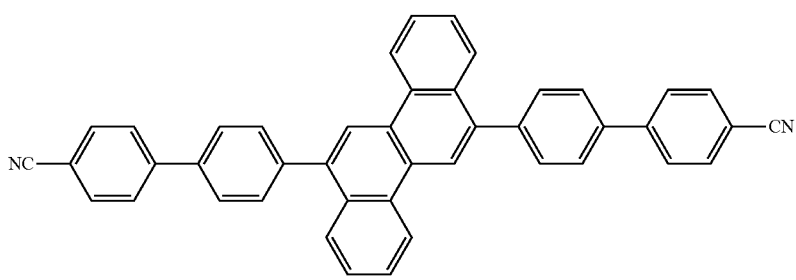
ET 6-21
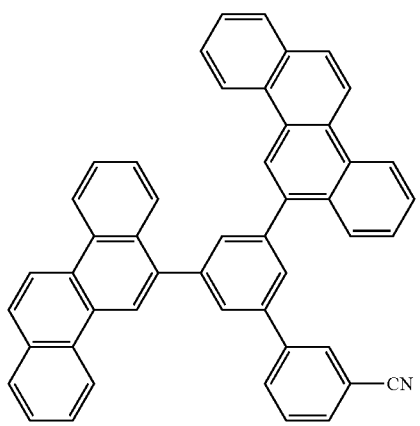
ET 6-22
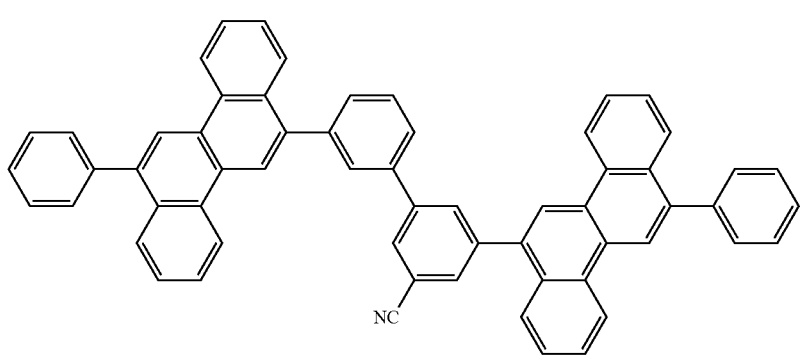

ET 6-23
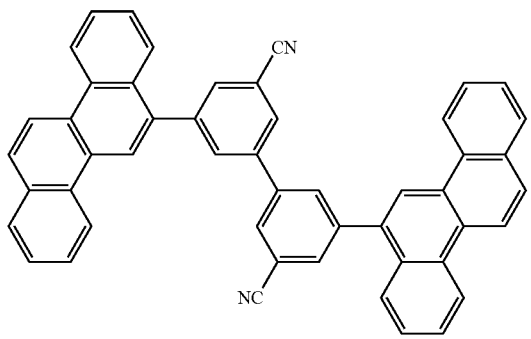
ET 6-24
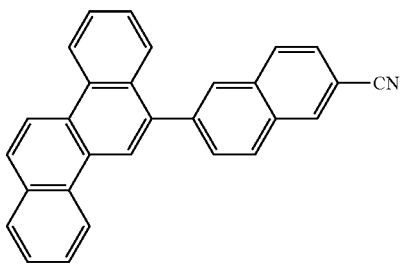
ET 6-25
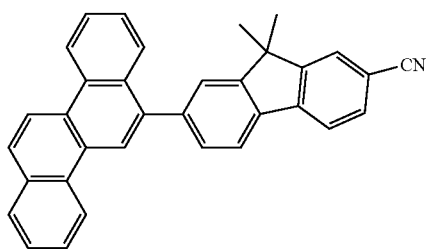
ET 6-26
Specific examples of the compound shown by the formula (7) that includes a benzochrysene skeleton are shown below.
ET 7-01
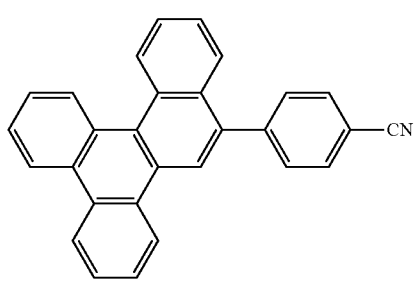
ET 7-02
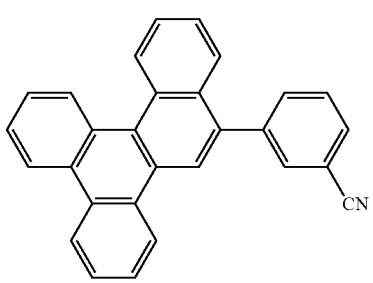
ET 7-03
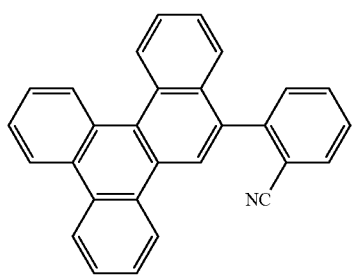
ET 7-04
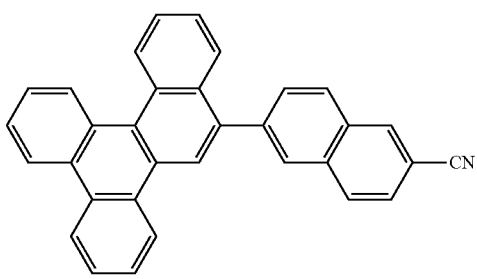
ET 7-05
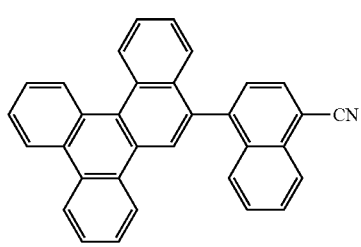
ET 7-06
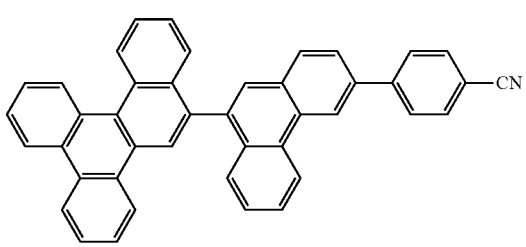

ET 7-07
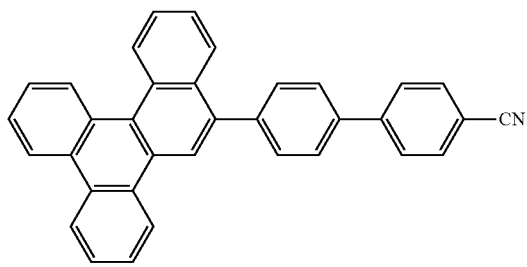
ET 7-08
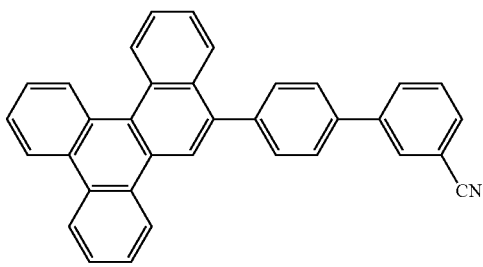
ET 7-09
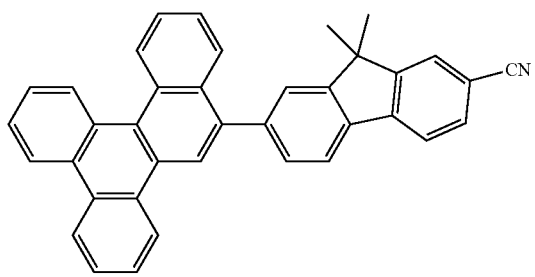
ET 7-10
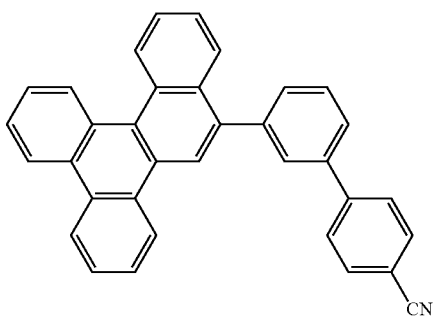
ET 7-11
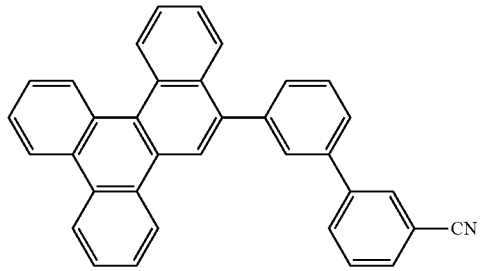
ET 7-12
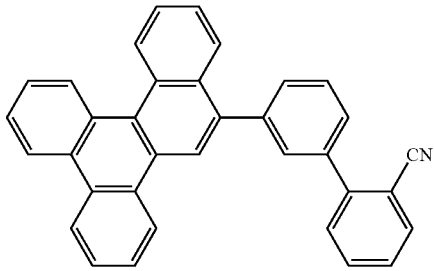
ET 7-13
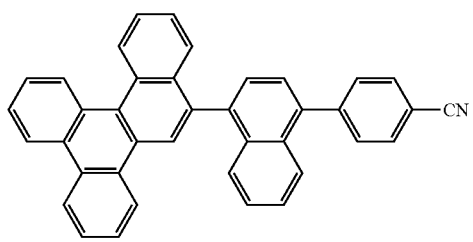
ET 7-14
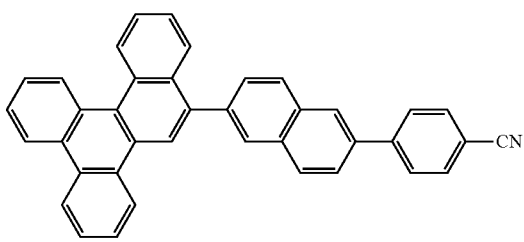
ET 7-15
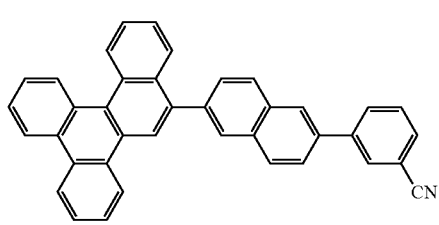
ET 7-16
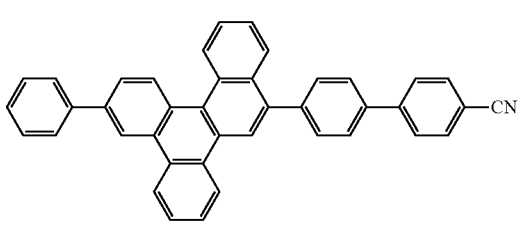
ET 7-17
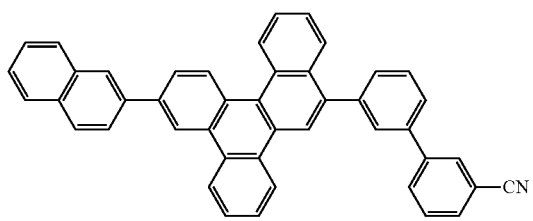
ET 7-18
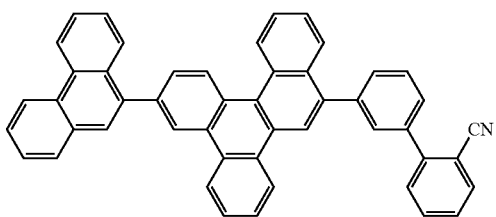

-continued
ET 7-19
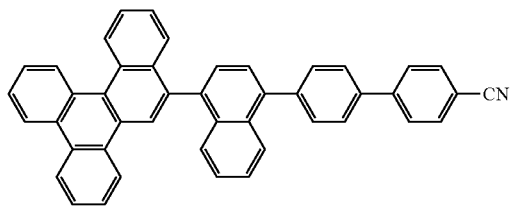
ET 7-20
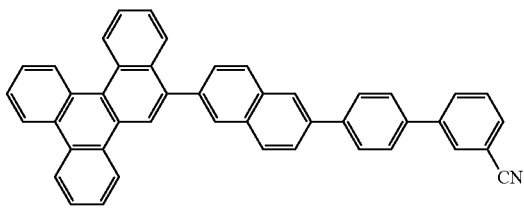
ET 7-21
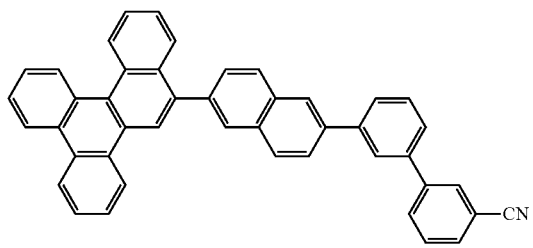
ET 7-22
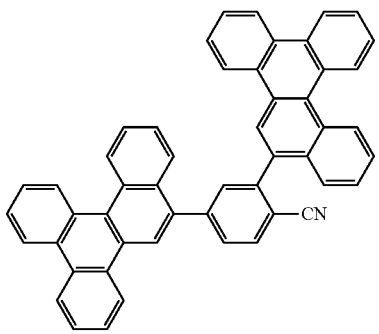
ET 7-23
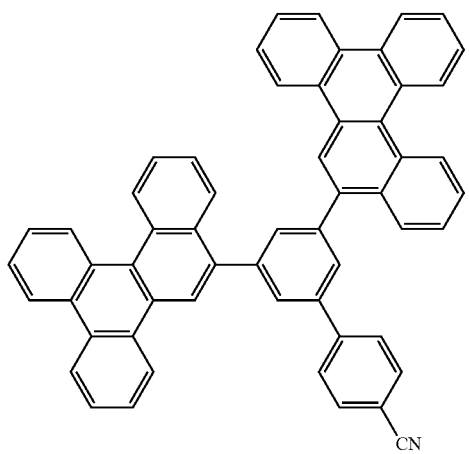
ET 7-24
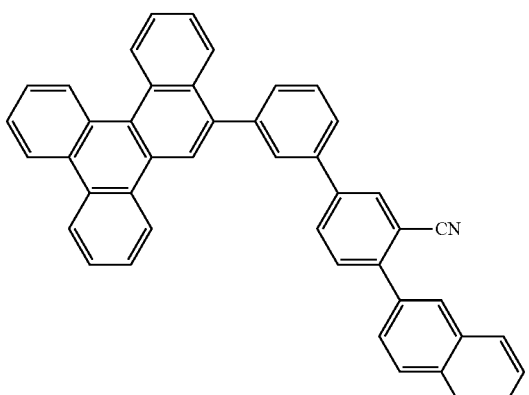
ET 7-25
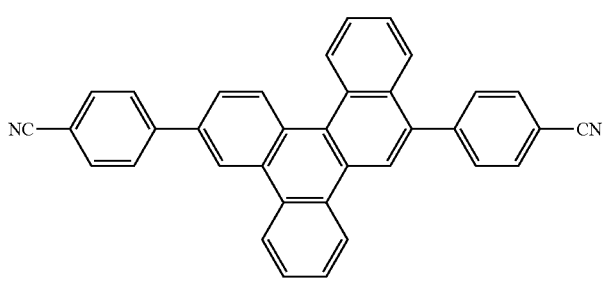
ET 7-26
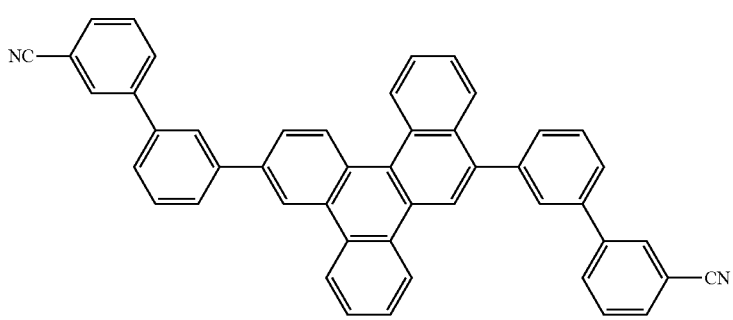

ET 7-27
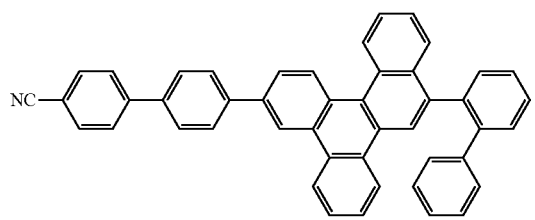
ET 7-28
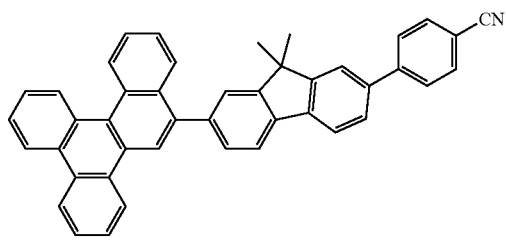
ET 7-29
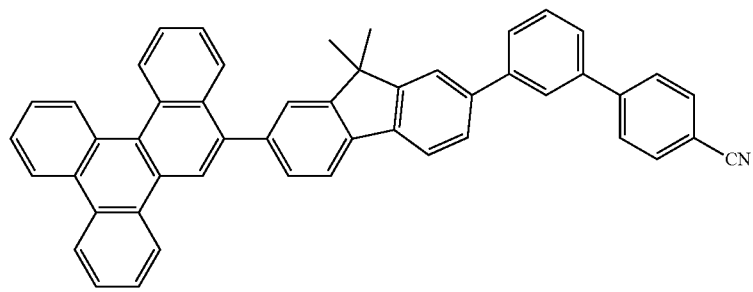
ET 7-30
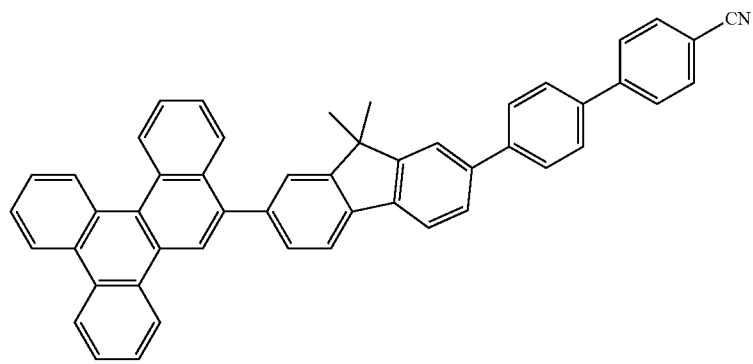
Specific examples of the compound shown by the formula (8) that includes a benzofuran skeleton are shown below.
ET 8-01
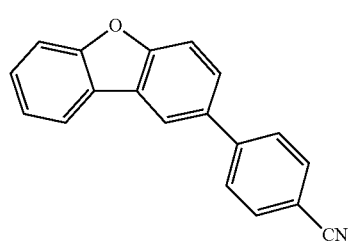
ET 8-02
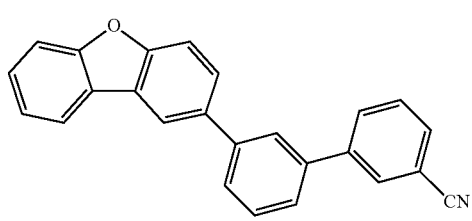
ET 8-03
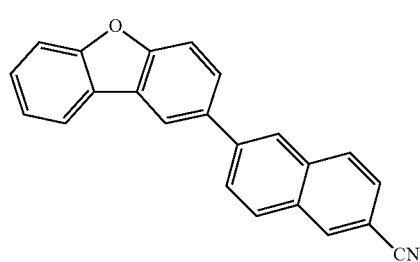
ET 8-04
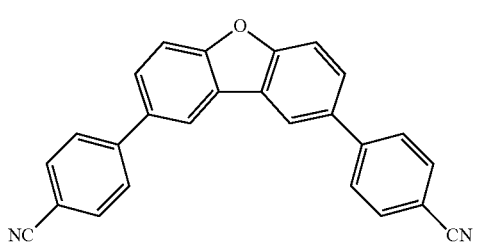

-continued
ET 8-05
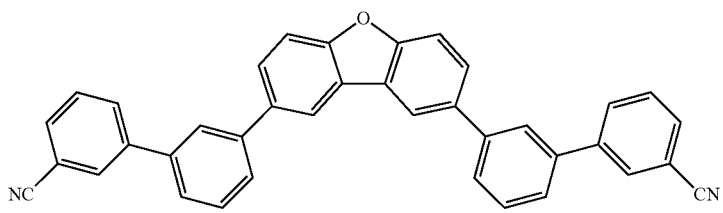
ET 8-06
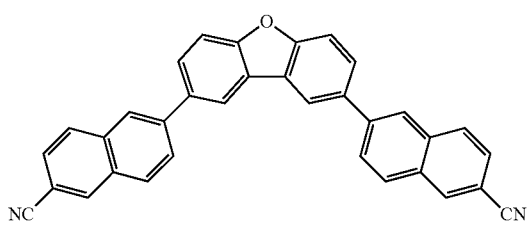
ET 8-07
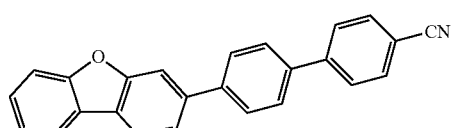
ET 8-08
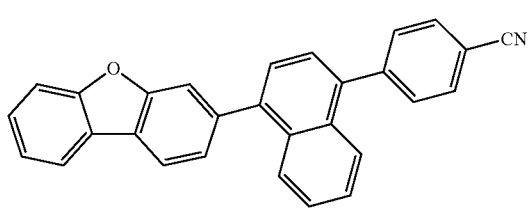
ET 8-09
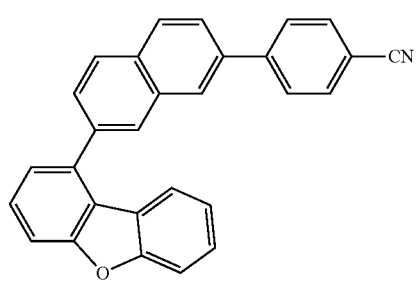
ET 8-10
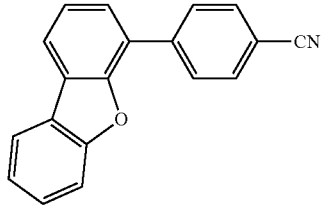
ET 8-11
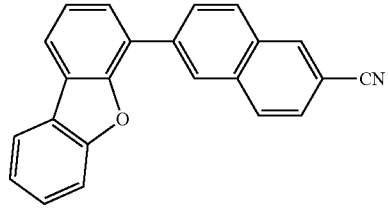
ET 8-12
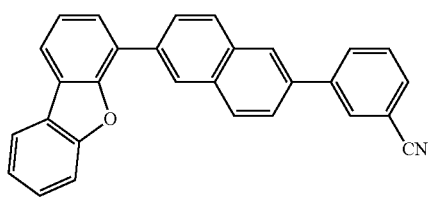
ET 8-13
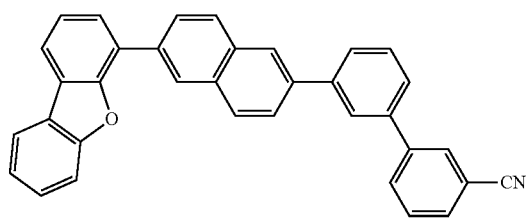
ET 8-14
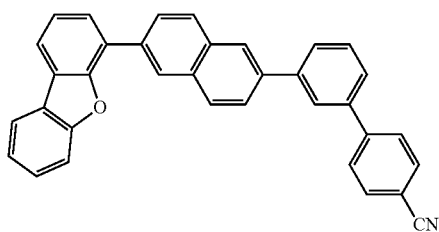
ET 8-15
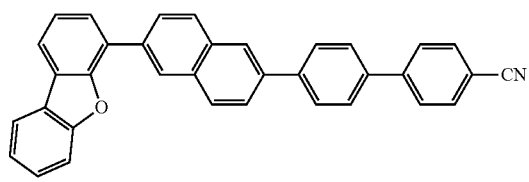

-continued
ET 8-16
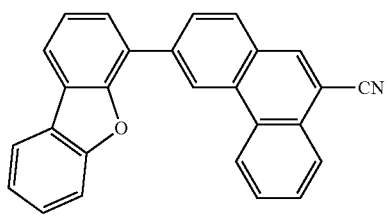
ET 8-17
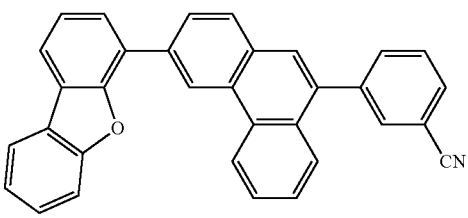
ET 8-18
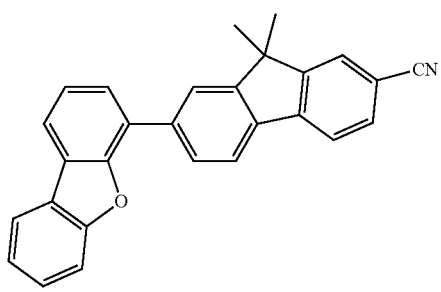
ET 8-19
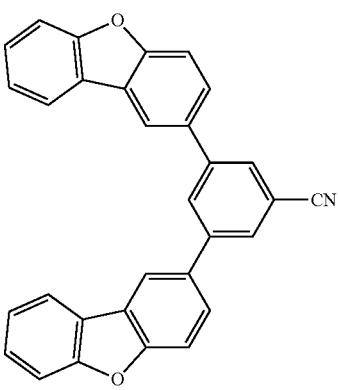
ET 8-20
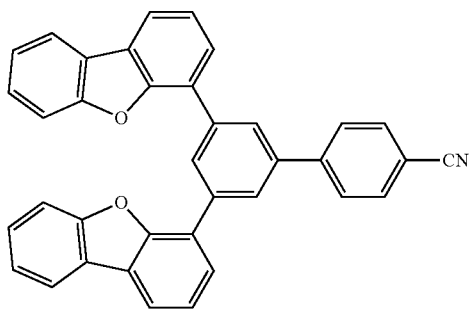
ET 8-21
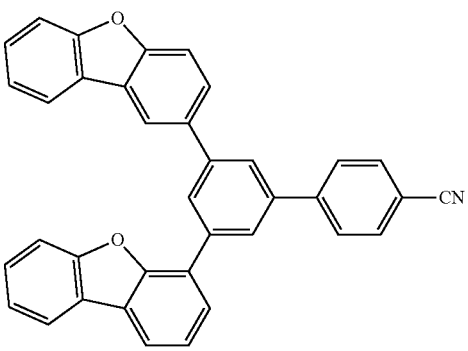
ET 8-22
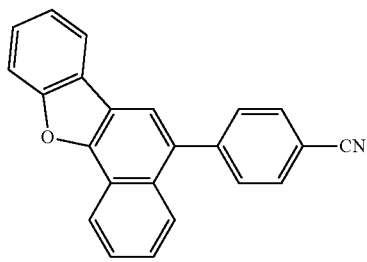
ET 8-23
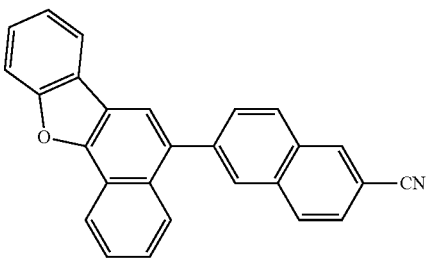
ET 8-24
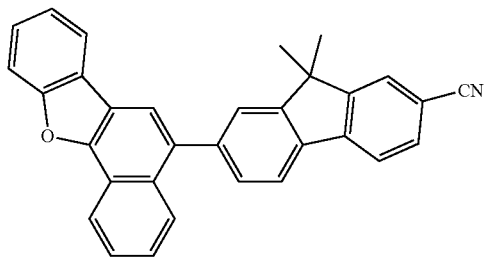
ET 8-25
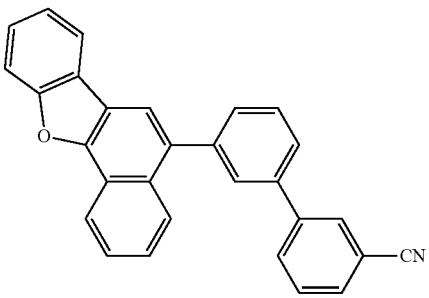

-continued
ET 8-26
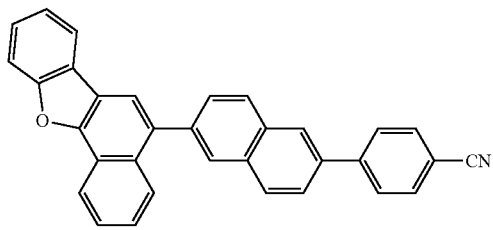
ET 8-27
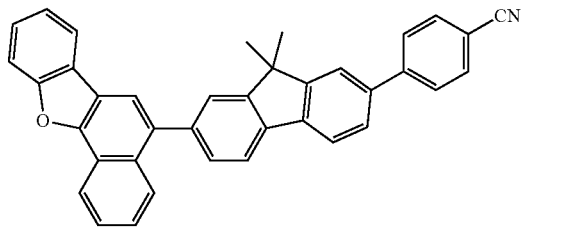
ET 8-28
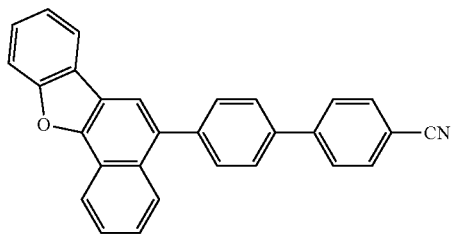
ET 8-29
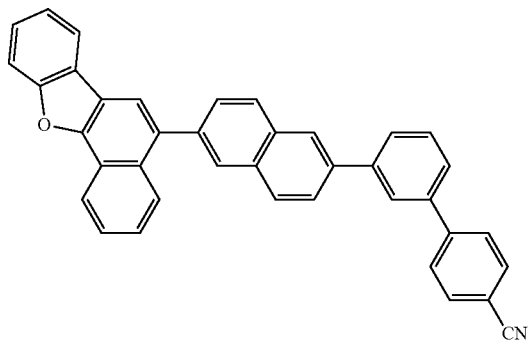
ET 8-30
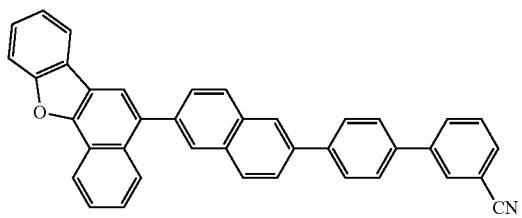
ET 8-31
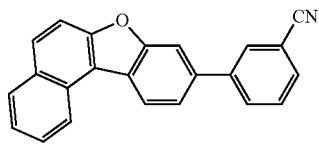
ET 8-32
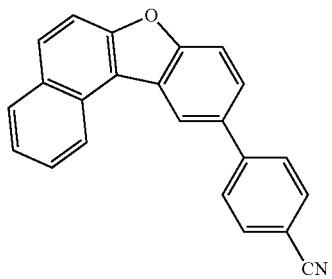
ET 8-33
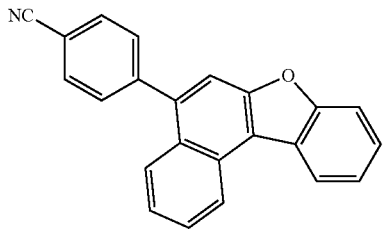
ET 8-34
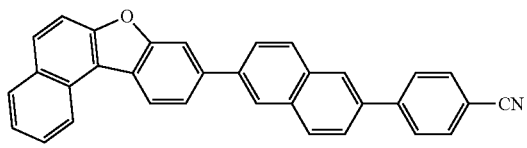
ET 8-35
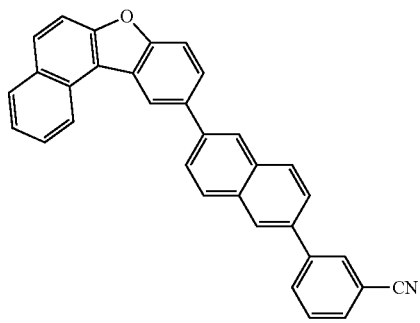

-continued
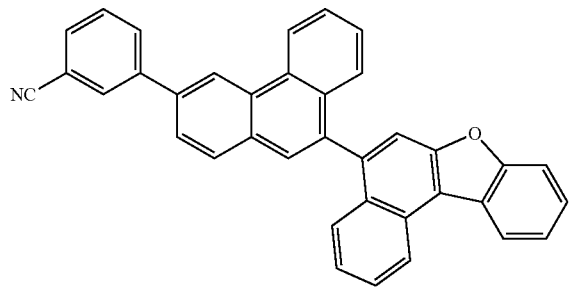
ET 8-36
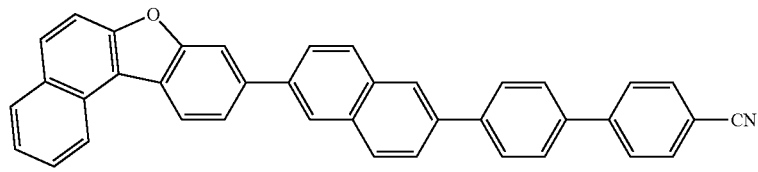
ET 8-37
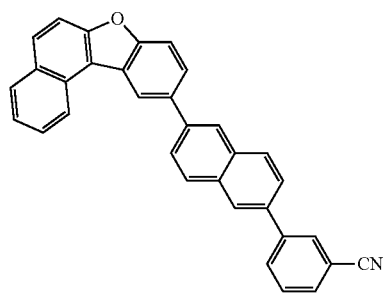
ET 8-38
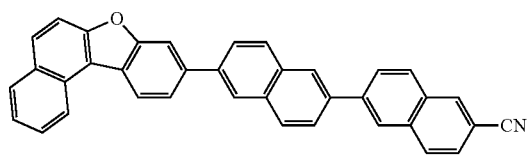
ET 8-39
Specific examples of the oxygen-containing fused aromatic ring compound shown by the formula (9) are shown below.
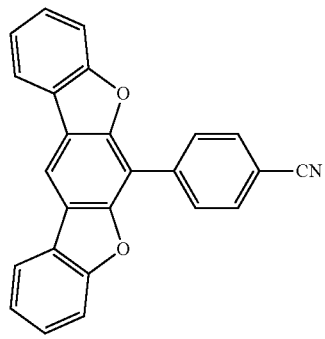
ET 9-01
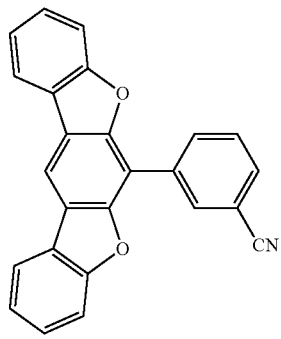
ET 9-02
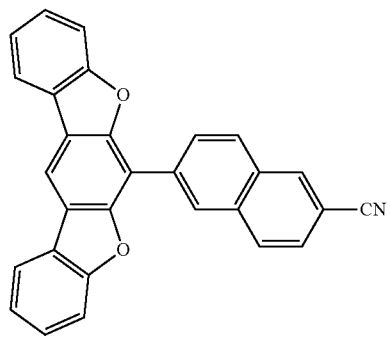
ET 9-03
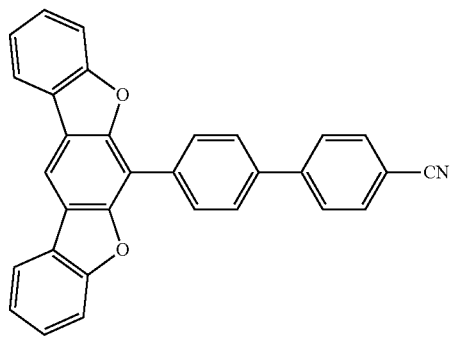
ET 9-04

-continued
ET 9-05
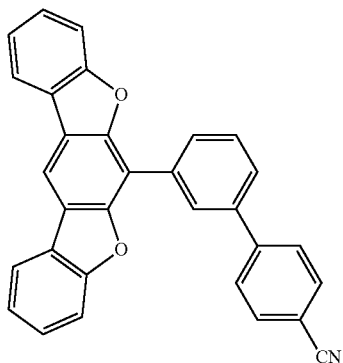
ET 9-06
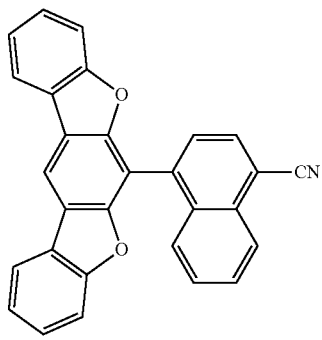
ET 9-07
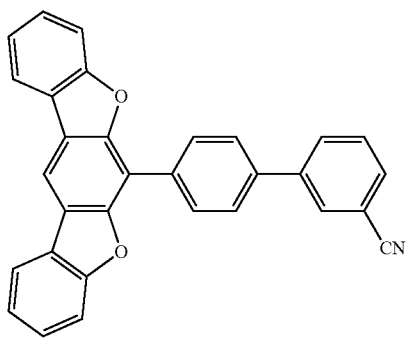
ET 9-08
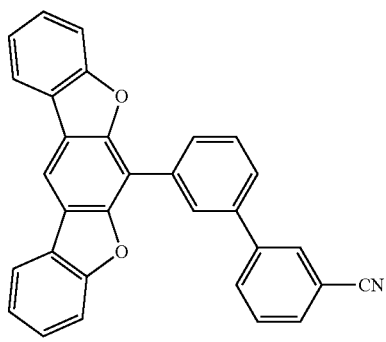
ET 9-09
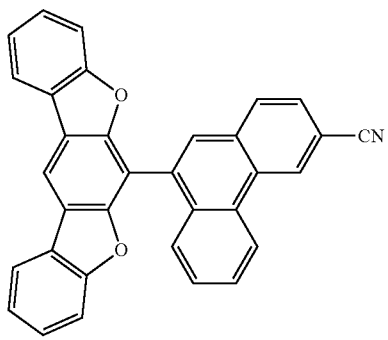
ET 9-10
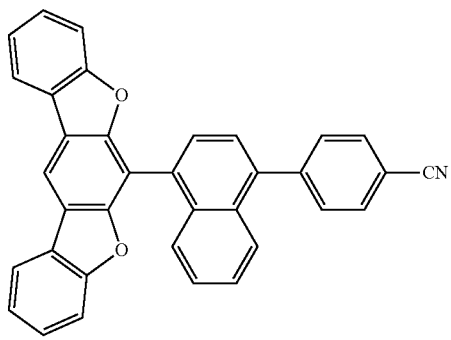
ET 9-11
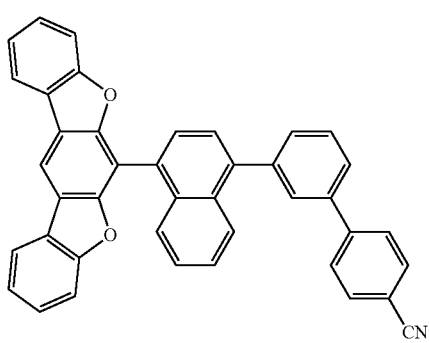
ET 9-12
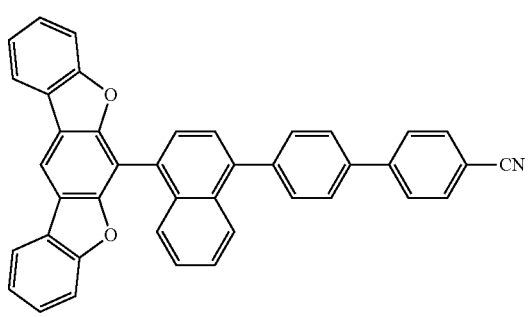

-continued
ET 9-13
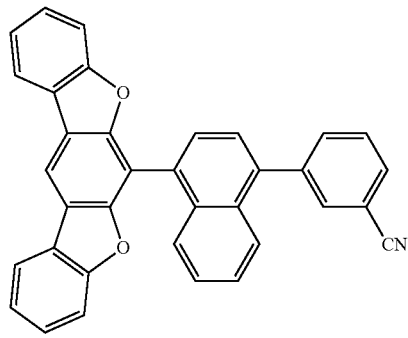
ET 9-14
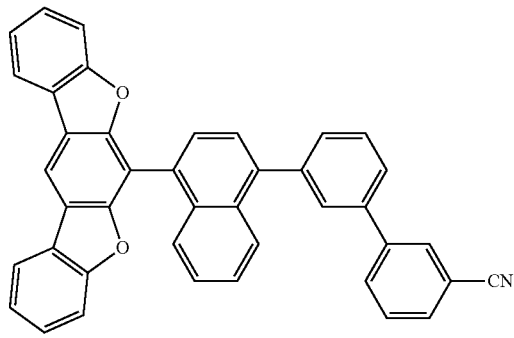
ET 9-15
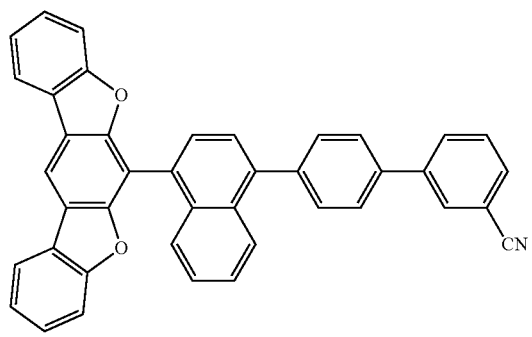
ET 9-16
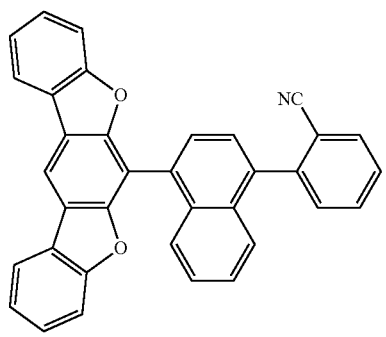
ET 9-17
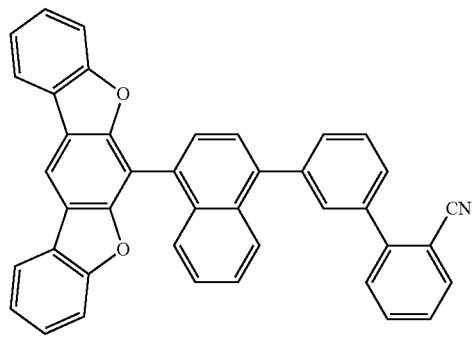
ET 9-18
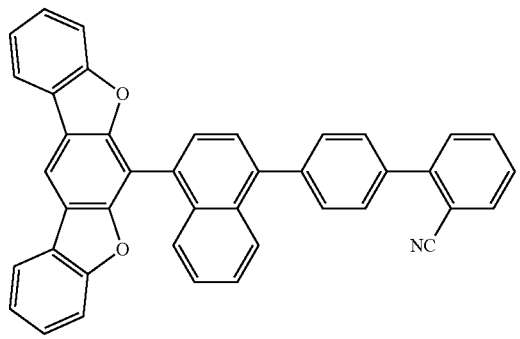
ET 9-19
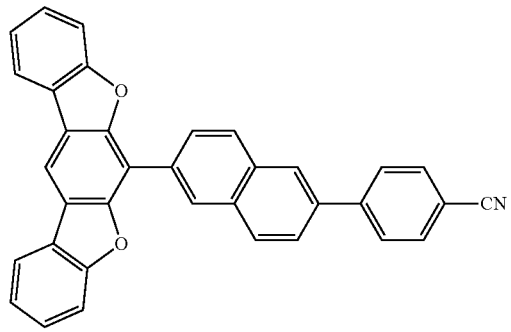
ET 9-20
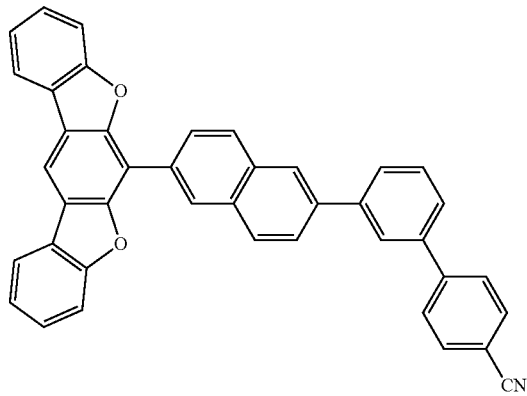

-continued
ET 9-21
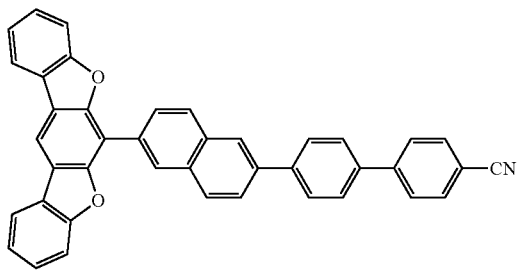
ET 9-22
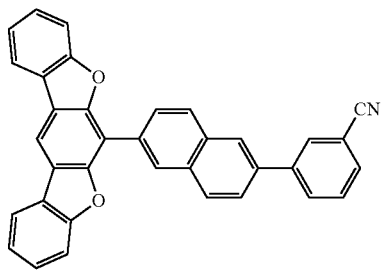
ET 9-23
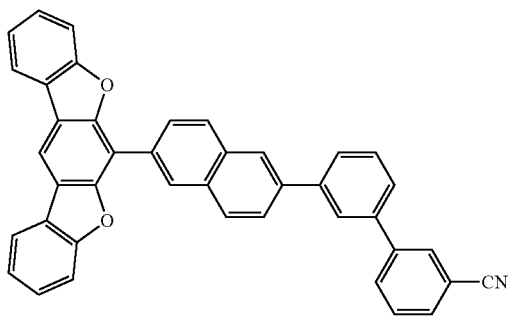
ET 9-24
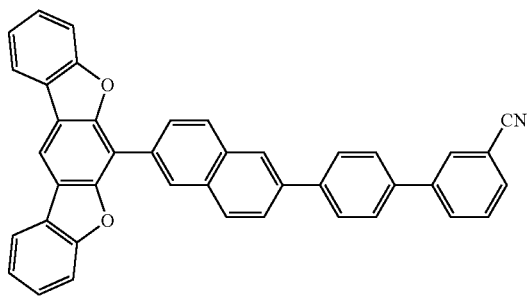
ET 9-25
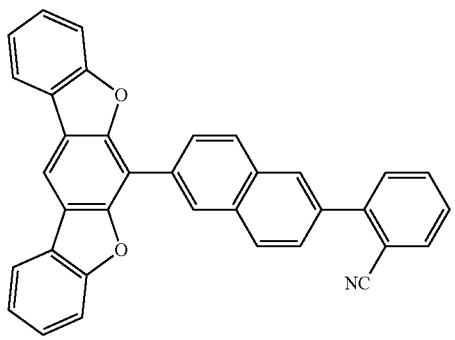
ET 9-26
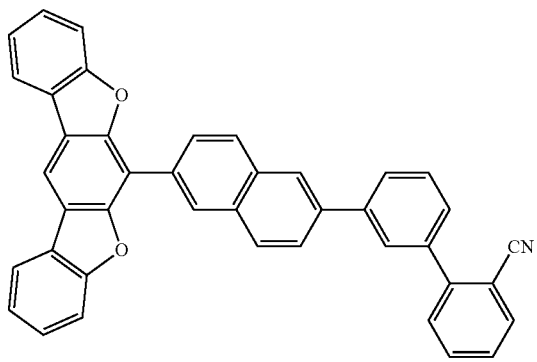
ET 9-27
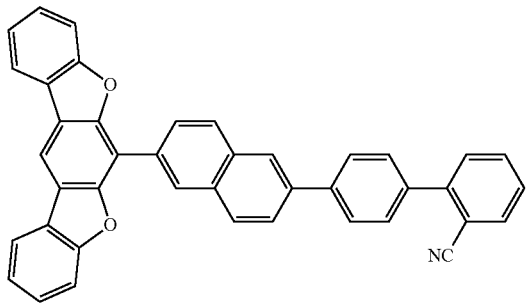
ET 9-28
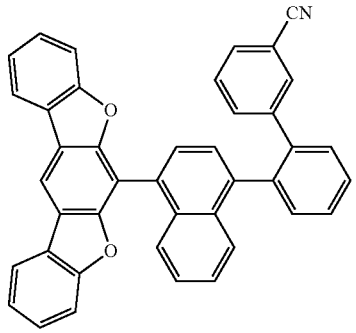

-continued
ET 9-29
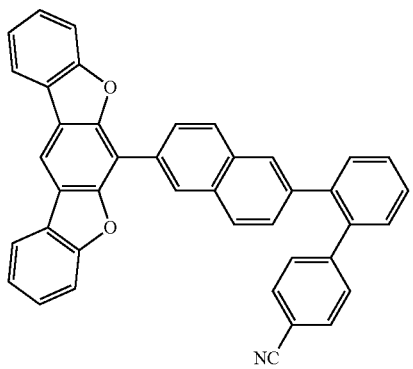
ET 9-30
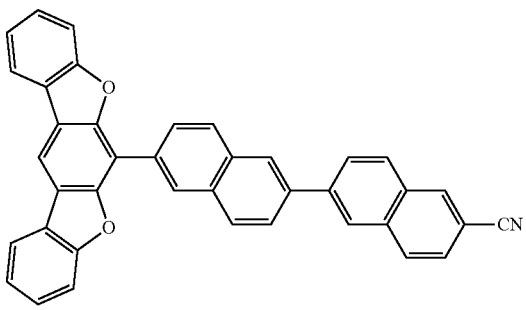
ET 9-31
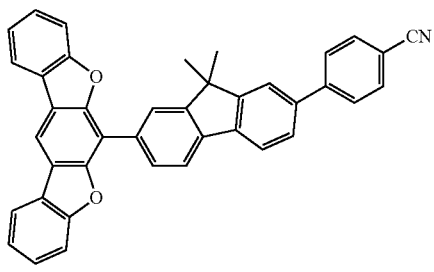
ET 9-32
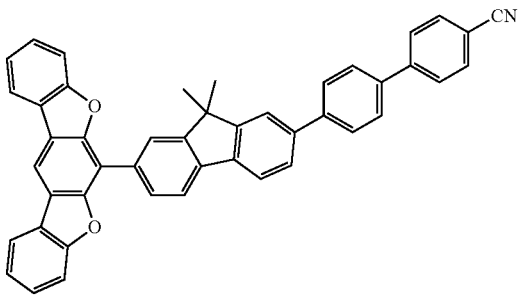
ET 9-33
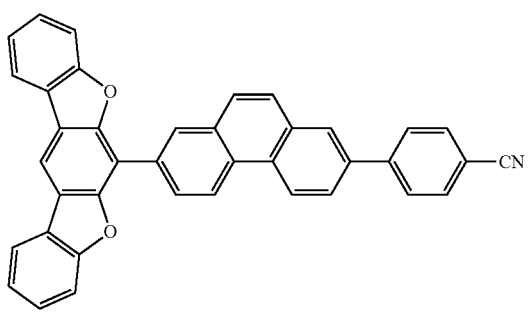
ET 9-34
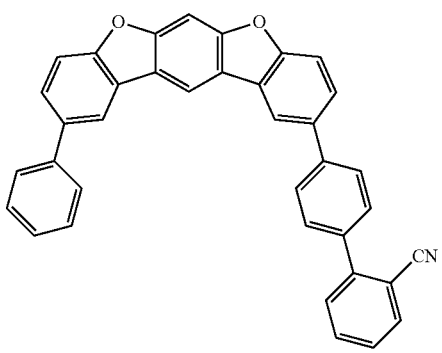
ET 9-35
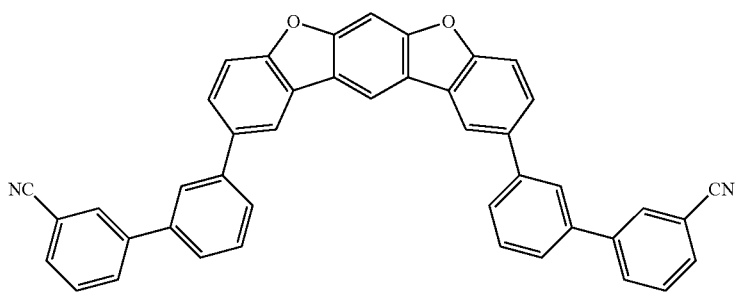

-continued
ET 9-36
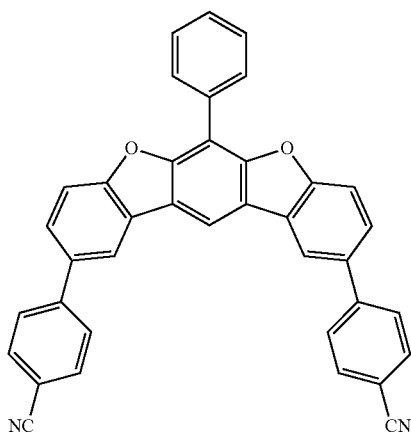
ET 9-37
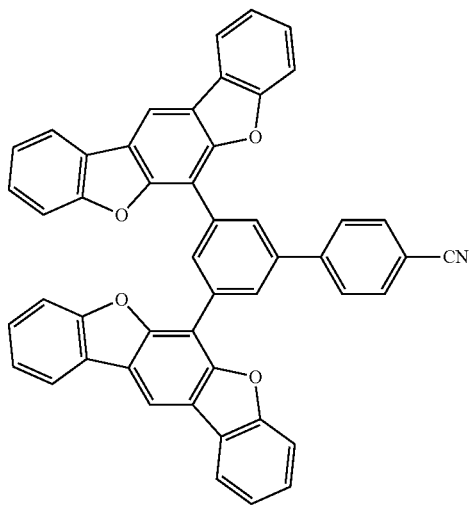
ET 9-38
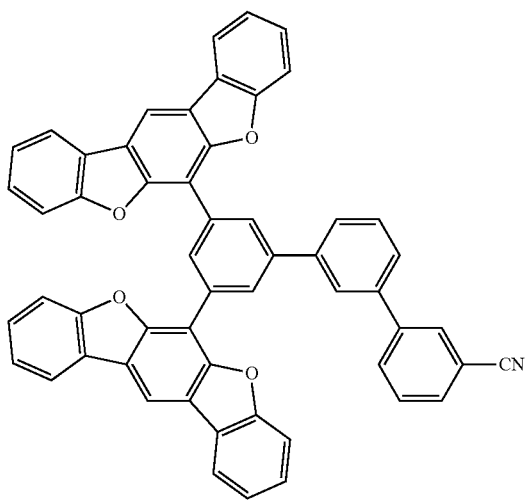
ET 9-39
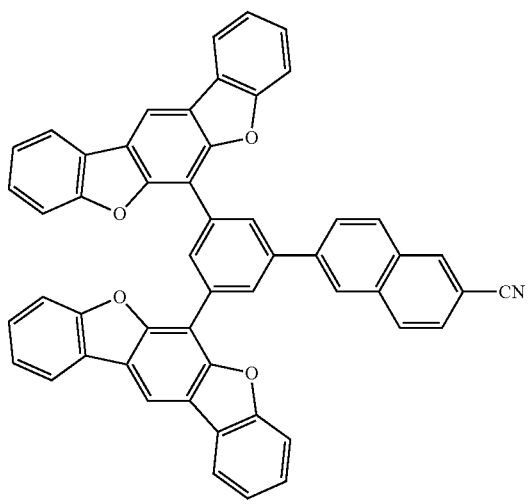
ET 9-40
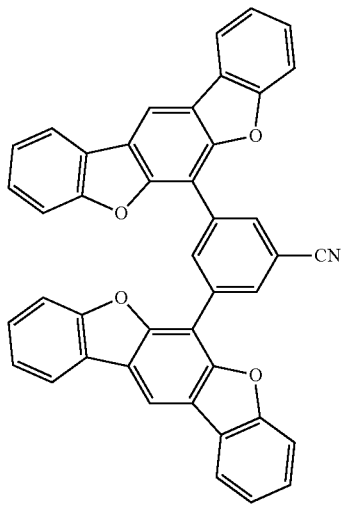

ET 9-41
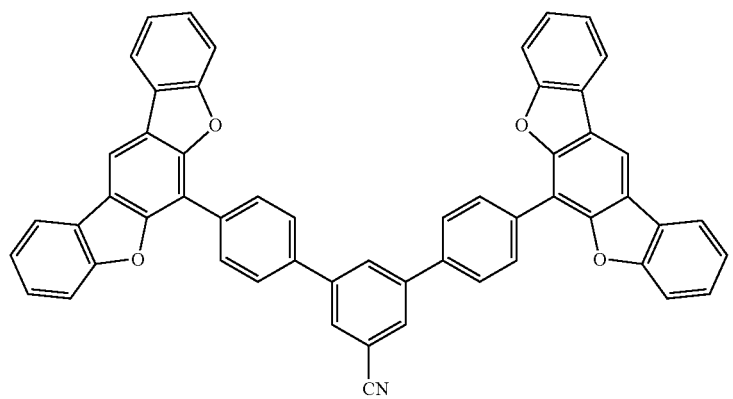
ET 9-42
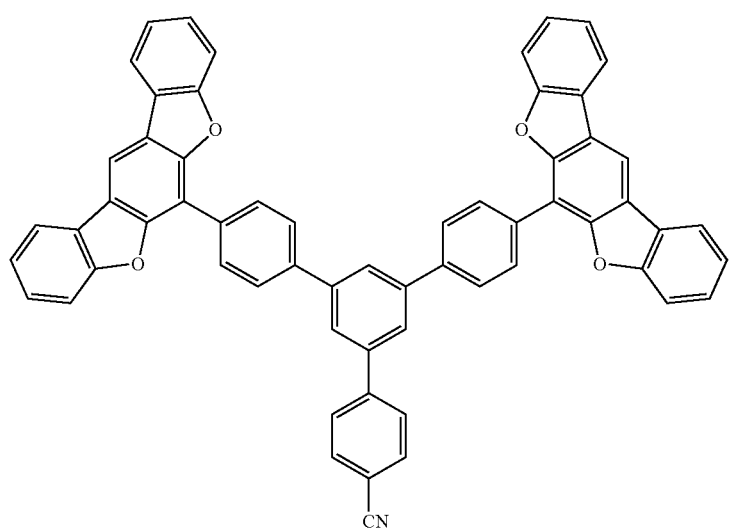
Specific examples of the oxygen-containing fused aromatic ring compounds shown by the formulas (10) to (12) are shown below.
ET 10-01
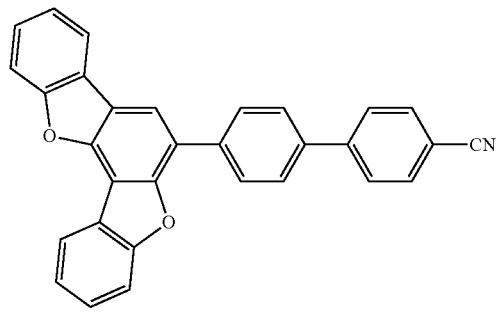
ET 10-02
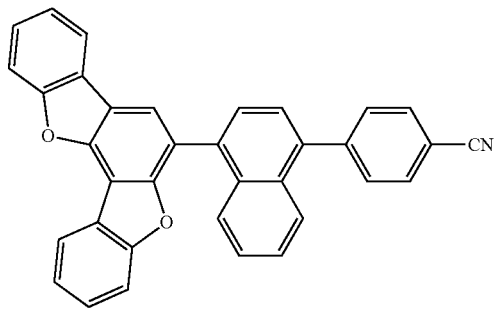

-continued
ET 10-03
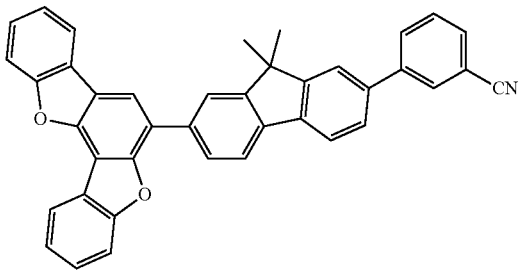
ET 10-04
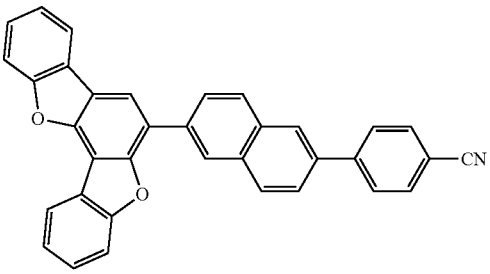
ET 10-05
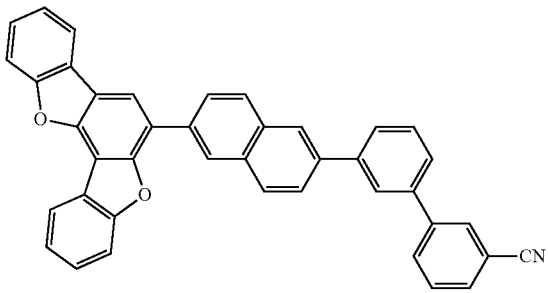
ET 10-06
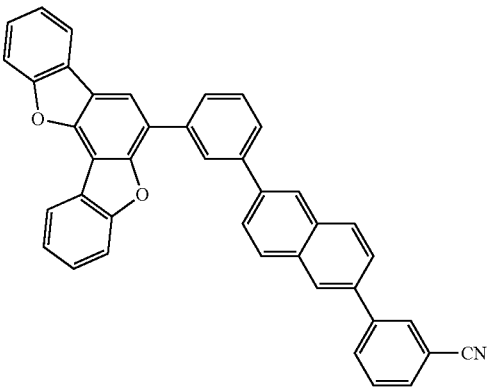
ET 10-07
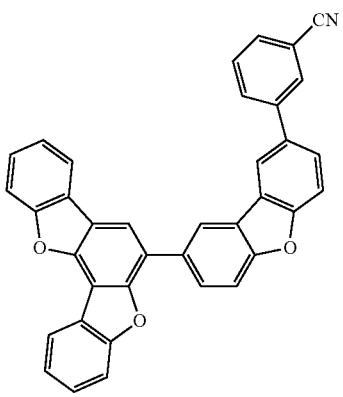
ET 10-08
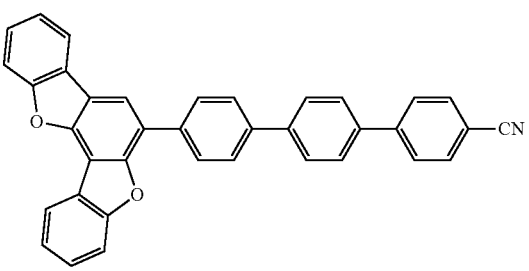
ET 10-09
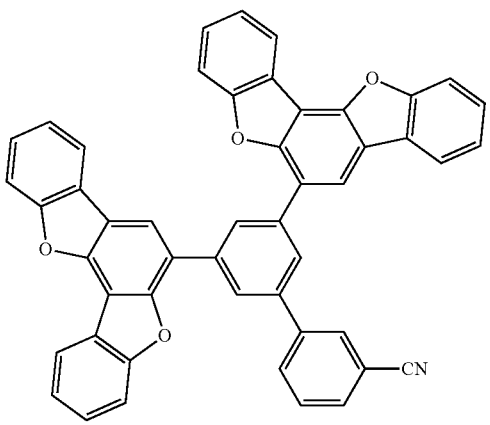
ET 11-01
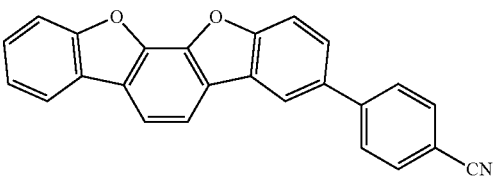

-continued
ET 11-02
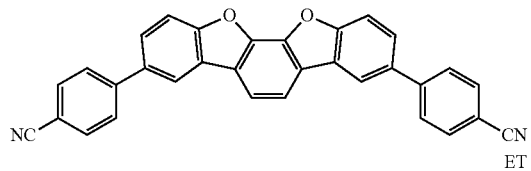
ET 11-03
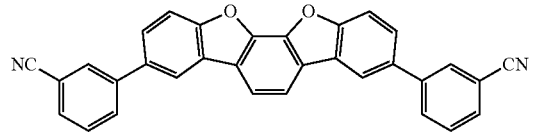
ET 11-04
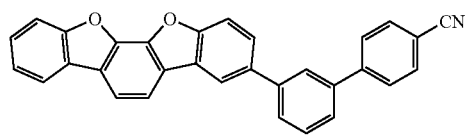
ET 11-05
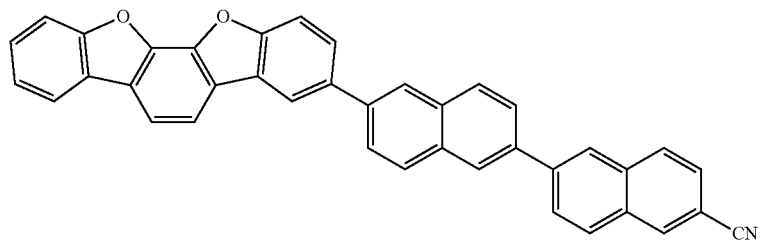
ET 11-06
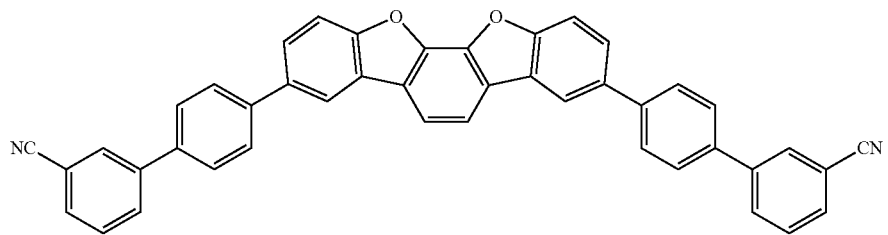
ET 11-07
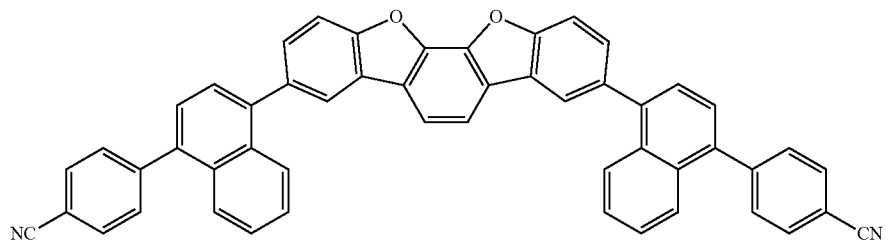
ET 11-08
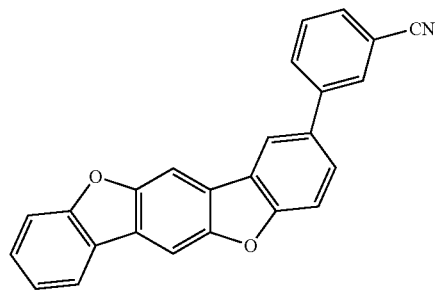
ET 12-01
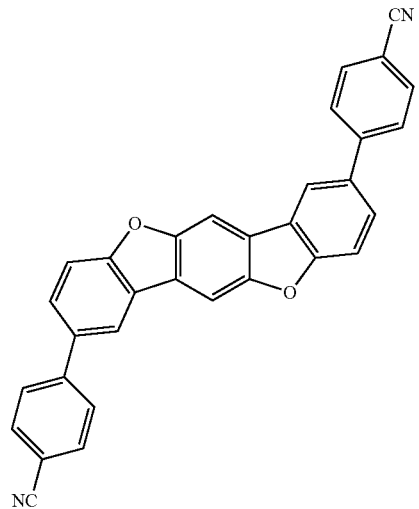
ET 12-02

-continued
ET 12-03
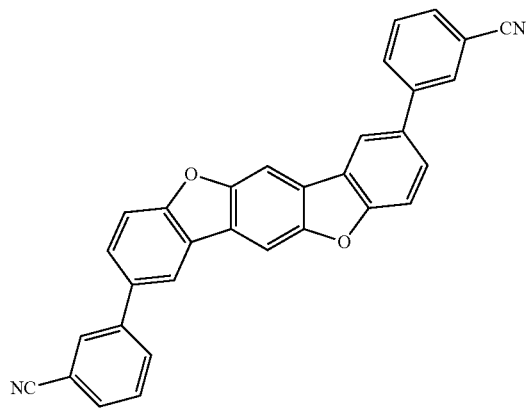
ET 12-04
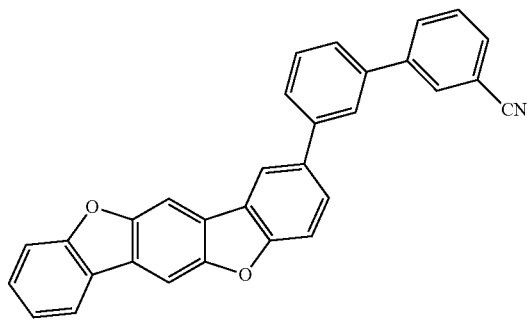
ET 12-05
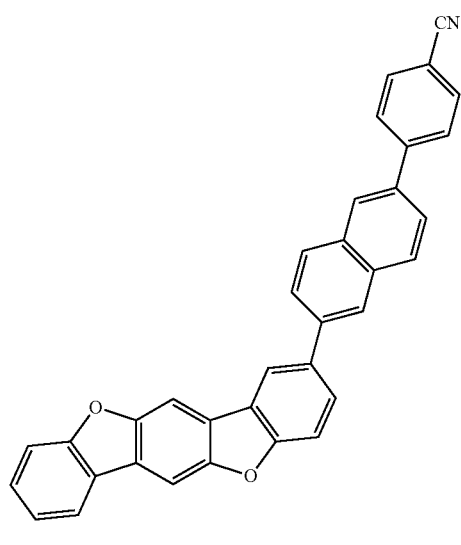
ET 12-06
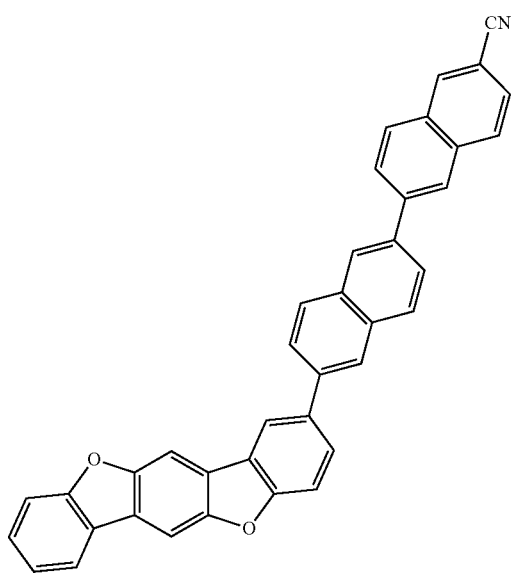
ET 12-07
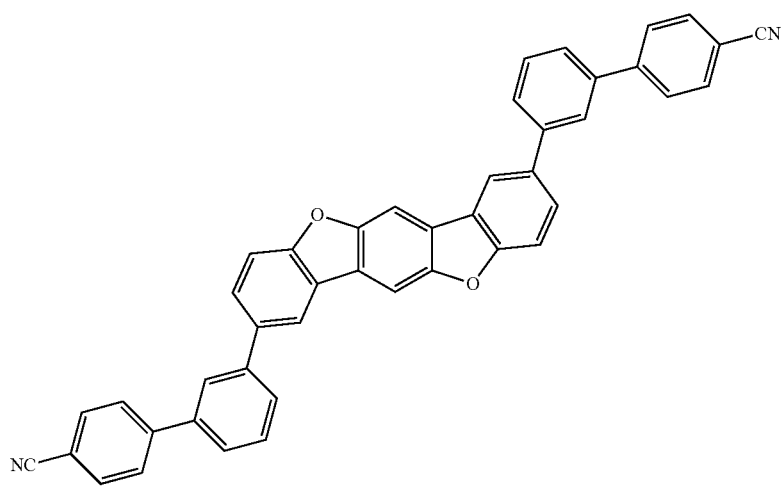

-continued
ET 12-08
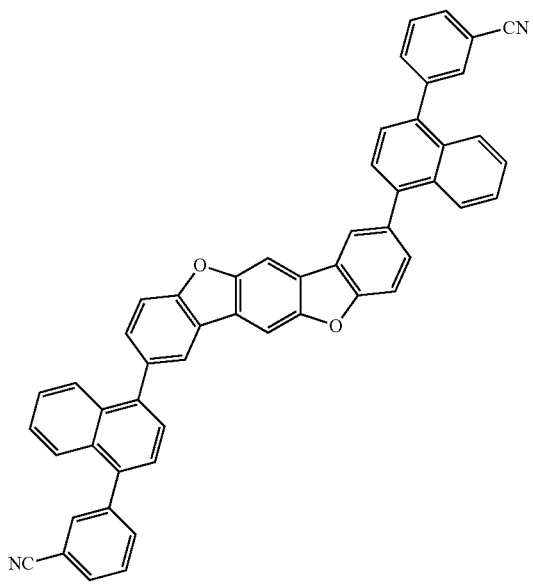
ET 12-09
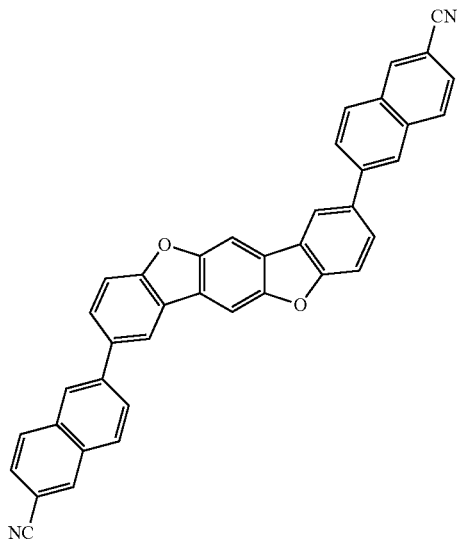
ET 12-10
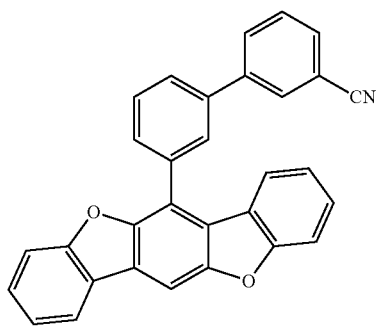
ET 12-11
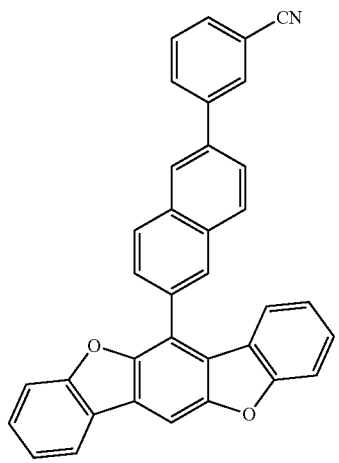
ET 12-12
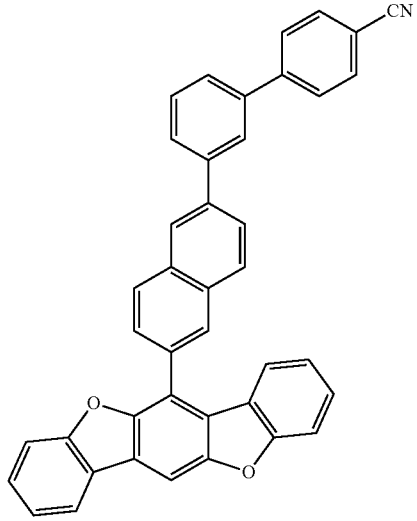
ET 12-13
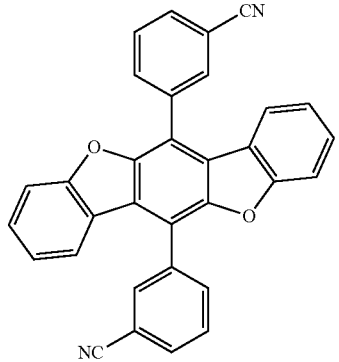

ET 12-14

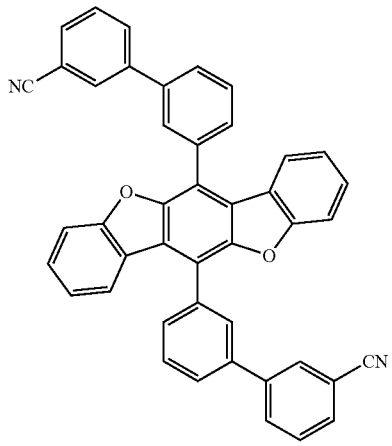

ET 12-15

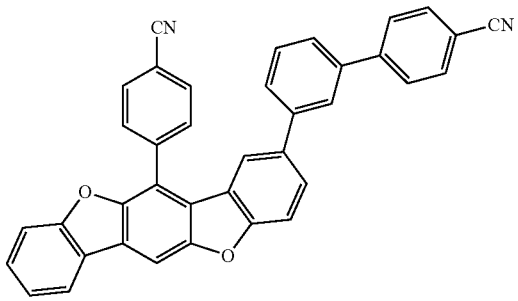

The organic EL device according to the invention utilizes the compound shown by the formula (ET) as an electron-transporting material. Note that the compound shown by the formula (ET) may also be used as various materials (including an electron-transporting material) for an organic EL device.

It is preferable that the barrier layer, the electron-injecting layer, or the electron-transporting layer (all of them is an electron-transporting region) that includes the compound used in the invention having a cyano group and an aromatic ring group further include a reducing dopant.

Examples of the reducing dopant include donor metals, donor metal compounds, and donor metal complexes. These reducing dopants may be used either individually or in combination of two or more.

Note that the term "reducing dopant" used herein refers to a material that donates electrons (i.e., electron donor material). The electron donor material is a material that interacts with an organic material that is included together with the electron donor material in the barrier layer, the electron-injecting layer, or the electron-transporting layer, or an organic material that is included in a layer adjacent to the barrier layer, the electron-injecting layer, or the electron-transporting layer, and produces radical anions, or a material that includes an electron donor radical.

The term "donor metal" used herein refers to a metal having a work function of 3.8 eV or less. The donor metal is preferably an alkali metal, an alkaline-earth metal, or a rare earth metal, and more preferably Cs, Li, Na, Sr, K, Mg, Ca, Ba, Yb, Eu, or Ce.

The term "donor metal compound" used herein refers to a compound that includes a donor metal. The donor metal compound is preferably a compound that includes an alkali metal, an alkaline-earth metal, or a rare earth metal, and more preferably a halide, an oxide, a carbonate, or a borate of these metals. For example, the donor metal compound is a compound shown by MOx (wherein M is a donor metal, and x is a number from 0.5 to 1.5), MFx (x is a number from 1 to 3), or $M(CO_3)x$ (x is a number from 0.5 to 1.5).

The term "donor metal complex" refers to a complex of a donor metal. The donor metal complex is preferably an organic metal complex of an alkali metal, an alkaline-earth metal, or a rare earth metal. The donor metal complex is preferably an organic metal complex shown by the following formula (I):

$$M(-Q)_n \quad (I)$$

wherein M is a donor metal, Q is a ligand (preferably a carboxylic acid derivative, a diketone derivative, or a quinolinic derivative), and n is an integer from 1 to 4.

Specific examples of the donor metal complex include the tungsten paddlewheel disclosed in JP-A-2005-72012, and the like. The phthalocyanine compound disclosed in JP-A-11-345687 wherein the central metal is an alkali metal or an alkaline-earth metal, may also be used as the donor metal complex.

The reducing dopant is preferably one substance or two or more substances selected from the group consisting of alkali metals, alkaline-earth metals, rare earth metals, alkali metal oxides, alkali metal halides, alkaline-earth metal oxides, alkaline-earth metal halides, rare earth metal oxides, rare earth metal halides, organic complexes of alkali metals, organic complexes of alkaline-earth metals, and organic complexes of rare earth metals, and more preferably an 8-quinolinol complex of an alkali metal.

A small-work-function metal-containing layer may be provided between the electron-transporting region and the cathode. The term "small-work-function metal-containing layer" used herein refers to a layer that includes a small-work-function metal or a small-work-function metal compound. The small-work-function metal-containing layer may be formed only of a small-work-function metal or a small-work-function metal compound, or may be formed by adding as a donor a small-work-function metal, a small-work-function metal compound, or a small-work-function metal complex to a material used to form the electron-transporting layer. The term "small-work-function metal" used herein refers to a metal that has a work function of 3.8 eV or less. Examples of the metal that has a work function of 3.8 eV or less include alkali metals, alkaline-earth metals, and the like. Examples of the alkali metals include Li, Na, K, Cs, and the like. Examples of the alkaline-earth metals include Mg, Ca, Sr, Ba, and the like. Further examples of the metal that has a work function of 3.8 eV or less include Yb, Eu, Ce, and the like. Examples of a preferable small-work-function metal compound include oxides, halides, carbonates, and borates of the small-work-function metals. Examples of the halides of the small-work-function metals include fluorides, chlorides, and bromides of the small-work-function metals. Among these, fluorides of the small-work-function metals are preferable. For example, LiF is preferably used. Examples of a preferable small-work-function metal complex include organic metal complexes of alkali metals, alkaline-earth metals, and rare earth metals.

The efficiency of a blue fluorescent layer is remarkably improved by utilizing the TTF phenomenon. Note that the luminous efficiency of a green fluorescent layer or a red fluorescent layer can also be improved by confining the triplet energy within the emitting layer.

In the organic EL device according to the invention, it is preferable that the emitting layer include at least one of an anthracene derivative shown by the following formula (4) and a pyrene derivative shown by the following formula (5) as the host.

(Anthracene Derivative)

The anthracene derivative is shown by the following formula (4):

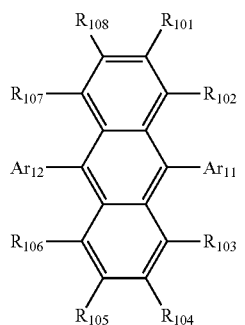

(4)

wherein $Ar_{11}$ and $Ar_{12}$ are independently a substituted or unsubstituted monocyclic aromatic ring group having 5 to 50 ring atoms, a substituted or unsubstituted fused aromatic ring group having 8 to 50 ring atoms, or a combination of the monocyclic aromatic ring group and the fused aromatic ring group, and $R_{101}$ to $R_{108}$ are independently a group selected from a hydrogen atom, a substituted or unsubstituted monocyclic aromatic ring group having 5 to 50 ring atoms, a substituted or unsubstituted fused aromatic ring group having 8 to 50 ring atoms, a group constituted of a combination of the monocyclic aromatic ring group and the fused aromatic ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

The term "monocyclic aromatic ring group" in the formula (4) refers to a group that includes only a cyclic structure that does not have a fused structure.

Specific examples of a preferable monocyclic aromatic ring group having 5 to 50 (preferably 5 to 30, and more preferably 5 to 20) ring atoms include the aryl groups mentioned above in connection with the aromatic ring group and a heterocyclic group (e.g., a pyridyl group, a pyrazyl group, a pyrimidyl group, a triazinyl group, a furyl group, and a thienyl group).

Among these, a phenyl group, a biphenyl group, and a terphenyl group are preferable.

The term "fused aromatic ring group" in the formula (4) refers to a group in which two or more rings are fused.

Specific examples of a preferable fused aromatic ring group having 8 to 50 (preferably 8 to 30, and more preferably 8 to 20) ring atoms include the fused aryl groups mentioned above in connection with the aromatic ring group and a fused heterocyclic group (e.g., a benzofuranyl group, a benzothiophenyl group, an indolyl group, a dibenzofuranyl group, a dibenzothiophenyl group, a carbazolyl group, a quinolyl group, and a phenanthrolinyl group).

Among these, a naphthyl group, a phenanthryl group, an anthryl group, a 9,9-dimethylfluorenyl group, a fluoranthenyl group, a benzanthryl group, a dibenzothiophenyl group, a dibenzofuranyl group, and a carbazolyl group are preferable.

Specific examples of the alkyl group having 1 to 50 carbon atoms, the cycloalkyl group having 3 to 50 ring carbon atoms, and the substituted or unsubstituted silyl group include those mentioned above in connection with the formula (1).

The alkoxy group having 1 to 50 carbon atoms is a group shown by —OY. Examples of Y include the alkyl groups mentioned above in connection with the formula (1).

The aryloxy group having 6 to 50 ring carbon atoms is a group shown by —OAr. Examples of Ar include the aryl groups mentioned above in connection with the formula (1).

The aralkyl group having 7 to 50 carbon atoms is a group shown by —Y—Z. Examples of Y include alkylene groups that correspond to the alkyl groups mentioned above. Examples of Z include the aryl groups mentioned above. The number of carbon atoms of the aralkyl group is preferably 7 to 50 (the number of carbon atoms of the aryl moiety is 6 to 49 (preferably 6 to 30, more preferably 6 to 20, and particularly preferably 6 to 12), and the number of carbon atoms of the alkyl moiety is 1 to 44 (preferably 1 to 30, more preferably 1 to 20, still more preferably 1 to 10, and particularly preferably 1 to 6)). Examples of the aralkyl group include a benzyl group, a phenylethyl group, and a 2-phenylpropan-2-yl group.

A substituent of "the substituted or unsubstituted" for $Ar_{11}$, $Ar_{12}$, and $R_{101}$ to $R_{108}$ is preferably a monocyclic aromatic ring group, a fused aromatic ring group, an alkyl group, a cycloalkyl group, a silyl group, an alkoxy group, a cyano group, or a halogen atom (particularly a fluorine atom), and particularly preferably a monocyclic aromatic ring group or a fused aromatic ring group. Specific examples of a preferable substituent include those mentioned above in connection with each group in the formulas (1) and (4).

The anthracene derivative shown by the formula (4) is preferably any of the following anthracene derivatives (A), (B), and (C). The anthracene derivative is selected depending on the configuration and the desired properties of the organic EL device to which the derivative is applied.

(Anthracene Derivative (A))

The anthracene derivative (A) is an anthracene derivative shown by the formula (4) wherein $Ar_{11}$ and $Ar_{12}$ are independently a substituted or unsubstituted fused aromatic ring group having 8 to 50 ring atoms. The anthracene derivative (A) may be an anthracene derivative wherein $Ar_{11}$ and $Ar_{12}$ are identical substituted or unsubstituted fused aromatic ring groups, or may be an anthracene derivative wherein $Ar_{11}$ and $Ar_{12}$ are different substituted or unsubstituted fused aromatic ring groups.

The anthracene derivative (A) is preferably an anthracene derivative shown by the formula (4) wherein $Ar_{11}$ and $Ar_{12}$ are different substituted or unsubstituted fused aromatic ring groups (including a difference in position of a substituent). Specific examples of a preferable fused aromatic ring group include those mentioned above. A naphthyl group, a phenanthryl group, a benzanthryl group, a 9,9-dimethylfluorenyl group, and a dibenzofuranyl group are particularly preferable as the fused aromatic ring group.

(Anthracene Derivative (B))

The anthracene derivative (B) is an anthracene derivative shown by the formula (4) wherein one of $Ar_{11}$ and $Ar_{12}$ is a substituted or unsubstituted monocyclic aromatic ring group having 5 to 50 ring atoms, and the other of $Ar_{11}$ and $Ar_{12}$ is a substituted or unsubstituted fused aromatic ring group having 8 to 50 ring atoms.

It is preferable that $Ar_{12}$ be a naphthyl group, a phenanthryl group, a benzanthryl group, a 9,9-dimethylfluorenyl group, or a dibenzofuranyl group, and $Ar_{11}$ be a phenyl group substituted with a monocyclic aromatic ring group or a fused aromatic ring group.

Specific examples of a preferable monocyclic aromatic ring group and a preferable fused aromatic ring group include those mentioned above.

It is also preferable that $Ar_{12}$ be a fused aromatic ring group, and $Ar_{11}$ be an unsubstituted phenyl group. In this case, a phenanthryl group, a 9,9-dimethylfluorenyl group, a dibenzofuranyl group, and a benzanthryl group are particularly preferable as the fused aromatic ring group.

(Anthracene Derivative (C))

The anthracene derivative (C) is an anthracene derivative shown by the formula (4) wherein $Ar_{11}$ and $Ar_{12}$ are independently a substituted or unsubstituted monocyclic aromatic ring group having 5 to 50 ring atoms.

It is preferable that $Ar_{11}$ and $Ar_{12}$ be substituted or unsubstituted phenyl groups.

It is more preferable that $Ar_{11}$ be an unsubstituted phenyl group, and $Ar_{12}$ be a phenyl group substituted with a monocyclic aromatic ring group or a fused aromatic ring group, or $Ar_{11}$ and $Ar_{12}$ be independently a phenyl group substituted with a monocyclic aromatic ring group or a fused aromatic ring group.

Specific examples of a preferable monocyclic aromatic ring group and a preferable fused aromatic ring group as a substituent include those mentioned above. The monocyclic aromatic ring group as a substituent is preferably a phenyl group or a biphenyl group, and the fused aromatic ring group as a substituent is preferably a naphthyl group, a phenanthryl group, a 9,9-dimethylfluorenyl group, a dibenzofuranyl group, or a benzanthryl group.

(Pyrene Derivative)

The pyrene derivative is shown by the following formula (5):

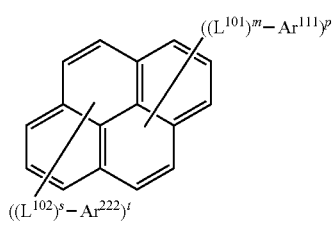

(5)

wherein $Ar^{111}$ and $Ar^{222}$ are independently a substituted or unsubstituted aryl group having 6 to 30 ring carbon atoms, $L^{101}$ and $L^{102}$ are independently a substituted or unsubstituted divalent aryl group having 6 to 30 ring carbon atoms, or a heterocyclic group, m is an integer from 0 to 1, p is an integer from 1 to 4, s is an integer from 0 to 1, and t is an integer from 0 to 3.

$L^{101}$ or $Ar^{111}$ is bonded to one of positions 1 to 5 of pyrene, and $L^{102}$ or $Ar^{222}$ is bonded to one of positions 6 to 10 of pyrene.

$L^{101}$ and $L^{102}$ in the formula (5) are preferably divalent aryl groups selected from a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, and a combination thereof.

Examples of a substituent include those mentioned above in connection with the substituent for "the substituted or unsubstituted" of the formula (1). A substituent that may substitute $L^{101}$ and $L^{102}$ is preferably an alkyl group having 1 to 20 carbon atoms.

m in the formula (5) is preferably an integer from 0 to 1. n in the formula (5) is preferably an integer from 1 to 2. s in the formula (5) is preferably an integer from 0 to 1.

t in the formula (5) is preferably an integer from 0 to 2.

Examples of the aryl group represented by $Ar^{111}$ and $Ar^{222}$ include those mentioned above in connection with the formula (1).

$Ar^{111}$ and $Ar^{222}$ are preferably substituted or unsubstituted aryl groups having 6 to 20 ring carbon atoms, and more preferably substituted or unsubstituted aryl groups having 6 to 16 ring carbon atoms. Specific examples of a preferable aryl group include a phenyl group, a naphthyl group, a phenanthryl group, a fluorenyl group, a biphenyl group, an anthryl group, and a pyrenyl group.

The emitting layer that includes the anthracene derivative shown by the formula (4) or the pyrene derivative shown by the formula (5) is preferably in contact with the barrier layer, the electron-injecting layer, or the electron-transporting layer that includes the compound shown by the formula (1). It is considered that the luminous efficiency can be improved by utilizing the TTF phenomenon when the emitting layer is in contact with the barrier layer, the electron-injecting layer, or the electron-transporting layer that includes the compound shown by the formula (1).

The emitting layer included in the organic EL device according to the invention may include an emitting dopant (phosphorescent dopant and/or fluorescent dopant).

The term "fluorescent dopant" used herein refers to a compound that emits light due to singlet excitons. The fluorescent dopant is preferably selected from amine compounds, aromatic compounds, chelate complexes such as a tris(8-quinolinolato)aluminum complex, coumarin derivatives, tetraphenylbutadiene derivatives, bisstyrylarylene derivatives, oxadiazole derivatives, and the like depending on the desired emission color. Among these, styrylamine compounds, styryldiamine compounds, arylamine compounds, aryldiamine compounds, and aromatic compounds are more preferable, and fused polycyclic amine derivatives and aromatic compounds are still more preferable. These fluorescent dopants may be used either individually or in combination.

A compound shown by the following formula (12) is preferable as the fused polycyclic amine derivative:

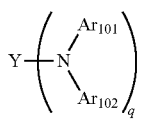

(12)

wherein Y is a substituted or unsubstituted fused aryl group having 10 to 50 ring carbon atoms, and $Ar_{101}$ and $Ar_{102}$ are independently a substituted or unsubstituted aryl group having 6 to 50 ring carbon atoms, or a substituted or unsubstituted heterocyclic group having 5 to 50 ring atoms.

Specific examples of Y include the fused aryl groups mentioned above. Y is preferably a substituted or unsubstituted anthryl group, a substituted or unsubstituted pyrenyl group, or a substituted or unsubstituted chrysenyl group.

q is an integer from 1 to 4. q is preferably an integer from 1 to 2.

In the formula (12), examples of the alkyl group, the alkoxy group, the aryl group, the aryloxy group, and the heterocyclic group include those mentioned above.

A fluoranthene compound shown by the following formula (13) is preferable as the aromatic compound:

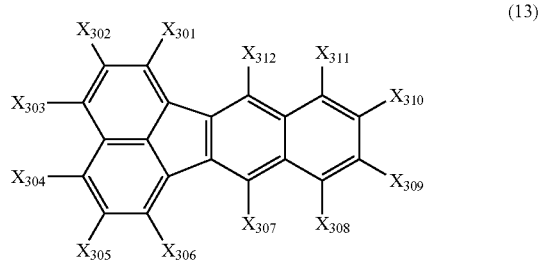

(13)

wherein $X_{301}$ to $X_{306}$ and $X_{308}$ to $X_{311}$ are independently selected from a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 10 carbon atoms, a substituted or unsubstituted cycloalkyl group having 3 to 8 ring carbon atoms, a substituted or unsubstituted alkoxy group having 1 to 20 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 5 to 50 ring carbon atoms, a substituted or unsubstituted alkoxycarbonyl group having 2 to 50 carbon atoms, an amino group substituted with a substituted or unsubstituted aryl group having 6 to 30 ring carbon atoms, a halogen atom, a cyano group, a nitro group, a hydroxyl group, and a carboxyl group, and $X_{307}$ and $X_{312}$ are independently selected from a substituted or unsubstituted aryl group having 6 to 30 ring carbon atoms, a substituted or unsubstituted heterocyclic group having 5 to 30 ring atoms, a substituted or unsubstituted alkyl group having 1 to 20 carbon atoms, and a substituted or unsubstituted cycloalkyl group having 3 to 8 ring carbon atoms, provided that $X_{303}$ and $X_{304}$ differ from each other, and adjacent substituents among $X_{301}$ to $X_{312}$ may bond to each other to form a substituted or unsubstituted saturated or unsaturated cyclic structure.

$X_{303}$ or $X_{304}$ in the formula (13) is preferably a substituted or unsubstituted aryl group having 6 to 30 ring carbon atoms. A substituent for "the substituted or unsubstituted" in the formula (13) is preferably a cyano group or a halogen atom.

In the formula (13), examples of the aryl group, the heterocyclic group, the alkyl group, the cycloalkyl group, the alkoxy group, the aralkyl group, the aryloxy group, the arylthio group, the alkoxycarbonyl group, and the halogen atom include those mentioned above.

The substrate, the anode, the cathode, the hole-injecting layer, the hole-transporting layer, and the like included in the organic EL device according to the invention may be appropriately formed using the materials disclosed in WO2008/023759A1, WO2008/023759A1, WO2009/107596A1, WO2009/081857A1, US2009/0243473A1, US2008/0014464A1, US2009/0021160A1, and the like.

EXAMPLES

The following compounds were used in the examples and comparative examples.

A-1

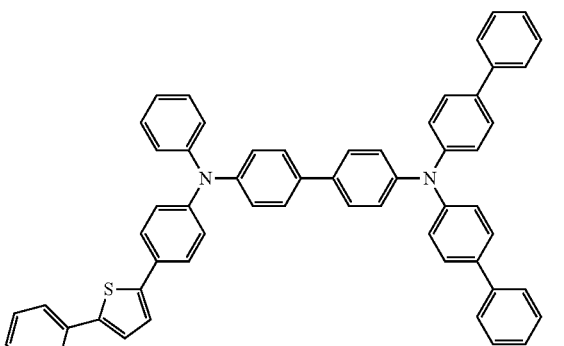

A-2

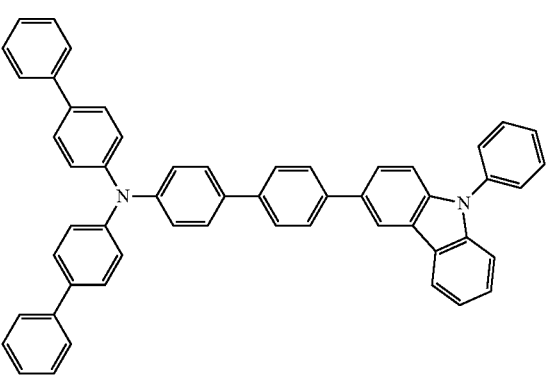

BH-1

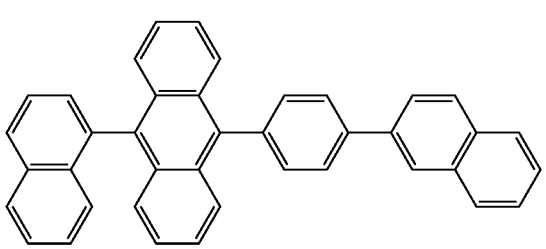

-continued

BD-1
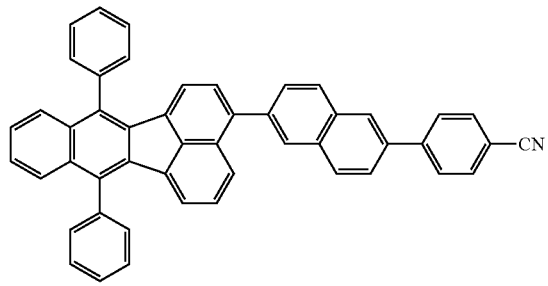

BD-2
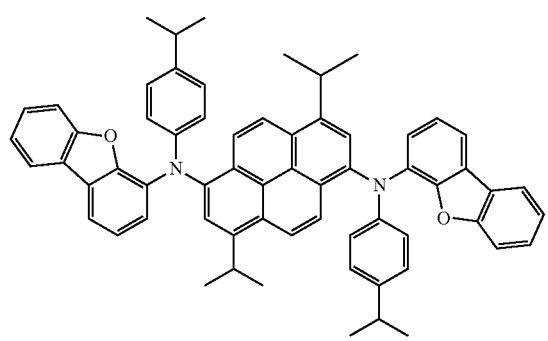

C-1
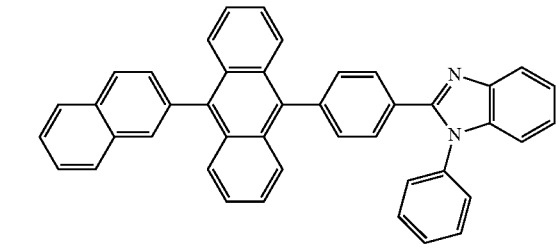

C-2
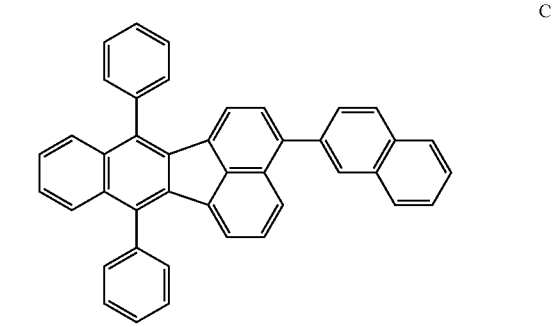

C-3
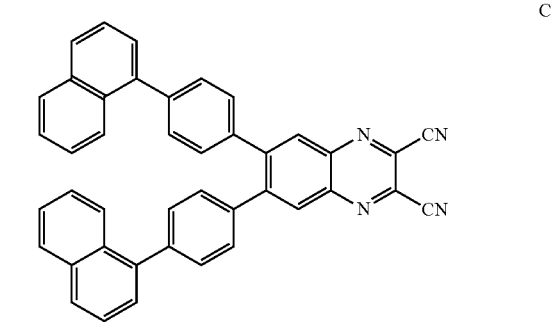

-continued

C-4
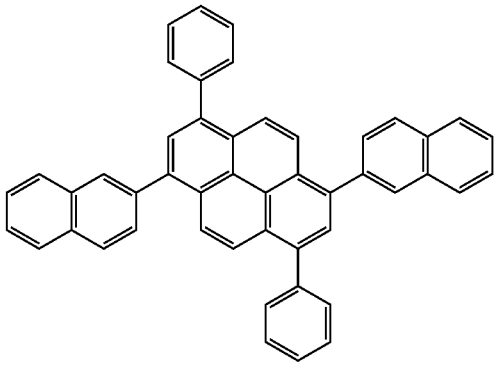

C-5
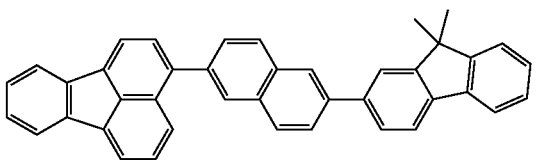

C-6
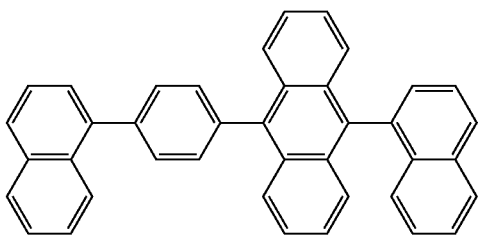

C-7
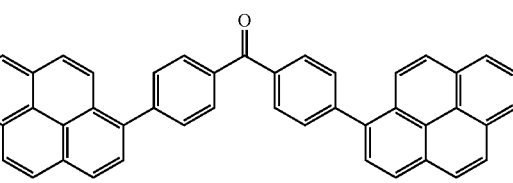

Example 1

A glass substrate (25×75×1.1 mm) provided with an ITO transparent electrode (anode) (manufactured by GEO-MATEC Co, Ltd.) was subjected to ultrasonic cleaning for 5 minutes in isopropyl alcohol, and then subjected to UV ozone cleaning for 30 minutes. The glass substrate with transparent electrode lines was mounted on the substrate holder of a vacuum deposition apparatus, and the compound A-1 was deposited to form a 50 nm-thick film so as to cover the surface of the transparent electrode on which the transparent electrode lines were formed. The compound A-2 was deposited on the film A-1 to form a film A-2 having a thickness of 45 nm. The compounds BH-1 and BD-1 were deposited on the film A-2 to a thickness of 25 nm (thickness ratio: 20:1) to form a blue-emitting layer. A compound ET 1-01 was deposited on the emitting layer to a thickness of 25 nm to form an electron-transporting layer. LiF was deposited on the electron-transporting layer to a thickness of 1 nm. Al was deposited on the LiF film to a thickness of 150 nm to form a metal cathode. An organic EL device was thus fabricated.

The drive voltage, the current efficiency, and the half life of the organic EL device were measured and evaluated by the following methods. The results are shown in Table 1.

(1) Drive Voltage (V) and Current Efficiency (L/J)

The drive voltage (V) and the luminance (L) when causing a direct current of 10 mA/cm$^2$ to flow through the organic EL device were measured. The current efficiency (L/J) was calculated from the measured values.

(2) Half Life

The organic EL device was driven at a current density of 8 mA/cm$^2$. A change in luminance with time was measured, and the time required for the luminance to decrease by 50% was determined.

Examples 2 to 9 and Comparative Examples 1 to 3

An organic EL device was fabricated and evaluated in the same manner as in Example 1, except that the compound shown in Table 1 was used as the material for the electron-transporting layer instead of the compound ET 1-01. The results are shown in Table 1.

TABLE 1

| | Electron-transporting material | Drive voltage [V] | Current efficiency [cd/A] | Half life [h] |
|---|---|---|---|---|
| Example 1 | ET 1-01 | 4.2 | 4.4 | 6000 |
| Example 2 | ET 1-02 | 3.7 | 6.9 | 5000 |
| Example 3 | ET 1-19 | 3.8 | 7.4 | 7000 |
| Example 4 | ET 1-22 | 3.3 | 7.6 | 5000 |
| Example 5 | ET 1-23 | 3.3 | 7.8 | 5000 |
| Example 6 | ET 1-32 | 3.8 | 7.4 | 6000 |
| Example 7 | ET 1-36 | 3.7 | 8.5 | 5000 |
| Example 8 | ET 1-45 | 3.9 | 6.7 | 7000 |
| Example 9 | ET 1-48 | 4.1 | 6.1 | 7500 |
| Com. Ex. 1 | C-1 | 5.0 | 4.2 | 2500 |
| Com. Ex. 2 | C-2 | 6.1 | 4.5 | 3000 |
| Com. Ex. 3 | C-3 | 7.1 | 3.2 | 1000 |

As shown in Table 1, a decrease in drive voltage, an increase in efficiency, and an increase in lifetime were achieved when using the compound including a cyano group and an aromatic ring group as the electron-transporting material.

As is clear from the comparison between Examples 1 to 9 and Comparative Examples 1 and 2, a decrease in drive voltage, an increase in efficiency, and an increase in lifetime were advantageously achieved when using the electron-transporting material according to the invention including a cyano substituent group as compared with the case of using a nitrogen-containing heterocyclic derivative.

As is clear from the comparison between Examples 1 to 9 and Comparative Example 3, a decrease in drive voltage, an increase in efficiency, and an increase in lifetime were advantageously achieved when using the electron-transporting material including a cyano group and an aromatic ring group (even if a single material was used), while an increase in voltage was observed when using the electron-transporting material including a cyano group and a nitrogen-containing heterocyclic ring.

When a cyano group is introduced into a nitrogen-containing heterocyclic ring, the cyano group hinders transport of electrons due to a high electron-trapping capability, and increases the drive voltage. It was confirmed that a cyano group that is introduced into a specific aromatic ring group serves as an electron-injecting site without hindering transport of electrons, so that a decrease in drive voltage and an increase in lifetime can be achieved. It is considered that the hole resistance was significantly improved since a nitrogen-containing heterocyclic derivative that exhibits poor hole resistance was not used, so that the lifetime increased.

Example 10

A glass substrate (25×75×1.1 mm) provided with an ITO transparent electrode (anode) (manufactured by GEO-MATEC Co, Ltd.) was subjected to ultrasonic cleaning for 5 minutes in isopropyl alcohol, and then subjected to UV ozone cleaning for 30 minutes. The glass substrate with transparent electrode lines was mounted on the substrate holder of a vacuum deposition apparatus, and the compound A-1 was deposited to form a 50 nm-thick film so as to cover the surface of the transparent electrode on which the transparent electrode lines were formed. The compound A-2 was deposited on the film A-1 to form a film A-2 having a thickness of 45 nm. The compounds BH-1 and BD-1 were deposited on the film A-2 to a thickness of 25 nm (thickness ratio: 20:1) to form a blue-emitting layer. The compound ET1-01 and lithium quinolinolate (Liq) were deposited on the emitting layer in a thickness ratio of 1:1 to form an electron-transporting layer having a thickness of 25 nm. Al was deposited on the electron-transporting layer to a thickness of 150 nm to form a metal cathode. An organic EL device was thus fabricated.

The drive voltage, the current efficiency, and the half life of the organic EL device were evaluated as described above. The results are shown in Table 2.

Examples 11 to 18

An organic EL device was fabricated and evaluated in the same manner as in Example 10, except that the compound shown in Table 2 was used as the material for the electron-transporting layer instead of the compound ET1-01. The results are shown in Table 2.

TABLE 2

| | Electron-transporting material | Drive voltage [V] | Current efficiency [cd/A] | Half life [h] |
|---|---|---|---|---|
| Example 10 | ET 1-1 | 4.0 | 5.8 | 8000 |
| Example 11 | ET 1-2 | 3.5 | 8.7 | 7000 |
| Example 12 | ET 1-19 | 3.7 | 7.6 | 9000 |
| Example 13 | ET 1-22 | 3.3 | 8.3 | 7000 |
| Example 14 | ET 1-23 | 3.3 | 8.3 | 7000 |
| Example 15 | ET 1-32 | 3.5 | 8.7 | 8000 |
| Example 16 | ET 1-36 | 3.4 | 9.5 | 7000 |
| Example 17 | ET 1-45 | 3.7 | 7.9 | 9000 |
| Example 18 | ET 1-48 | 3.6 | 7.8 | 9500 |

As is clear from the results shown in Table 2, it was confirmed that an organic EL device that can be driven at a low voltage and exhibits a high efficiency and a long lifetime can also be obtained when using the electron-transporting material used for the electron-transporting region of the organic EL device according to the invention in combination with an organic complex of an alkali metal.

Synthesis Example 1

Synthesis of 6-hydroxynaphthalen-2-ylboronic acid

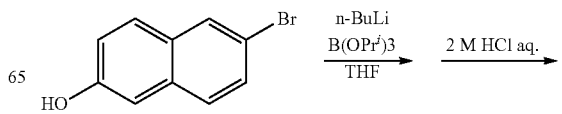

-continued

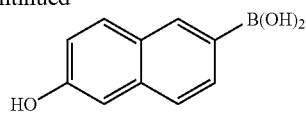

6-Bromo-2-naphthol (5.58 g) was dissolved in dehydrated tetrahydrofuran (125 ml) in an argon atmosphere. After cooling the solution to −70° C., a hexane solution of n-butyllithium (33 ml, 55 mmol) was slowly added dropwise to the solution over 30 minutes. The mixture was stirred at −70° C. for 1.5 hours. After the addition of triisopropyl borate (11.5 ml), the mixture was stirred at −70° C. for 30 minutes. The mixture was then stirred for 3 hours while allowing the mixture to gradually return to room temperature. After the addition of 2 M hydrochloric acid (100 ml) to the reaction mixture, the mixture was stirred at room temperature for 2 hours. The reaction solution was separated, and the aqueous layer was extracted with ethyl acetate. The organic layers were combined, washed with a saturated sodium chloride solution, dried over anhydrous sodium sulfate, and concentrated under reduced pressure. The residue was washed with dichloromethane in a suspended state to obtain 4.02 g of the target 6-hydroxynaphthalen-2-ylboronic acid (yield: 85%).

Synthesis Example 2

Synthesis of 3'-bromo-4-cyanobiphenyl

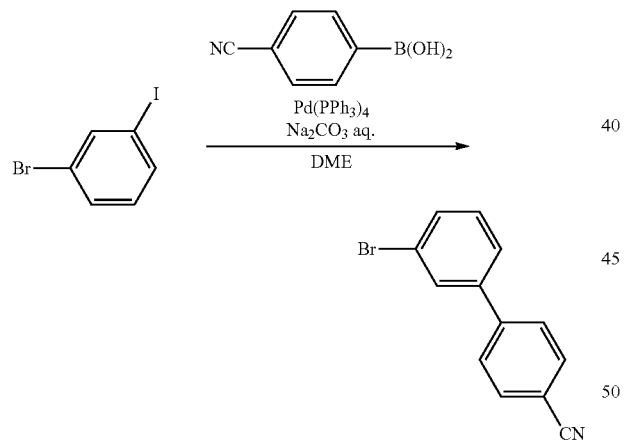

A mixture of 3-bromoiodobenzene (10.2 g), 4-cyanophenylboronic acid (4.4 g), tetrakis(triphenylphosphine)palladium(0) (1.04 g), 1,2-dimethoxyethane (90 ml), and a 2 M sodium carbonate aqueous solution (45 ml) was heated and refluxed for 3 hours in an argon atmosphere. The reaction mixture was then cooled to room temperature. After the addition of water, the mixture was stirred for 1 hour. The reaction solution was then cooled to room temperature, extracted with ethyl acetate, washed with a saturated sodium chloride solution, dried over anhydrous sodium sulfate, and concentrated under reduced pressure. The residue was purified by silica gel column chromatography to obtain 4.1 g of the target 3'-bromo-4-cyanobiphenyl (yield: 53%).

Synthesis Example 3

Synthesis of 3'-bromo-3-cyanobiphenyl

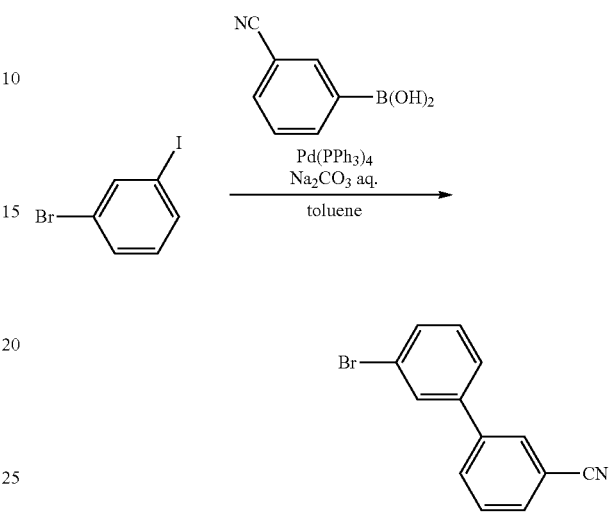

The target 3'-bromo-3-cyanobiphenyl was synthesized in the same manner as in Synthesis Example 2, except that 3-cyanophenylboronic acid was used instead of 4-cyanophenylboronic acid (yield: 44%).

Synthesis Example 4

Synthesis of 6-(4'-cyanobiphenyl-3-yl)naphthalen-2-yl trifluoromethanesulfonate 6-(4'-Cyanobiphenyl-3-yl)naphthalen-2-yl trifluoromethanesulfonate was Synthesized in Accordance with the Following Synthesis Scheme

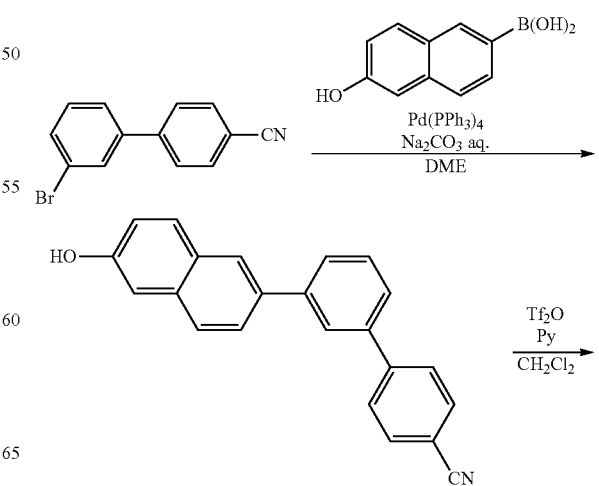

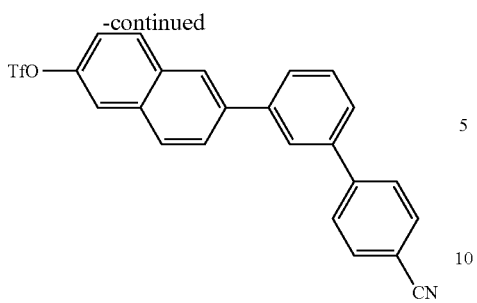

(4-1) Synthesis of 6-(4'-cyanobiphenyl-3-yl)-2-naphthol

A mixture of 3'-bromo-4-cyanobiphenyl obtained in Synthesis Example 2 (4.07 g), 6-hydroxynaphthalen-2-ylboronic acid obtained in Synthesis Example 1 (3.26 g), tetrakis(triphenylphosphine)palladium(0) (0.55 g), 1,2-dimethoxyethane (48 ml), and a 2 M sodium carbonate aqueous solution (24 ml) was heated and refluxed for 4 hours in an argon atmosphere. The reaction mixture was cooled to room temperature, and neutralized using 2 M hydrochloric acid. A precipitate produced by adding toluene to the mixture was filtered off, and washed with ethyl acetate and toluene. The filtrate was extracted with toluene and ethyl acetate, washed with a saturated sodium chloride solution, dried over anhydrous magnesium sulfate, and concentrated under reduced pressure. The residue was washed with a hexane-ethyl acetate mixture and methanol. The residue was combined with the solid, and washed with toluene to obtain 4.5 g of the target 6-(4'-cyanobiphenyl-3-yl)-2-naphthol (yield: 89%).

(4-2) Synthesis of 6-(4'-cyanobiphenyl-3-yl)naphthalen-2-yl trifluoromethanesulfonate Trifluoromethanesulfonic anhydride (4.6 ml) was added to a mixture of 6-(4'-cyanobiphenyl-3-yl)-2-naphthol (4.5 g), pyridine (4.6 ml), and dichloromethane (100 ml) at 0° C. in an argon atmosphere. The mixture was stirred for 1 hour. The reaction mixture was heated to room temperature, and stirred for 30 minutes. The reaction mixture was made acidic using 2 M hydrochloric acid, extracted with dichloromethane, dried over anhydrous magnesium sulfate, and concentrated under reduced pressure. The residue was purified by silica gel column chromatography to obtain 5.7 g of the target 6-(4'-cyanobiphenyl-3-yl)naphthalen-2-yl trifluoromethanesulfonate (yield: 90%).

Synthesis Example 5

Synthesis of benzo[g]chrysene-10-boronic acid

Benzo[g]chrysene-10-boronic acid was synthesized in accordance with the following synthesis scheme.

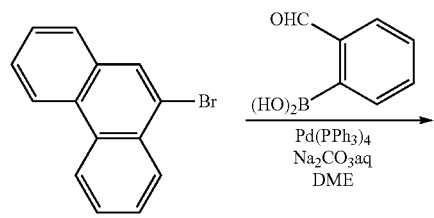

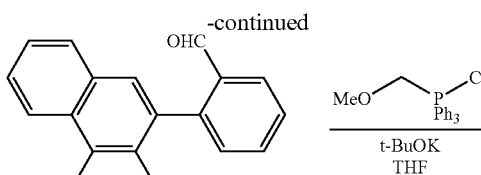

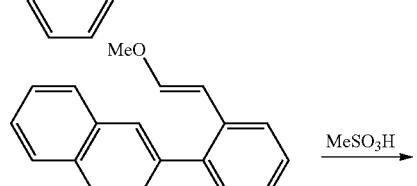

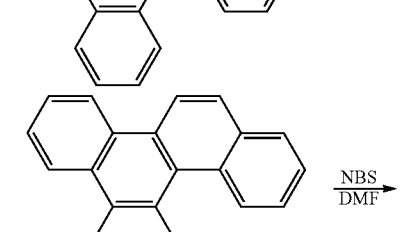

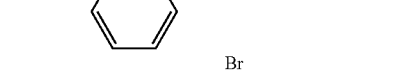

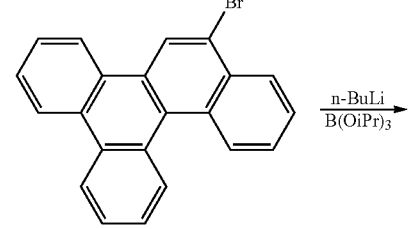

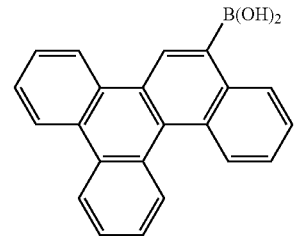

(5-1) Synthesis of 9-(2-formylphenyl)phenanthrene

A flask was charged with 9-bromophenanthrene (25.7 g), 2-formylphenylboronic acid (16.5 g), and tetrakis(triphenylphosphine)palladium(0) (2.31 g) in an argon atmosphere. After the addition of 1,2-dimethoxyethane (340 ml), and a 2 M sodium carbonate aqueous solution (170 ml), the mixture was heated and refluxed with stirring for 8 hours. After cooling the mixture to room temperature, the aqueous layer was removed. The organic layer was washed with water and a saturated sodium chloride solution, and dried over magnesium sulfate. After removing magnesium sulfate by filtration, the organic layer was concentrated. The residue was purified by silica gel column chromatography to obtain 25.0 g of the target 9-(2-formylphenyl)phenanthrene (yield: 89%).

(5-2) Synthesis of 9-[1-(2-methoxyvinyl)phenyl]phenanthrene

A reaction vessel was charged with 9-(2-formylphenyl)phenanthrene (25.0 g), methoxymethyltriphenylphosphonium chloride (33.4 g), and tetrahydrofuran (300 ml) in an argon atmosphere. t-Butoxypotassium (11.9 g) was added to the mixture at room temperature with stirring. After stirring the mixture at room temperature for 2 hours, water (200 ml) was added to the mixture. The reaction mixture was extracted with diethyl ether, and the aqueous layer was removed. The organic layer was washed with water and a saturated sodium chloride solution, and dried over magnesium sulfate. After removing magnesium sulfate by filtration, the organic layer was concentrated. The residue was purified by silica gel column chromatography to obtain 24.0 g of the target 9-[1-(2-methoxyvinyl)phenyl]phenanthrene (yield: 87%).

(5-3) Synthesis of benzo[g]chrysene

A reaction vessel was charged with 9-[1-(2-methoxyvinyl)phenyl]phenanthrene (24.0 g) and dichloromethane (100 ml). 6 drops of methanesulfonic acid were added to the mixture using a Pasteur pipette at room temperature with stirring. The mixture was stirred at room temperature for 8 hours. After completion of the reaction, a 10% potassium carbonate aqueous solution (100 ml) was added to the mixture. After removing the aqueous layer, the organic layer was washed with water and a saturated sodium chloride solution, and dried over magnesium sulfate. After removing magnesium sulfate by filtration, the organic layer was concentrated. The residue was purified by silica gel column chromatography to obtain 5.21 g of the target benzo[g]chrysene (yield: 25%).

(5-4) Synthesis of 10-bromobenzo[g]chrysene

A flask was charged with benzo[g]chrysene (5.21 g) and N,N-dimethylformamide (50 ml). An N,N-dimethylformamide (10 ml) solution of N-bromosuccinimide (4.00 g) was added to the mixture. The mixture was stirred at 80° C. for 8 hours. After cooling the mixture to room temperature, the reaction mixture was poured into water (200 ml). A solid that precipitated by this operation was filtered off, and washed with water and methanol. The solid was purified by silica gel column chromatography to obtain 5.87 g of 10-bromobenzo[g]chrysene (yield: 88%).

(5-5) Synthesis of benzo[g]chrysene-10-boronic acid

A flask was charged with 10-bromobenzo[g]chrysene (5.87 g) in an argon atmosphere, and dehydrated diethyl ether (100 ml) was added to the flask. After cooling the reaction mixture to −40° C., a 1.6 M hexane solution (11 ml) of n-butyllithium was added to the reaction mixture. The reaction mixture was heated to 0° C., and stirred for 1 hour. After cooling the reaction mixture to −60° C., a dehydrated diethyl ether (10 ml) solution of triisopropyl borate (7.72 g) was added dropwise to the reaction mixture. The reaction mixture was stirred at room temperature for 5 hours. After the addition of a 10% hydrochloric acid aqueous solution (50 ml), the mixture was stirred for 1 hour. After removing the aqueous layer, the organic layer was washed with water and a saturated sodium chloride solution, and dried over magnesium sulfate. After removing magnesium sulfate by filtration, the organic layer was concentrated. The resulting solid was washed with hexane to obtain 3.18 g of the target benzo[g]chrysene-10-boronic acid (yield: 60%).

Synthesis Example 6

Synthesis of benzofurano[3,2-b]dibenzofuran-6-boronic acid

Benzofurano[3,2-b]dibenzofuran-6-boronic acid was synthesized in accordance with the following synthesis scheme.

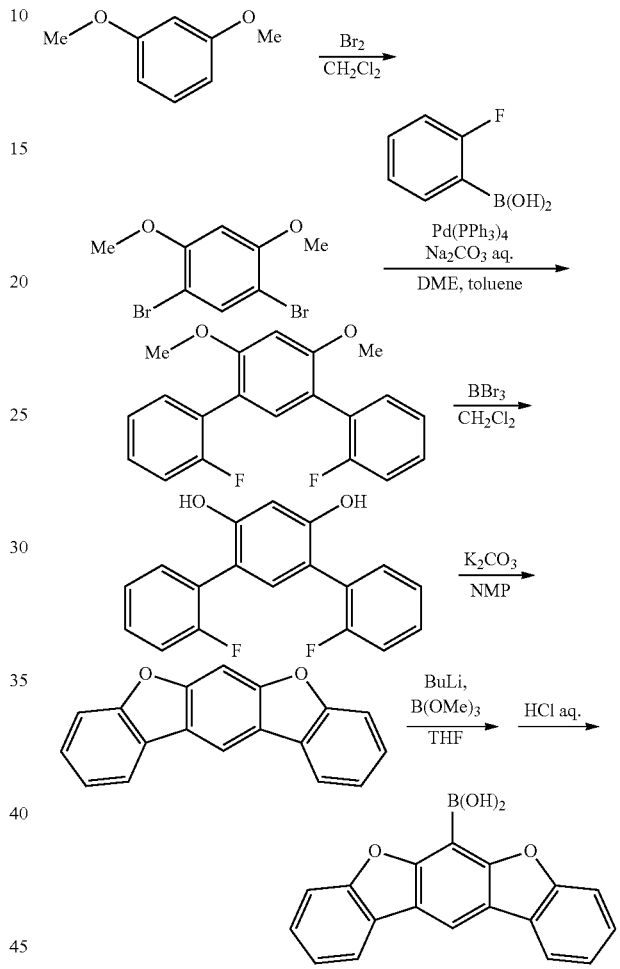

(6-1) Synthesis of 2,4-dibromo-1,5-dimethoxybenzene 1,3-Dimethoxybenzene (53.9 g) was dissolved in dichloromethane (860 ml), and the atmosphere of the system was replaced with argon. A dichloromethane solution (150 ml) of bromine (129.3 g) was added dropwise to the solution over 2.5 hours while cooling the solution with ice. The mixture was allowed to gradually return to room temperature over 3 hours, and stirred for 1 day. The reaction mixture was cooled with ice, and neutralized using a 10% sodium hydroxide aqueous solution. After collecting the dichloromethane layer, the aqueous layer was extracted with dichloromethane. The organic layers were combined and dried over anhydrous sodium sulfate, and filtered. The filtrate was then concentrated. The residue was dispersed in and washed with hexane, and the resulting crystals were filtered off, and dried to obtain 110.5 g of the target 2,4-dibromo-1,5-dimethoxybenzene as white crystals (yield: 97%).

(6-2) Synthesis of 2,4-bis(2-fluorophenyl)-1,5-dimethoxybenzene

A flask was charged with 2,4-dibromo-1,5-dimethoxybenzene (88.8 g), 2-fluorophenylboronic acid (100.74 g), a 2 M sodium carbonate aqueous solution (600 ml), tetrakis(triphenylphosphine)palladium(0) (6.73 g), 1,2-dimethoxyethane (150 ml), and toluene (150 ml), and the mixture was refluxed for 36 hours. After completion of the reaction, water (500 ml) and toluene (1000 ml) were added to the mixture. The mixture was transferred to a separating funnel, and the toluene layer was collected. The toluene layer was dried over anhydrous magnesium sulfate, and impurities were removed using a silica gel short column. The solution was then concentrated. The concentrate was recrystallized from a toluene/hexane mixed solvent to obtain 86.5 g of the target 2,4-bis(2-fluorophenyl)-1,5-dimethoxybenzene as a white solid (yield: 88%).

(6-3) Synthesis of 2,4-bis(2-fluorophenyl)-1,5-dihydroxybenzene

A flask was charged with 1,5-dimethoxy-2,4-bis(2-fluorophenyl)benzene (48.3 g) and dichloromethane (dehydrated) (740 ml), and the mixture was cooled to 0° C. After the addition of boron tribromide (89.0 g), the mixture was stirred at room temperature for 24 hours. After completion of the reaction, the solution was cooled to −78° C., carefully inactivated with methanol, and inactivated again with a sufficient amount of water. The solution was transferred to a separating funnel, extracted with dichloromethane, and dried over anhydrous magnesium sulfate. After removing impurities using a silica gel short column, the solution was concentrated. The concentrate was dried at 60° C. for 5 hours under vacuum to obtain 44.1 g of the target 2,4-bis(2-fluorophenyl)-1,5-dihydroxybenzene as a white solid (yield: 100%).

(6-4) Synthesis of benzofurano[3,2-b]dibenzofuran

A flask was charged with 2,4-bis(2-fluorophenyl)-1,5-dihydroxybenzene (44.14 g) and N-methyl-2-pyrrolidinone (dehydrated) (888 ml), and the solid was completely dissolved in the solvent. After the addition of potassium carbonate (81.8 g), the mixture was stirred at 200° C. for 2 hours. After completion of the reaction, the solution was cooled to room temperature. After the addition of toluene, the mixture was transferred to a separating funnel, and washed with water. The solution was dried over anhydrous magnesium sulfate. After removing impurities using a silica gel short column, the solution was concentrated, and recrystallized from a toluene/hexane mixed solvent to obtain 27.9 g of the target benzofurano[3,2-b]dibenzofuran as a white solid (yield: 73%).

(6-5) Synthesis of benzofurano[3,2-b]dibenzofuran-6-boronic acid

A flask was charged with benzofurano[3,2-b]dibenzofuran (12.9 g) and tetrahydrofuran (dehydrated) (300 ml), and the mixture was cooled to −78° C. After the addition of n-butyllithium (20.0 ml, 2.63 M in hexane), the mixture was allowed to stand at room temperature for 1 hour. The mixture was again cooled to −78° C. After the addition of trimethylborate (10.4 g), the mixture was stirred at −78° C. for 10 minutes, and allowed to stand at room temperature for 1 hour. After completion of the reaction, the solution was concentrated by about half using an evaporator. After the addition of 1 M hydrochloric acid (200 ml), the mixture was stirred at room temperature for 1 hour. The mixture was transferred to a separating funnel, and extracted with ethyl acetate. The solution was dried over anhydrous magnesium sulfate, concentrated, and dispersed in and washed with a toluene/hexane mixed solvent to obtain 13.7 g of the target benzofurano[3,2-b]dibenzofuran-6-boronic acid as a white solid (yield: 91%).

Synthesis Example 7

Synthesis of 10-[4-(1-naphthyl)phenyl]anthracen-9-ylboronic acid

10-[4-(1-naphthyl)phenyl]anthracen-9-ylboronic acid was synthesized in accordance with the following synthesis scheme.

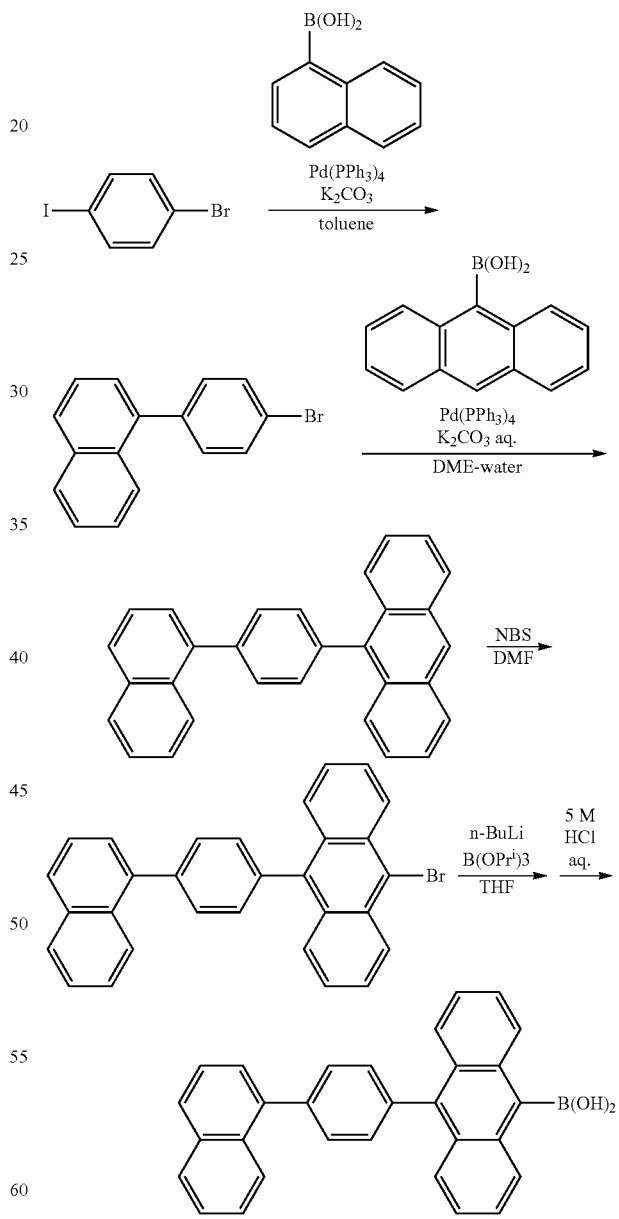

(7-1) Synthesis of 4-(1-naphthyl)bromobenzene

A mixture of 4-bromoiodobenzene (70 g), 1-naphthylboronic acid (47 g), tetrakis(triphenylphosphine)palladium(0)

(5.7 g), potassium carbonate (78.5 g), and toluene (700 ml) was stirred at 74° C. for 44 hours in a nitrogen atmosphere. The reaction mixture was cooled to room temperature, and separated by adding water. The organic layer was washed with a 5% sodium bicarbonate solution and a 5% sodium chloride solution, and concentrated under reduced pressure. The residue was purified by silica gel column chromatography to obtain 53 g of the target 4-(1-naphthyl)bromobenzene (yield: 76%).

(7-2) Synthesis of 9-[4-(1-naphthyl)phenyl]anthracene

A mixture of 4-(1-naphthyl)bromobenzene (53 g), 9-anthrylboronic acid (45 g), tetrakis(triphenylphosphine)palladium(0) (4.3 g), potassium carbonate (59 g), 1,2-dimethoxyethane (526 ml), and water (526 ml) was stirred at 74° C. for 19 hours in a nitrogen atmosphere. The reaction mixture was cooled to room temperature, and the solid produced was filtered off, and washed with water, methanol, and heptane. The resulting solid was purified by silica gel column chromatography to obtain 58 g of the target 9-[4-(1-naphthyl)phenyl]anthracene (yield: 82%).

(7-3) Synthesis of 9-bromo-10-[4-(1-naphthyl)phenyl]anthracene

Dimethylformamide (448 ml) was added to 9-[4-(1-naphthyl)phenyl]anthracene (56 g), and the mixture was heated to 35° C. and stirred in a nitrogen atmosphere. After the dropwise addition of a dimethylformamide (86 ml) solution of N-bromosuccinimide (29 g) to the reaction mixture, the reaction mixture was stirred for 2 hours. After allowing the reaction mixture to return to room temperature, water was added to the reaction mixture. The resulting solid was filtered off, and washed with water. The solid was dissolved in chloroform, and the solution was washed with water, dried over anhydrous magnesium sulfate, and concentrated under reduced pressure. The residue was washed with toluene to obtain 55 g of the target 9-bromo-10-[4-(1-naphthyl)phenyl]anthracene (yield: 81%).

(7-4) Synthesis of 10-[4-(1-naphthyl)phenyl]anthracen-9-ylboronic acid

9-Bromo-10-[4-(1-naphthyl)phenyl]anthracene (54 g) was dissolved in tetrahydrofuran (540 ml) in a nitrogen atmosphere, and the solution was cooled to −65° C. After the dropwise addition of a hexane solution (58 ml) of 2.44 M n-butyllithium, the mixture was stirred for 2 hours. After the dropwise addition of trimethyl borate (24.4 g) to the reaction mixture, the mixture was stirred for 1 hour. The mixture was allowed to return to room temperature, and then stirred for 1 hour. The reaction mixture was made acidic by adding 5 M hydrochloric acid (270 ml) dropwise to the reaction mixture. The mixture was extracted with toluene, washed with a 5% sodium bicarbonate solution and a 5% sodium chloride solution, and concentrated under reduced pressure. The residue was washed with toluene to obtain 31 g of the target 10-[4-(1-naphthyl)phenyl]anthracen-9-ylboronic acid (yield: 62%).

Synthesis Example 8

Synthesis of Compound ET 2-17

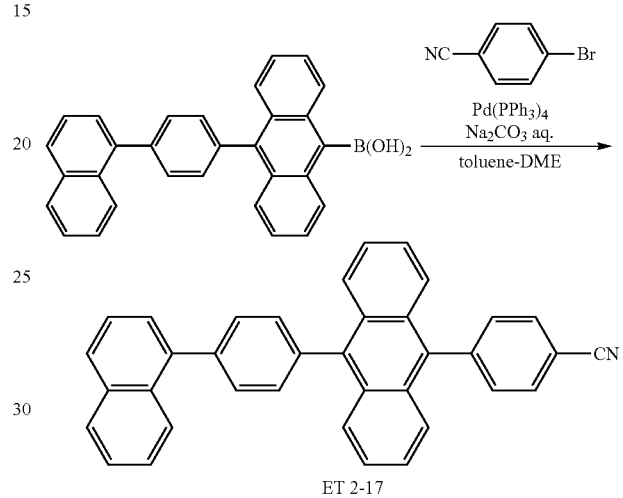

ET 2-17

A mixture of 10-[4-(1-naphthyl)phenyl]anthracen-9-ylboronic acid obtained in Synthesis Example 7 (8.5 g), 4-bromobenzonitrile (3.8 g), tetrakis(triphenylphosphine)palladium(0) (0.4 g), toluene (49 ml), 1,2-dimethoxyethane (21 ml), and a 2 M sodium carbonate aqueous solution (30 ml) was heated and refluxed for 7 hours in an argon atmosphere. The reaction mixture was separated, and extracted with toluene. The organic layer was washed with water and a saturated sodium chloride solution, dried over anhydrous sodium sulfate, and concentrated under reduced pressure. The residue was purified by silica gel column chromatography to obtain 5.0 g of the target compound ET 2-17 (yield: 52%). As a result of mass spectrum analysis, it was found that the compound ET 2-17 had a molecular weight of 481.18 (m/e=481).

Synthesis Example 9

Synthesis of Compound ET 3-05

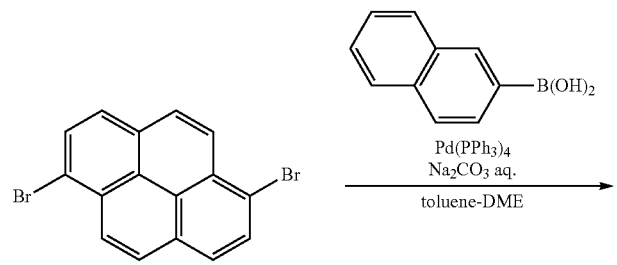

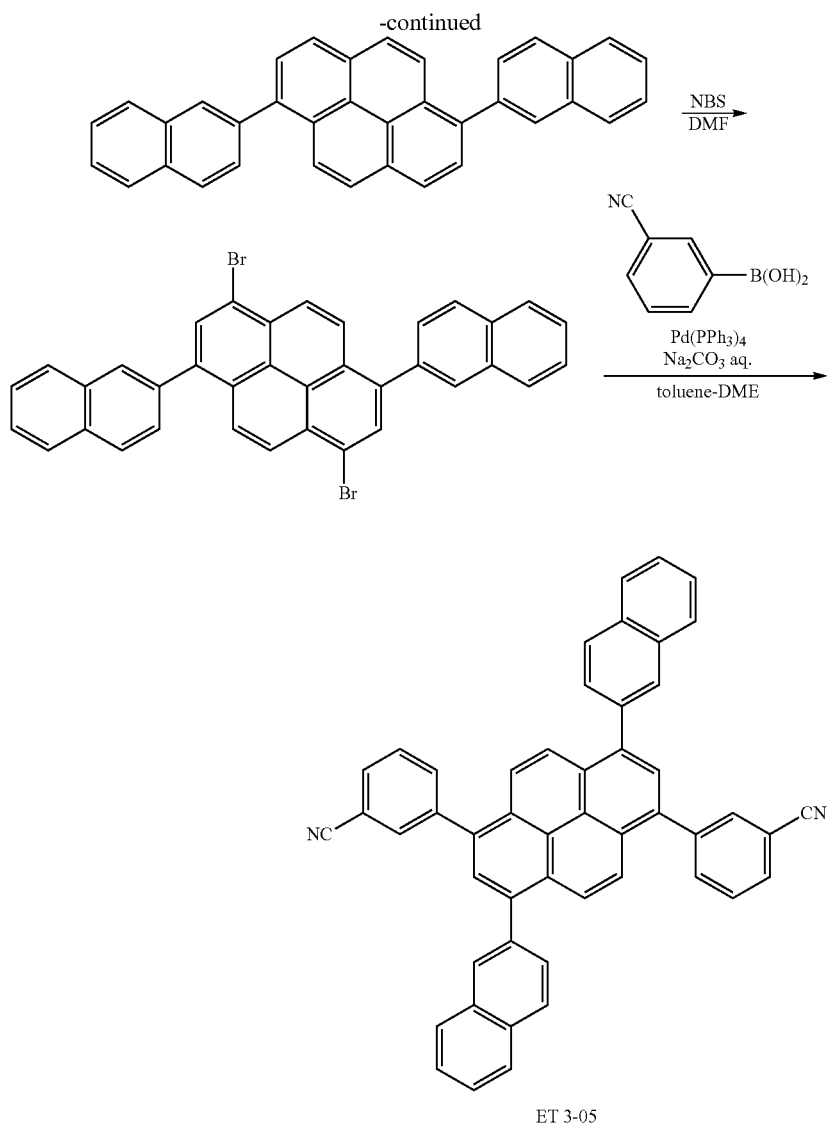

ET 3-05

(9-1) Synthesis of 1,6-di(2-naphthyl)pyrene

A mixture of 1,6-dibromopyrene (10.0 g), 2-naphthylboronic acid (11.9 g), tetrakis(triphenylphosphine)palladium (0) (1.28 g), toluene (70 ml), tetrahydrofuran (70 ml), and a 2 M sodium carbonate aqueous solution (83 ml) was heated and refluxed at 90° C. for 8 hours in an argon atmosphere. The reaction mixture was cooled to room temperature. The resulting precipitate was filtered off, and washed with water and methanol. The residue was purified by silica gel column chromatography, and recrystallized to obtain 11.85 g of the target 1,6-di(2-naphthyl)pyrene (yield: 94%).

(9-2) Synthesis of 1,6-dibromo-3,8-di(2-naphthyl)pyrene

Bromine (3.3 ml) was added dropwise to a mixture of 1,6-di(2-naphthyl)pyrene (11.8 g) and chloroform (370 ml) at room temperature in an argon atmosphere, and the mixture was stirred for 6 hours. The reaction mixture was cooled to room temperature, and the precipitate was filtered off, and washed with water and methanol. The resulting solid was repeatedly recrystallized from toluene to obtain 8.1 g of the target 1,6-dibromo-3,8-di(2-naphthyl)pyrene (yield: 51%).

(9-3) Synthesis of Compound ET 3-05

A mixture of 1,6-dibromo-3,8-di(2-naphthyl)pyrene (6.0 g), 3-cyanophenylboronic acid (3.9 g), tetrakis(triphenylphosphine)palladium(0) (0.45 g), toluene (49 ml), dimethoxyethane (49 ml), and a 2 M sodium carbonate aqueous solution (29 ml) was heated and refluxed for 8 hours in an argon atmosphere. The reaction mixture was cooled to room temperature. The resulting solid was filtered off, and washed with water and methanol. The residue was purified by silica gel column chromatography, and washed with hot toluene and hot dioxane to obtain 5.0 g of the target compound ET 3-05 (yield: 74%). As a result of mass spectrum analysis, it was found that the compound ET 3-05 had a molecular weight of 656.23 (m/e=656).

Synthesis Example 10
Synthesis of ET 3-43
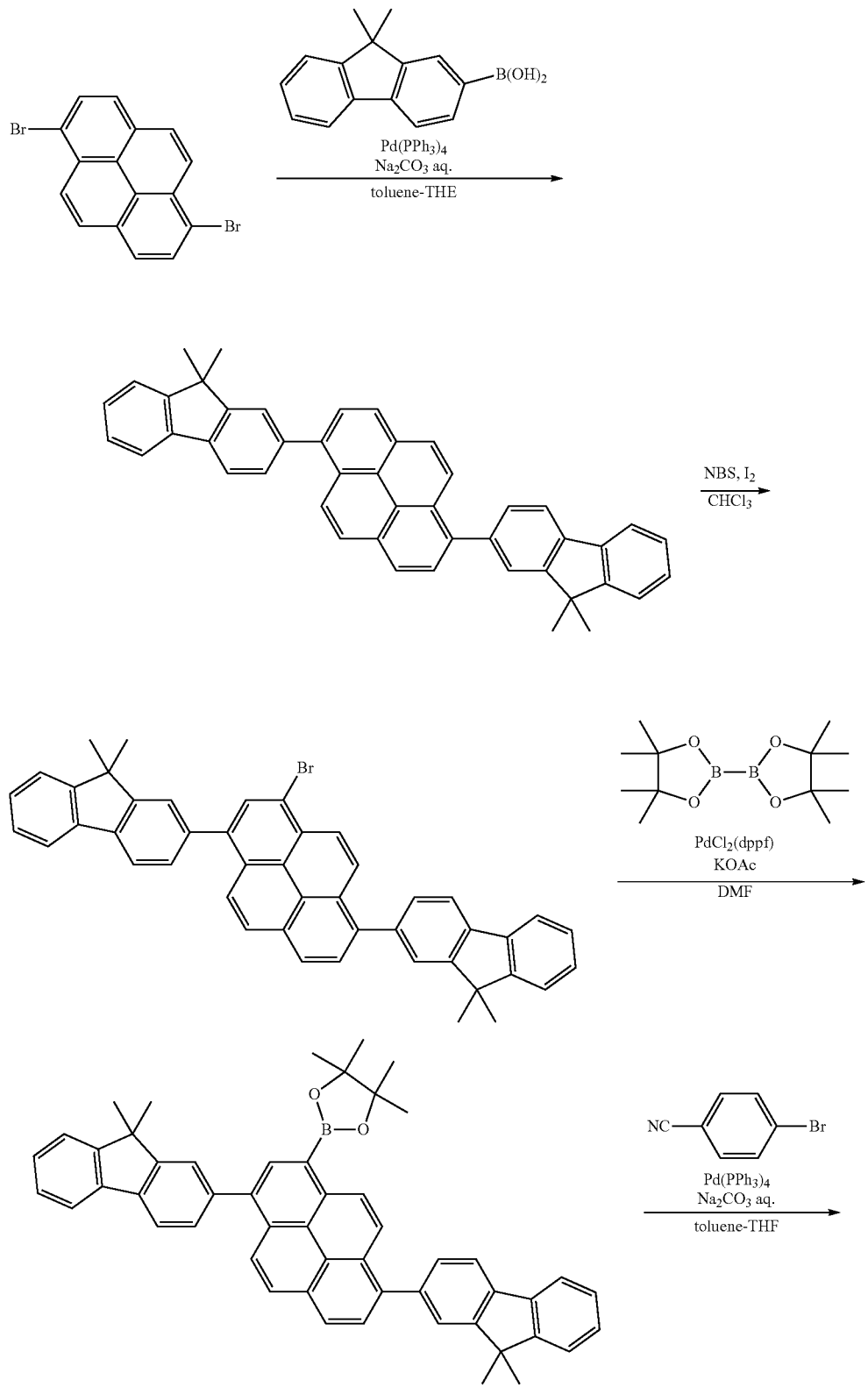

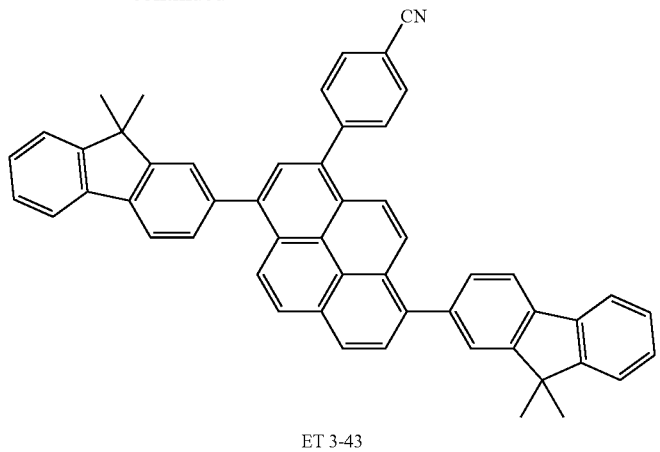

ET 3-43

(10-1) Synthesis of 1,6-bis(9,9-dimethyl-9H-fluoren-2-yl)pyrene

A mixture of 1,6-dibromopyrene (13.6 g), 9,9-dimethyl-9H-fluoren-2-ylboronic acid (22.5 g), tetrakis(triphenylphosphine)palladium(0) (1.7 g), toluene (95 ml), tetrahydrofuran (95 ml), and a 2 M sodium carbonate aqueous solution (113 ml) was stirred at 85° C. for 8 hours in an argon atmosphere. The reaction mixture was cooled to room temperature. The resulting solid was filtered off, and washed with water and methanol. The residue was purified by silica gel column chromatography, and recrystallized to obtain 23.8 g of a solid mainly containing the target 1,6-bis(9,9-dimethyl-9H-fluoren-2-yl)pyrene.

(10-2) Synthesis of 3-bromo-1,6-bis(9,9-dimethyl-9H-fluoren-2-yl)pyrene

A mixture of 1,6-bis(9,9-dimethyl-9H-fluoren-2-yl)pyrene (10 g) obtained in (10-1) and chloroform (1700 ml) was heated and stirred at 50° C. in an argon atmosphere. After 1,6-bis(9,9-dimethyl-9H-fluoren-2-yl)pyrene was completely dissolved in chloroform, N-bromosuccinimide (3.0 g) and a fraction of iodine were added to the solution. The mixture was stirred at 50° C. for 3 hours. The reaction mixture was then cooled to room temperature, and separated by adding water. The chloroform layer was washed with a saturated sodium thiosulfate aqueous solution and a saturated sodium chloride solution, dried over anhydrous sodium sulfate, and concentrated under reduced pressure. The residue was recrystallized from toluene, and the resulting crystals were washed with methanol to obtain 4.9 g of a solid mainly containing the target 3-bromo-1,6-bis(9,9-dimethyl-9H-fluoren-2-yl)pyrene (purity: 85.6%).

(10-3) Synthesis of 3,8-bis(9,9-dimethyl-9H-fluoren-2-yl)pyren-1-ylboronic acid pinacol ester A mixture of 3-bromo-1,6-bis(9,9-dimethyl-9H-fluoren-2-yl)pyrene obtained in (10-2) (4.8 g), bis(pinacolato)diboron (2.8 g), a dichloromethane adduct of [1,1'-bis(diphenylphospino)ferrocene]dichloropalladium(II) (0.18 g), potassium acetate (1.4 g), and dimethylformamide (724 ml) was stirred at 80° C. for 8 hours in an argon atmosphere. The reaction mixture was cooled to room temperature. After the addition of water, the mixture was extracted with ethyl acetate. The ethyl acetate layer was washed with a saturated sodium chloride solution, dried over anhydrous sodium sulfate, and concentrated under reduced pressure. The residue was purified by silica gel column chromatography to obtain 0.89 g of the target 3,8-bis(9,9-dimethyl-9H-fluoren-2-yl)pyren-1-ylboronic acid pinacol ester.

(10-4) Synthesis of Compound ET 3-43

A mixture of 3,8-bis(9,9-dimethyl-9H-fluoren-2-yl)pyren-1-ylboronic acid pinacol ester (0.89 g), 4-bromobenzonitrile (0.34 g), tetrakis(triphenylphosphine)palladium(0) (0.065 g), toluene (6 ml), tetrahydrofuran (6 ml), and a 2 M sodium carbonate aqueous solution (2.8 ml) was stirred at 90° C. for 7 hours in an argon atmosphere. The reaction solution was cooled to room temperature, extracted with toluene, washed with a saturated sodium chloride solution, dried over an anhydrous sodium sulfate aqueous solution, and concentrated under reduced pressure. The residue was purified by silica gel column chromatography to obtain 0.59 g of the target compound ET 3-43 (yield: 68%). As a result of mass spectrum analysis, it was found that the compound ET 3-43 had a molecular weight of 687.29 (m/e=687).

Synthesis Example 11

Synthesis of ET 4-14

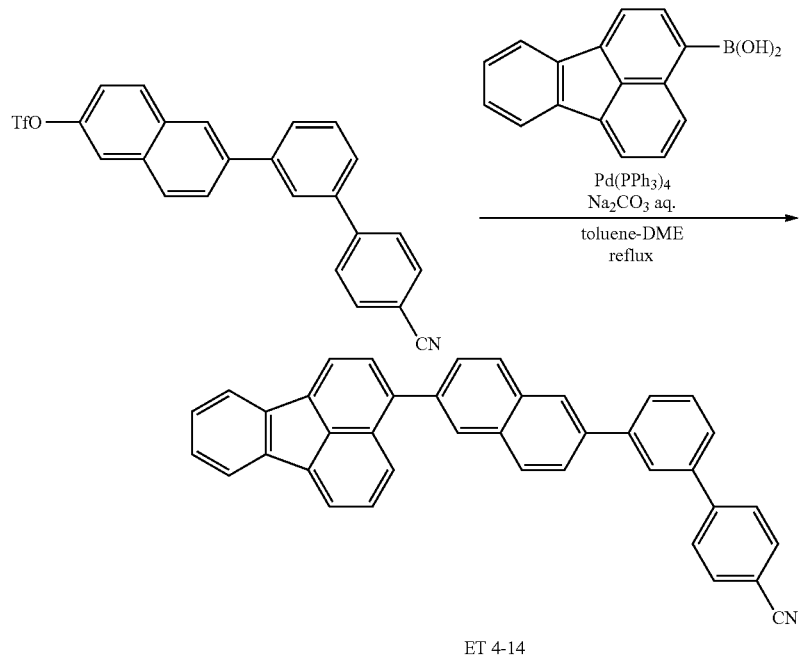

ET 4-14

A mixture of 6-(4'-cyanobiphenyl-3-yl)naphthalen-2-yl trifluoromethanesulfonate obtained in Synthesis Example 4 (3.63 g), 3-fluoranthenylboronic acid (2.17 g), tetrakis(triphenylphosphine)palladium(0) (0.28 g), toluene (12 ml), 1,2-dimethoxyethane (12 ml), and a 2 M sodium carbonate aqueous solution (12 ml) was heated and refluxed for 5 hours in an argon atmosphere. The reaction mixture was then cooled to room temperature. After the addition of water, the mixture was extracted with dichloromethane. The organic layer was washed with a saturated sodium chloride solution, dried over anhydrous sodium sulfate, and concentrated under reduced pressure. The residue was purified by silica gel column chromatography to obtain 3.45 g of the target ET 4-14 (yield: 85%). As a result of mass spectrum analysis, it was found that the compound ET 4-14 had a molecular weight of 505.18 (m/e=505).

Synthesis Example 12

Synthesis of Compound ET 6-02

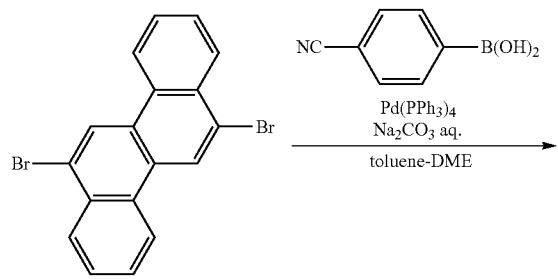

-continued

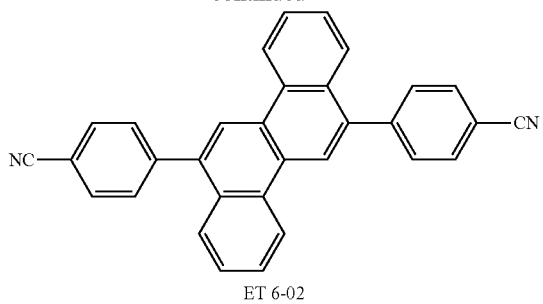

ET 6-02

A mixture of 6,12-dibromochrysene (5.79 g), 4-cyanophenylboronic acid (5.29 g), tetrakis(triphenylphosphine)palladium(0) (1.04 g), toluene (45 ml), 1,2-dimethoxyethane (45 ml), and a 2 M sodium carbonate aqueous solution (45 ml) was heated and refluxed for 6 hours in an argon atmosphere. The reaction mixture was then cooled to room temperature. After the addition of water, the mixture was stirred for 1 hour. The resulting solid was filtered off, washed with water and methanol, and dried under reduced pressure. The resulting solid was repeatedly washed with hot chlorobenzene, and purified by sublimation to obtain 2.57 g of the target compound ET 6-02 (yield: 40%). As a result of mass spectrum analysis, it was found that the compound ET 6-02 had a molecular weight of 430.15 (m/e=430).

Synthesis Example 13

Synthesis of Compound ET 7-10

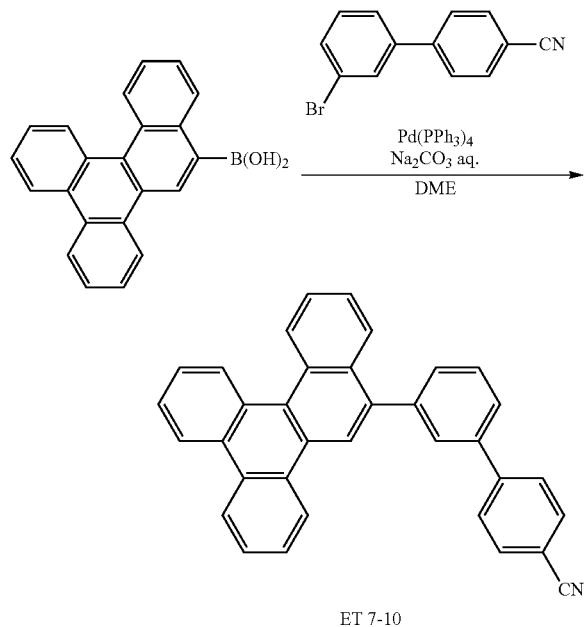

ET 7-10

A mixture of 3'-bromo-4-cyanobiphenyl obtained in Synthesis Example 2 (1.49 g), benzo[g]chrysene-10-boronic acid obtained in Synthesis Example 5 (2.05 g), tetrakis(triphenylphosphine)palladium(0) (0.20 g), 1,2-dimethoxyethane (18 ml), and a 2 M sodium carbonate aqueous solution (9 ml) was heated and refluxed for 5.5 hours in an argon atmosphere. The reaction mixture was then cooled to room temperature. After the addition of water, the mixture was extracted with toluene. The organic layer was washed with a saturated sodium chloride solution, dried over anhydrous sodium sulfate, and concentrated under reduced pressure. The residue was purified by silica gel column chromatography to obtain 1.54 g of the target ET 7-10 (yield: 59%). As a result of mass spectrum analysis, it was found that the compound ET 7-10 had a molecular weight of 455.17 (m/e=455).

Synthesis Example 14

Synthesis of Compound ET 9-08

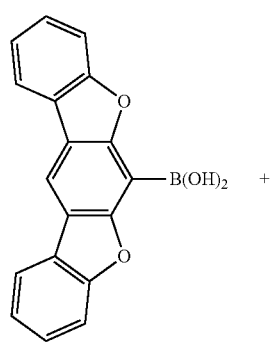

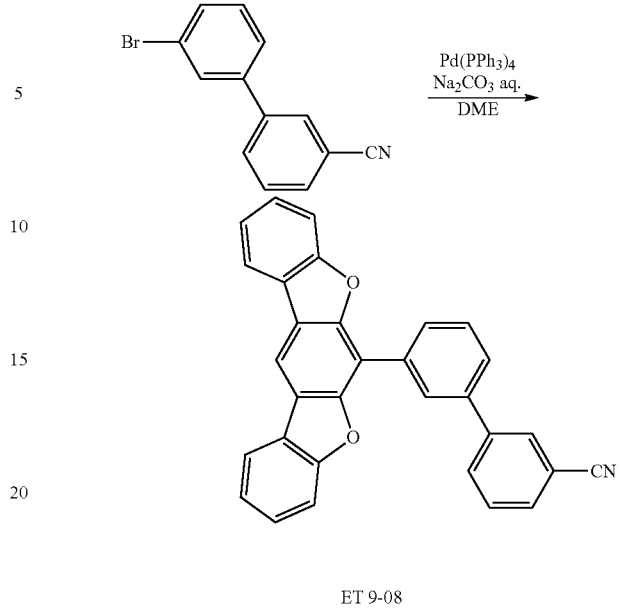

ET 9-08

A mixture of 3'-bromo-4-cyanobiphenyl obtained in Synthesis Example 3 (3.0 g), benzofurano[3,2-b]dibenzofuran-6-boronic acid obtained in Synthesis Example 6 (3.9 g), tetrakis(triphenylphosphine)palladium(0) (0.67 g), toluene (29 ml), 1,2-dimethoxyethane (29 ml), and a 2 M sodium carbonate aqueous solution (23 ml) was heated and refluxed for 8 hours in an argon atmosphere. The reaction mixture was then cooled to room temperature. The resulting solid was filtered off, and washed with water and methanol. The residue was purified by silica gel column chromatography to obtain 2.89 g of the target ET 9-08 (yield: 57%). As a result of mass spectrum analysis, it was found that the compound ET 9-08 had a molecular weight of 435.13 (m/e=435).

Examples 19 to 30 and Comparative Examples 4 to 7

An organic EL device was fabricated in the same manner as in Example 1, except that the compound shown in Table 3 was used as the electron-transporting material instead of the compound ET 1-01, and the compound shown in Table 3 was used as the dopant. The drive voltage, the luminous efficiency (L/J), and the half life of the resulting organic EL device were evaluated. The results are shown in Table 3.

TABLE 3

| | Electron-transporting material | Dopant | Drive voltage [V] | Current efficiency (L/J) [cd/A] | Half life [h] |
|---|---|---|---|---|---|
| Example 19 | ET 2-17 | BD-1 | 3.4 | 7.3 | 6500 |
| Example 20 | ET 3-05 | BD-1 | 4.3 | 5.2 | 5000 |
| Example 21 | ET 4-14 | BD-1 | 3.7 | 8.6 | 9000 |
| Example 22 | ET 6-02 | BD-1 | 4.9 | 6.1 | 5000 |
| Example 23 | ET 7-10 | BD-1 | 3.7 | 8.6 | 5500 |
| Example 24 | ET 9-08 | BD-1 | 4.3 | 9.3 | 4500 |
| Example 25 | ET 1-19 | BD-2 | 3.9 | 7.8 | 9000 |
| Example 26 | ET 1-22 | BD-2 | 3.4 | 8.3 | 6000 |
| Example 27 | ET 1-23 | BD-2 | 3.4 | 8.1 | 6000 |
| Example 28 | ET 1-36 | BD-2 | 3.7 | 8.9 | 4500 |
| Example 29 | ET 2-17 | BD-2 | 3.5 | 8.2 | 7000 |
| Example 30 | ET 3-43 | BD-2 | 4.8 | 6.0 | 9000 |

TABLE 3-continued

| | Electron-transporting material | Dopant | Drive voltage [V] | Current efficiency (L/J) [cd/A] | Half life [h] |
|---|---|---|---|---|---|
| Com. Ex. 4 | C-4 | BD-1 | 5.5 | 4.4 | 3000 |
| Com. Ex. 5 | C-5 | BD-1 | 6.0 | 3.9 | 2500 |
| Com. Ex. 6 | C-6 | BD-1 | 6.3 | 3.5 | 3000 |
| Com. Ex. 7 | C-7 | BD-2 | 6.6 | 2.0 | 500 |

As shown in Table 3, a decrease in drive voltage, an increase in efficiency, and an increase in lifetime were achieved when using the compound including a cyano group and an aromatic ring group as the electron-transporting material.

It was thus confirmed that the aromatic ring group in the electron-transporting material that includes a cyano group and an aromatic ring group is not limited to an aromatic ring group having a particular structure, but may be a known aromatic ring group. It was also confirmed that various dopants may be used for the emitting layer.

INDUSTRIAL APPLICABILITY

An organic EL device that includes the electron-transporting material according to the invention may be used for a large television display panel, an illumination panel, and the like for which a reduction in power consumption is desired.

Although only some exemplary embodiments and/or examples of the invention have been described in detail above, those skilled in the art will readily appreciate that many modifications are possible in the exemplary embodiments and/or examples without materially departing from the novel teachings and advantages of the invention. Accordingly, all such modifications are intended to be included within the scope of the invention.

The documents described in the specification are incorporated herein by reference in their entirety.

The invention claimed is:

1. An organic electroluminescence device comprising, in order: an anode, an emitting layer, an electron-transporting region, and a cathode, the electron-transporting region comprising an electron-transporting material has a formula (ET),

wherein $L_1$ is a single bond or a substituted or unsubstituted (a+1)-valent aromatic ring group having 6 to 50 ring carbon atoms, $Ar_1$ is a substituted or unsubstituted (1+b)-valent aromatic ring group having 6 to 50 ring carbon atoms, a, b, and c are each independently an integer from 1 to 3, when $L_1$ and $Ar1$ have a substituent, the substituent is unsubstituted and selected from the group consisting of an alkyl group, an alkylsilyl group, a halogenated alkyl group, a phenyl group, a biphenyl group, terphenyl group, a naphthyl group, a phenanthryl group, an anthryl group, a 9,9-dimethylfluorenyl group, a benzanthryl group, a pyrenyl group, a cycloalkyl group, an alkoxy group, a heterocyclic group that does not include a nitrogen atom, an alkoxycarbonyl group, a halogen atom, a hydroxyl group, a nitro group, a cyano group, and a carboxyl group, and A is a fused aromatic ring group having a formula selected from the group consisting of formulas (A-3), and A(5) to (A-7),

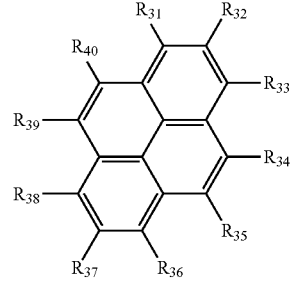

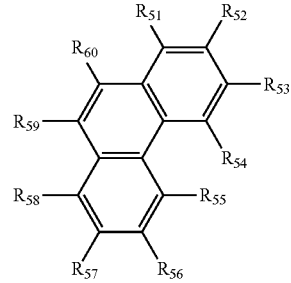

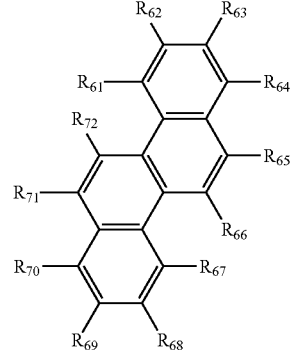

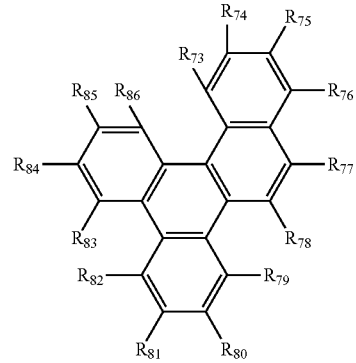

wherein c of $R_{31}$ to $R_{40}$, $R_{51}$ to $R_{60}$, $R_{61}$ to $R_{72}$, or $R_{73}$ to $R_{86}$, bond to $L_1$ as a single bond, and the remainder of $R_1$ to $R_{12}$, $R_{21}$ to $R_{30}$, $R_{31}$ to $R_{40}$, $R_{51}$ to $R_{60}$, $R_{61}$ to $R_{72}$, or $R_{73}$ to $R_{86}$, are each independently a hydrogen atom, a halogen atom, a cyano group, a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 50 ring carbon atoms, wherein adjacent groups among the remainder of $R_{31}$ to $R_{40}$, $R_{51}$ to $R_{60}$, $R_{61}$ to $R_{72}$, or $R_{73}$ to $R_{86}$, may bond to form a ring.

2. The organic electroluminescence device of claim 1, wherein the electron-transporting region further comprises a reducing dopant.

3. The organic electroluminescence device of claim 2, wherein the reducing dopant is at least one substance selected from the group consisting of an alkali metal, an alkaline-earth metal, a rare earth metal, an alkali metal oxide, an alkali metal halide, an alkaline-earth metal oxide, an alkaline-earth metal halide, a rare earth metal oxide, a rare earth metal halide, an organic complex of art alkali metal, an organic complex of an alkaline-earth metal, and an organic complex of a rare earth metal.

4. A compound comprising a cyano group and an aromatic ring group, having a formula (ET),

 (ET)

wherein $L_1$ is a single bond or a substituted or unsubstituted (a+1)-valent aromatic ring group having 6 to 50 ring carbon atoms, $Ar_1$ is a substituted or unsubstituted (1+b)-valent aromatic ring group having 6 to 50 ring carbon atoms, a, b, and c are each independently an interger from 1 to 3, when $L_1$ and $Ar_1$ have a substituent, the substituent is unsubstituted and selected from the group consisting of an alkyl group, an alkylsilyl group, a halogenated alkyl group, a phenyl group, a biphenyl group, terphenyl group, a naphthyl group , a phenanthryl group, an anthryl group, a 9,9-dimethylfluorenyl group, a benzanthryl group, a pyrenyl group, a cycloalkyl group, an alkoxy group, a heterocyclic group that does not include a nitrogen atom, an alkoxycatbonyl group, a halogen atom, a hydroxyl group, a nitro group, a cyano group, and a carboxyl group, and A is a fused aromatic ring group having a formula selected from the group consisting of formulas (A-3), and A(5) to (A-7),

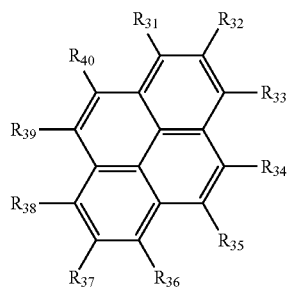 (A-3)

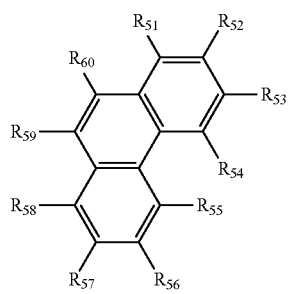 (A-5)

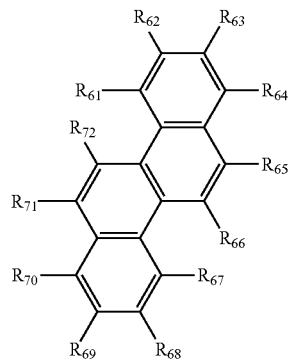 (A-6)

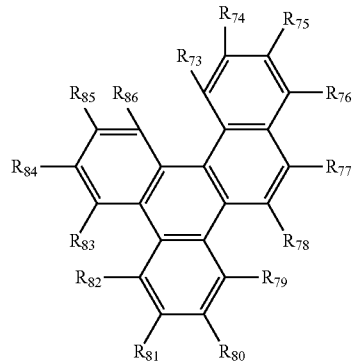 (A-7)

wherein c of $R_{31}$ to $R_{40}$, $R_{51}$ to $R_{60}$, to $R_{61}$ to $R_{72}$, or $R_{73}$ to $R_{86}$ bond to $L_1$ as a single bond, and the remainder of $R_1$ to $R_{12}$, $R_{21}$ to $R_{30}$, $R_{31}$ to $R_{40}$, $R_{51}$ to $R_{60}$, $R_{61}$ to $R_{72}$, or $R_{73}$ to $R_{86}$ are each independently a hydrogen atom, a halogen atom, a cyano group, a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 50 ring carbon atoms, wherein adjacent groups among the remainder of $R_{31}$ to $R_{40}$, $R_{51}$ to $R_{60}$, $R_{61}$ to $R_{72}$, or $R_{73}$ to $R_{86}$ may bond to forma ring.

5. The organic electroluminescence device of claim 1, wherein the electron-transporting material comprises a fused aromatic ring group.

6. The organic electroluminescence device of claim 1, wherein the electron-transporting material comprises a fused aromatic ring group.

7. The organic electroluminescence device of claim 1, wherein the electron-transporting material comprises both a monocyclic aromatic ring group and a fused aromatic ring group.

8. The organic electroluminescence device of claim 5, wherein the monocyclic aromatic ring group is a phenyl group, a biphenyl group, or a terphenyl group.

9. The organic electroluminescence device of claim 6, wherein the fused aromatic ring group is a naphthyl group, a phenanthryl group, an anthryl group, a 9,9-dimethylfluorenyl group, a fluoranthenyl group, a benzanthryl group, a pyrcnyl group, a dihenzothiophenyl group, or a dibenzolliranyl group.

10. The organic electroluminescence device of claim 1, further comprising a hole-transporting region between the anode and the emitting layer.

11. The organic electroluminescence device of claim 1, wherein $L_1$ is a substituted or unsubstituted (a+1)-valent aromatic ring group having 6 to 12ring carbon atoms.

12. The organic electroluminescence device of claim 1, wherein the (1+b)-valent aromatic ring group is a residue that corresponds to a phenyl group or a naphthyl group.

13. The organic electroluminescence device of claim 1, wherein the emitting layer comprises an anthracene compound having a formula (4),

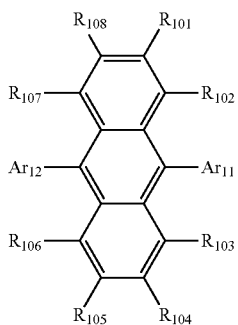

(4)

wherein $Ar_{11}$ and $Ar_{12}$ are each independently a substituted or unsubstituted monocyclic aromatic ring group having 5 to 50 ring atoms, a substituted or unsubstituted fused aromatic ring group having 8 to 50 ring, a combination of the monocyclic aromatic ring group and the fused aromatic ring group, and $R_{101}$ to $R_{108}$ are each independently a group selected from a hydrogen atom, a substituted or unsubstituted monocyclic aromatic ring group having 5 to 50 ring atoms, a substituted or unsubstituted fused aromatic ring group having 8 to 50 ring atoms, a group comprising a combination of the monocyclic aromatic ring roup and the fused aromatic ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

14. The organic electroluminescence device of claim 1, wherein the emitting layer comprises a pyrene compound having a formula (5),

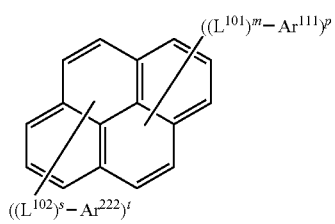

(5)

wherein $Ar^{111}$ and $Ar^{222}$ are each independently a substituted or unsubstituted aryl group having 6 to 30 ring carbon atoms, $L^{101}$ and $L^{102}$ are each independently a substituted or unsubstituted divalent aryl group having 6 to 30 ring carbon atoms, or a heterocyclic group, m is an integer from 0 to 1, p is an integer from 1 to 4, s is an integer from 0 to 1, and t is an integer from 0 to 3.

15. An organic electroluminescence device comprising, in order: an anode, an emitting layer, an electron-transporting region, and a cathode, the electron-transporting region comprising an electron-transporting material has a formula (ET),

(ET)

wherein $L_1$ is a single bond or a substituted or unsubstituted (a+1)-valent aromatic ring group having 6 to 50 ring carbon atoms, $Ar_1$ is an unsubstituted (1+b)-valent aromatic ring group having 6 to 50 ring carbon atoms, a, b, and c are each independently an integer from 1 to 3, and A is a fused aromatic ring group having a formula selected from the group consisting of a formula (A-4),

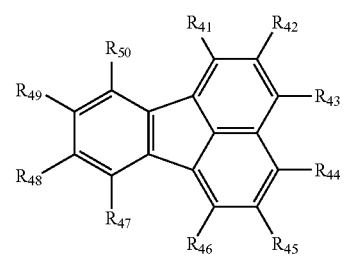

(A-4)

wherein c of $R_{41}$ to $R_{50}$ bond to $L_1$ as a single bond, and the remainder of $R_{41}$ to $R_{50}$ are each independently a hydrogen atom, a halogen atom, a cyano group, a substituted or unsubstituted alkyl group having 1 to 20 carbon atoms, a substituted or unsubstituted cycloalkyl group having 3 to 10 ring carbon atoms, a substituted or unsubstituted silyl group, or a substituted or unsubstituted aryl group having 6 to 50 ring carbon atoms, wherein adjacent groups among the remainder $R_{41}$ to $R_{50}$ may bond to form a ring, with the proviso that the case where $R_{48}$ and $R_{49}$ bond to form a ring is excluded.

16. The organic electroluminesecene device of claim 15, wherein the electron-transporting region further comprises a reducing dopant.

17. The organic electroluminescence device of claim 16, wherein the reducing dopant is at least one substance selected from the group consisting of an alkali metal, an alkaline-earth metal, a rare earth metal, an alkali metal oxide, an alkali metal halide, an alkaline-earth metal oxide, an alkaline-earth metal halide, a rare earth oxide, a rare earth metal halide, an organic complex of an alkali metal, an organic complex of an alkaline-earth metal, and an organic complex of a rare earth metal.

* * * * *

UNITED STATES PATENT AND TRADEMARK OFFICE
CERTIFICATE OF CORRECTION

PATENT NO. : 9,512,137 B2
APPLICATION NO. : 13/509878
DATED : December 6, 2016
INVENTOR(S) : Hirokatsu Ito et al.

It is certified that error appears in the above-identified patent and that said Letters Patent is hereby corrected as shown below:

Column 159, Line 57, "$L_1$ and Arl" should read --$L_1$ and $Ar_1$--.

Column 160, Line 2, "and A(5) to (A-7)," should read --and (A-5) to (A-7),--.

Column 161, Lines 35 & 36, "an alkoxycatbonyl group," should read --an alkoxycarbonyl group,--;
    Line 39, "and A (5) to (A-7)" should read --and (A-5) to (A-7),--.

Column 162, Line 32, "to $R_{61}$ to $R_{72}$, or" should read --$R_{61}$ to $R_{72}$, or--;
    Line 42, "may bond to forma ring" should read --may bond to form a ring--;
    Line 44 & 45, "comprises a fused aromatic" should read --comprises a monocyclic aromatic--;
    Line 59 & 60-61, "a pyrcnyl group," should read --a pyrenyl group,-- and
    "or a dibenzolliranyl group." should read --or a dibenzofuranyl group.--.

Column 163, Line 26 & 27, "50 ring, a combination" should read --50 ring atoms, or a combination--;
    Line 34, "roup" should read --group--.

Column 164, Line 43, "remainder $R_{41}$ to $R_{50}$" should read --remainder of $R_{41}$ to $R_{50}$--;
    Line 54, "a rare earth oxide," should read --a rare earth metal oxide,--.

Signed and Sealed this
Eighteenth Day of April, 2017

Michelle K. Lee
*Director of the United States Patent and Trademark Office*